United States Patent
Murphy et al.

(10) Patent No.: US 7,304,149 B2
(45) Date of Patent: Dec. 4, 2007

(54) BTLA NUCLEIC ACIDS

(75) Inventors: Kenneth P. Murphy, St. Louis, MO (US); Norihiko Watanabe, Chiba (JP); Theresa L. Murphy, St. Louis, MO (US); Jianfei Yang, Sandy Hook, CT (US)

(73) Assignee: Washington University in St. Louis, St. Louis, MO (US)

( * ) Notice: Subject to any disclaimer, the term of this patent is extended or adjusted under 35 U.S.C. 154(b) by 326 days.

(21) Appl. No.: 10/600,997

(22) Filed: Jun. 20, 2003

(65) Prior Publication Data

US 2004/0175380 A1    Sep. 9, 2004

Related U.S. Application Data

(60) Provisional application No. 60/438,593, filed on Jan. 6, 2003, provisional application No. 60/390,653, filed on Jun. 20, 2002.

(51) Int. Cl.
C07H 21/04 (2006.01)
C12N 1/21 (2006.01)
C12N 5/10 (2006.01)

(52) U.S. Cl. ............ 536/23.5; 536/23.1; 435/320.1; 435/252.3; 435/455; 435/69.1

(58) Field of Classification Search ............ None
See application file for complete search history.

(56) References Cited

U.S. PATENT DOCUMENTS 7,153,950 B2 * 12/2006 Clark et al. ............ 536/23.5
2004/0091884 A1 * 5/2004 Clark et al. ............ 435/6

FOREIGN PATENT DOCUMENTS

| WO | WO 99/40100 A1 | 8/1999 |
|---|---|---|
| WO | WO 02/02624 A2 | 1/2002 |
| WO | WO 02/06317 A2 | 1/2002 |
| WO | WO 02/10187 A1 | 2/2002 |
| WO | WO 02/16429 A2 | 2/2002 |
| WO | WO 02/16581 A2 | 2/2002 |
| WO | WO 02/072794 A2 | 9/2002 |
| WO | WO 2004/000221 A2 | 12/2003 |

OTHER PUBLICATIONS

Attwood T., Science 2000; 290:471-473.*
Peach et al., J. Exp. Med., 1994, 180: 2049-2058.*
Watanabe et al., NCBI Accession No. AY293286; May 8, 2003.*
Watanabe et al., Nature Immunol., 2003, 4: 670-679.*
pGEM-T Technical Manual, Promega, 2005, p. 2.*
Abbas, A.K., et al., "T-cell stimulation: an abundance of B7s," *Nat. Med.* 5(12):1345-1346 (Dec. 1999).
Anderson, D., et al., "Paradoxical inhibition of T-cell function in response to CTLA-4 blockade; heterogeneity within the human T-cell population," *Nat. Med.* 6(2):211-214 (Feb. 2000).
Arceci, R., "The potential for antitumor vaccination in acute myelogenous leukemia," *J. Mol. Med.* 76:80-93 (1998).
Bodey, B., et al., "Failure of cancer vaccines: the significant limitations of this approach to immunotherapy," *Anticancer Res.* 20(4):2665-2676 (Jul.-Aug. 2000).
Brodie, D., et al., "LICOS, a primordial costimulatory ligand," *Curr. Biol.* 10(6):333-336 (Mar. 2000).
Carreno, B.M., et al., "B7 family of ligands and its receptors: new pathways for costimulation and inhibition of immune response," *Annu. Rev. Immunol.* 20:29-53 (2002).
Chambers, C., et al., "CTLA-4-mediated inhibition in regulation of T cell responses: mechanisms and manipulation in tumor immunotherapy," *Annu. Rev. Immunol.* 19:565-594 (2001).
Chambers, C., et al., "Thymocyte development is normal in CTLA-4-deficient mice," *Proc. Natl. Acad. Sci. USA* 94(17):9296-9301 (Aug. 1997).
Chapoval, A.I., et al., "B7-H3: a costimulatory molecue for T cell activation and IFN-γ production," *Nat. Immunol.* 2(3):269-274 (Mar. 2001).
Christadoss, P., et al., "Animal models of Myasthenia gravis," *Clin. Immunol.* 94(2):75-87 (Feb. 2000).
Coyle, A.J., et al., "The expanding B7 superfamily: increasing complexity in costimulatory signals regulating T-cell function," *Nat. Immunol.* 2(3):203-209 (Mar. 2001).
Damle, N., et al., "Costimulation of T lymphocytes with integrin ligands intercellular adhesion molecule-1 or vascular cell adhesion molecule-1 induces functional expression of CTLA-4, a second receptor for B7," *J. Immunol.* 152:2686-2697 (1994).
Dong, H., et al., "B7-H1, a third member of the B7 family, co-stimulates T-cell proliferation and interleukin-10 secretion," *Nat. Med.* 5(12):1365-1369 (Dec. 1999).
Dudley, M.E., et al., "Cancer regression and autoimmunity in patients after clonal repopulation with anti-tumor lymphocytes," *Science* 268(5594):850-854 (Oct. 2002).
Egen, J.G., et al., "CTLA-4: new insights into its biological function and use in tumor," *Nat. Immunol.* 3(7):611-618 (Jul. 2002).
Freeman, G.J., et al., "Engagement of the PD-1 immunoinhibitory receptor by a novel B7 family member leads to negative regulation of lymphocyte activity," *J. Exp. Med.* 192(7):1027-1034 (Oct. 2000).
Gao, P., et al., "Tumor vaccination that enhances antitumor T-cell responses does not inhibit the growth of established tumors even in combination with interleukin-12 treatment: the importance of inducing intratumoral T-cell migration," *J. Immunother.* 23(6):643-653 (2000).
Gribben, G., et al., "Alloantigen and concomitant CTLA4 signaling induces clonal deletion of alloreative T cells: a novel method to prevent GVHD," *Blood* 84(10):397a (1994).
Heslop, H., "Cytokine gene transfer in the therapy of malignancy," *Baillière Clin. Haematol.* 7(1):135-151 (Mar. 1994).

(Continued)

Primary Examiner—Phillip Gambel
Assistant Examiner—Ilia Ouspenski

(57) ABSTRACT

The present invention provides a novel lymphocyte inhibitory receptor termed BTLA which is expressed on both T and B cells, and identifies B7 family member B7x as interacting with BTLA to attenuate lymphocyte activity. Methods and compositions for modulating BTLA-mediated negative signaling and interfering with the interaction of BTLA and B7x for therapeutic, diagnostic and research purposes are also provided.

8 Claims, 35 Drawing Sheets

OTHER PUBLICATIONS

Kearney, E., et al., "Antigen-dependent clonal expansion of a trace population of antigen-specific CD4+ T cells in vivo is dependent on CD28 costimulation and inhibited by CTLA-4," *J. Immunol.* 155(3):1032-1036 (Aug. 1995).

Krummel, M., et al., "Superantigen responses and co-stimulation: CD28 and CTLA-4 have opposing effects on T cell expansion in vitro and in vivo," *J. Exp. Med.* 182(2):459-465 (Aug. 1996).

Latchman, Y., et al., "PD-L2 is a second ligand for PD-1 and inhibits T cell activation," *Nat. Immunol.* 2(3):261-268 (Mar. 2001).

Leach, D., et al., "Enhancement of antitumor immunity by CTLA-4 blockade," *Science* 271(5256):1734-1739 (Mar. 1996).

Lee, K.-H., et al., "Increased vaccine-specific T cell frequency after peptide-based vaccination correlates with increased susceptibility to in vitro stimulation but does not lead to tumor regression," *J. Immunol.* 163(11):6292-6300 (Dec. 1999).

Lewis, G., et al., "Growth regulation of human breast and ovarian tumor cells by heregulin: evidence of the requirement of ErbB2 as a critical component in mediating heregulin responsiveness," *Cancer Res.* 56:1457-1465 (Mar. 1996).

Liang, P., et al., "The right place at the right time: novel B7 family members regulate effector T-cell responses," *Curr. Opin. Immunol.* 14(3):384-390 (Jun. 2002).

Ling, V., et al., "Cutting Edge: Identification of GL50, a novel B7-like protein that functionally binds to ICOS receptor," *J. Immunol.* 164(4):1653-1657 (Feb. 2000).

Nishimura, H., et al., "PD-1: an inhibitory immunoreceptor involved in peripheral tolerance," *Trends Biotechnol.* 22(5):265-268 (May 2001).

Pardoll, D.M., et al., "Tumor reactive T cells get a boost," *Nat. Biotechnol.* 20(12):1207-1208 (Dec. 2002).

Sotomayor, E., et al., "In vivo blockade of CTLA-4 enhances the priming of responsive T cells but fails to prevent to induction of tumor antigen-specific tolerance," *Proc. Natl. Acad. Sci. USA* 96(20):11476-11481 (Sep. 1999).

Sun, M., et al., "Characterization of mouse and human B7-H3 genes," *J. Immunol.* 168(12):6294-6297 (Jun. 2002).

Sussman, J., et al., "Activation of T lymphocytes for the adoptive immunotherapy of cancer," *Ann. Surg. Oncol.* 1(4):296-306 (Jul. 1994).

Swallow, M.M., et al., "B7h, a novel costimulatory homolog of B7.1 and B7.2, is induced by TNFα," *Immunity* 11(4):423-432 (Oct. 1999).

Timmerman, J., et al., "Dendritic cell vaccines for cancer immunotherapy," *Annu. Rev. Med.* 50:507-529 (1999).

Triozzi, P., et al., "Clinical and immunologic effects of a synthetic β-human chorionic gonadotropin vaccine," *Int. J. Oncol.* 5:1447-1453 (1994).

Tseng, S.Y., et al., "B7-DC, a new dendritic cell molecule with potent costimulatory properties for T cells," *J. Exp. Med.* 193(7):839-846 (Apr. 2001).

Wallack, M., et al., "Active specific immunotherapy with vaccinia melanoma oncolysate," *Immunity* 1(5):405-413 (Aug. 1994).

Wang, S., et al., "Costimulation of T cells by B7-H2, a B7-like molecule that binds ICOS," *Blood* 96(8):2808-2813 (Oct. 2000).

Yang, Y., et al., "Enhanced induction of antitumor T-cell by cytotoxic T lymphocyte-associated molecule-4 blockade: The effect is manifested only at the restricted tumor-bearing stages," *Cancer Res.* 57:4036-4041 (Sep. 1997).

Yoshinaga, S.K., et al., "T-cell co-stimulation through B7RP-1 and ICOS," *Nature* 402(6763):827-832 (Dec. 1999).

Zaks, T., et al., "Immunization with a peptide epitope (p369-377) from HER-2/neu leads to peptide-specific cytotoxic T lymphocytes that fail to recognize HER-2/neu+ tumors," *Cancer Res.* 58:4902-4908 (Nov. 1998).

Zhu, J., et al., "Cytotoxic T lymphocyte-associated antigen 4 (CTLA-4) blockade enhances incidence and severity of experimental autoimmune neuritis in resistant mice," *J. Neuroimmunol.* 115(1-2):111-117 (Apr. 1999).

\* cited by examiner

FIGURE 1

MOUSE B7x PROTEIN SEQUENCE

MASLGQIIFWSIINIIIILAGAIALIIGFGISGKHFITVTTFTSAGNIGEDGTLSCTFEPDIKLNGIVIQWL

KEGIKGLVHEFKEGKDDLSQQHEMFRGRTAVFADQVVVGNASLRLKNVQLTDAGTYTCYIRTS

KGKGNANLEYKTGAFSMPEINVDYNASSESLRCEAPRWFPQPTVAWASQVDQGANFSEVSNT

SFELNSENVTMKVVSVLYNVTINNTYSCMIENDIAKATGDIKVTDSEVKRRSQLQLLNSGPSPCV

FSSAFAAGWALLSLSCCLMLR

HUMAN B7x PROTEIN SEQUENCE

MASLGQILFWSIISIIIILAGAIALIIGFGISGRHSITVTTVASAGNIGEDGILSCTFEPDIKLSDIVIQWLKEG

VLGLVHEFKEGKDELSEQDEMFRGRTAVFADQVIVGNASLRLKNVQLTDAGTYKCYIITSKGKGNANL

EYKTGAFSMPEVNVDYNASSETLRCEAPRWFPQPTVVWASQVDQGANFSEVSNTSFELNSENVTM

KVVSVLYNVTINNTYSCMIENDIAKATGDIKVTESEIKRRSHLQLLNSKASLCVSSFFAISWALLPLSPYL

MLK

FIGURE 2

MOUSE B7x NUCLEIC ACID SEQUENCE

ATGGCTTCCTTGGGGCAGATCATCTTTTGGAGTATTATTAACATCATCATCATCCTGGCTGGGGC
CATCGCACTCATCATTGGCTTTGGCATTTCAGGCAAGCACTTCATCACGGTCACGACCTTCACCT
CAGCTGGAAACATTGGAGAGGACGGGACCCTGAGCTGCACTTTTGAACCTGACATCAAACTCAA
CGGCATCGTCATCCAGTGGCTGAAAGAAGGCATCAAAGGTTTGGTCCACGAGTTCAAAGAAGGC
AAAGACGACCTCTCACAGCAGCATGAGATGTTCAGAGGCCGCACAGCAGTGTTTGCTGATCAGG
TGGTAGTTGGCAATGCTTCCCTGAGACTGAAAAACGTGCAGCTCACGGATGCTGGCACCTACAC
ATGTTACATCCGCACCTCAAAAGGCAAAGGGAATGCAAACCTAGAGTATAAGACCGGAGCCTTC
AGTATGCCAGAGATAAATGTGGACTATAATGCCAGTTCAGAGAGTTTACGCTGCGAGGCTCCTC
GGTGGTTCCCCCAGCCCACAGTGGCCTGGGCATCTCAAGTCGACCAAGGAGCCAACTTCTCAG
AAGTCTCGAACACCAGCTTTGAGTTGAACTCTGAGAATGTGACCATGAAGGTCGTATCTGTGCTC
TACAATGTCACAATCAACAACACATACTCCTGTATGATTGAAAATGACATTGCCAAAGCCACTGG
GGACATCAAAGTGACAGATTCAGAGGTCAAAAGGCGGAGTCAGCTGCAGCTGCTCAACTCCGG
GCCTTCCCCGTGTGTTTTTTCTTCTGCCTTTGCGGCTGGCTGGGCGCTCCTATCTCTCTCCTGTT
GCCTGATGCTAAGATGA

FIGURE 3

HUMAN B7x NUCLEIC ACID SEQUENCE

ATGGCTTCCCTGGGGCAGATCCTCTTCTGGAGCATAATTAGCATCATCATTATTCTGGCTGGAGC

AATTGCACTCATCATTGGCTTTGGTATTTCAGGGAGACACTCCATCACAGTCACTACTGTCGCCT

CAGCTGGGAACATTGGGGAGGATGGAATCCTGAGCTGCACTTTTGAACCTGACATCAAACTTTCT

GATATCGTGATACAATGGCTGAAGGAAGGTGTTTTAGGCTTGGTCCATGAGTTCAAAGAAGGCAA

AGATGAGCTGTCGGAGCAGGATGAAATGTTCAGAGGCCGGACAGCAGTGTTTGCTGATCAAGTG

ATAGTTGGCAATGCCTCTTTGCGGCTGAAAAACGTGCAACTCACAGATGCTGGCACCTACAAATG

TTATATCATCACTTCTAAAGGCAAGGGGAATGCTAACCTTGAGTATAAAACTGGAGCCTTCAGCA

TGCCGGAAGTGAATGTGGACTATAATGCCAGCTCAGAGACCTTGCGGTGTGAGGCTCCCCGATG

GTTCCCCCAGCCCACAGTGGTCTGGGCATCCCAAGTTGACCAGGGAGCCAACTTCTCGGAAGTC

TCCAATACCAGCTTTGAGCTGAACTCTGAGAATGTGACCATGAAGGTTGTGTCTGTGCTCTACAA

TGTTACGATCAACAACACATACTCCTGTATGATTGAAAATGACATTGCCAAAGCAACAGGGGATA

TCAAAGTGACAGAATCGGAGATCAAAAGGCGGAGTCACCTACAGCTGCTAAACTCAAAGGCTTC

TCTGTGTGTCTCTTCTTTCTTTGCCATCAGCTGGGCACTTCTGCCTCTCAGCCCTTACCTGATGCT

AAAATAA

FIGURE 4

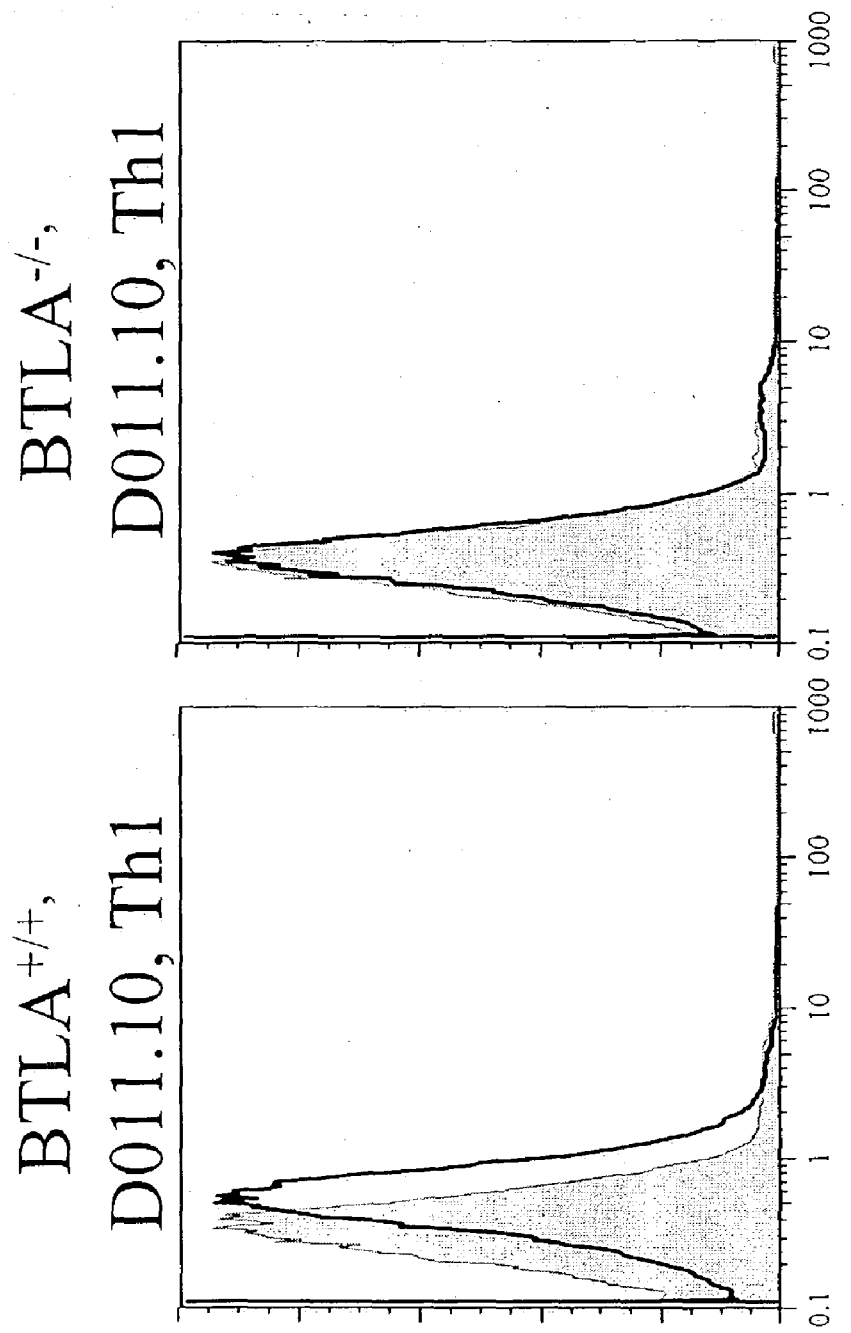

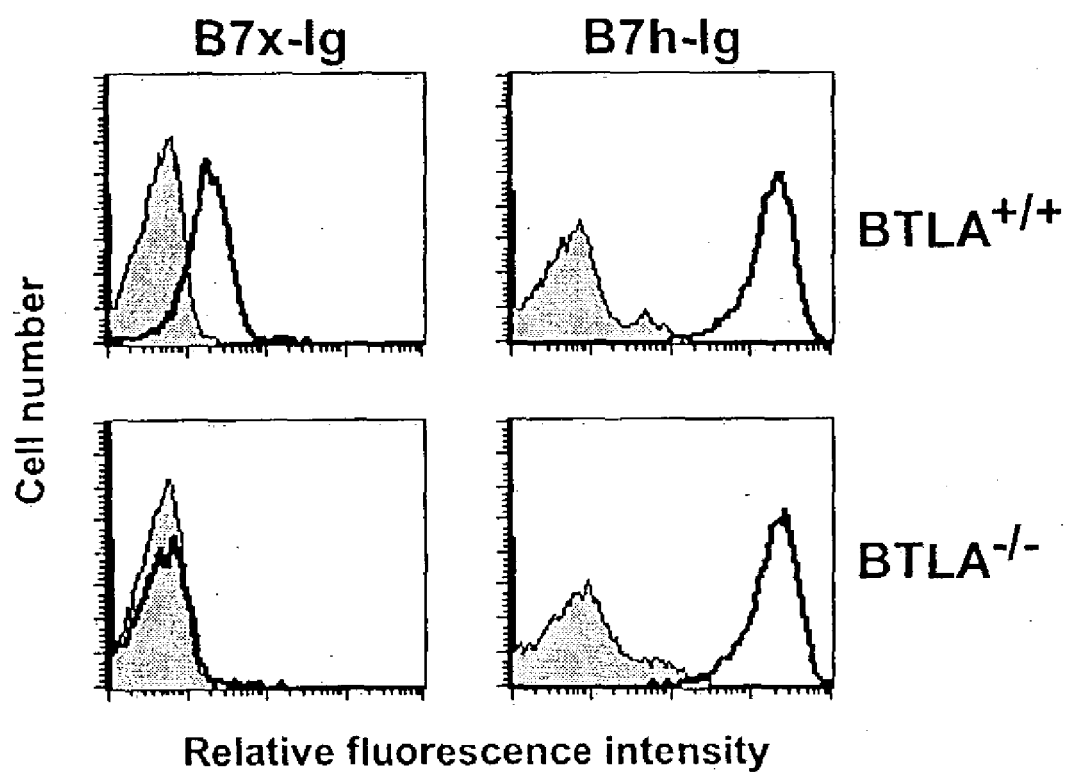

Anti-CD3 (ug/ml)

FIGURE 17
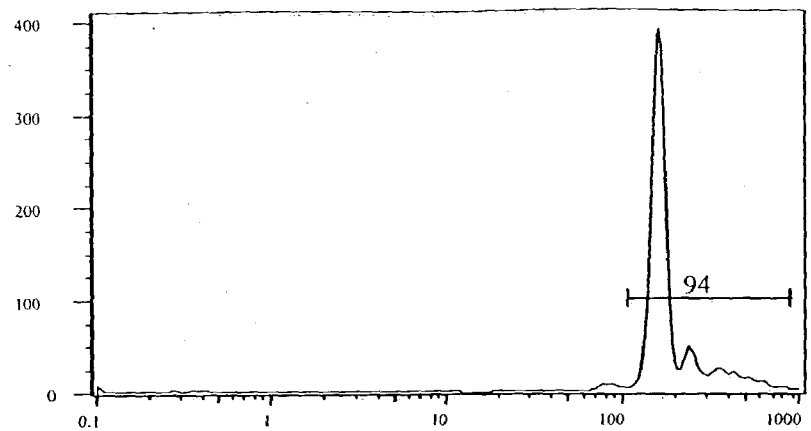
GFP/CHO
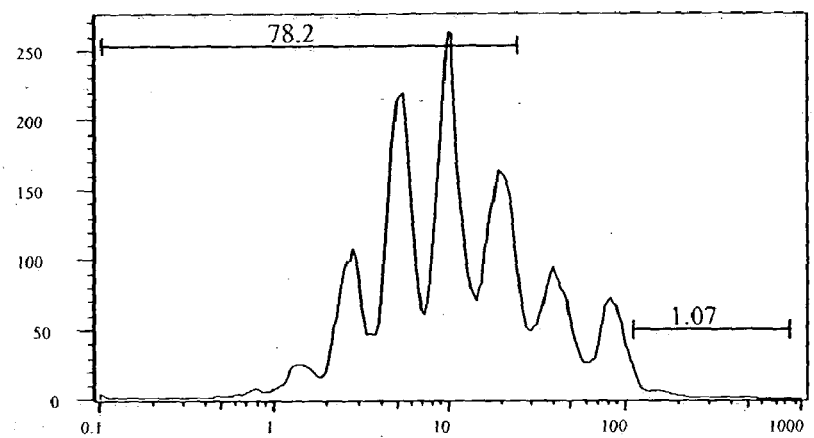
GFP/CHO + anti-CD3
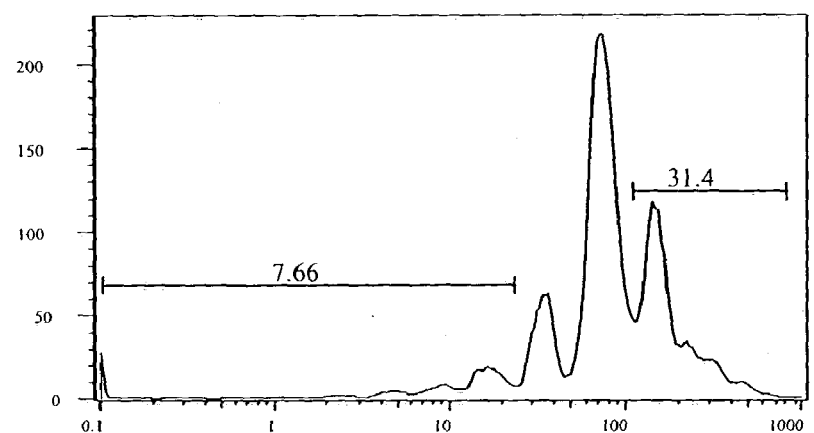
B7x/CHO + anti-CD3

FIGURE 18
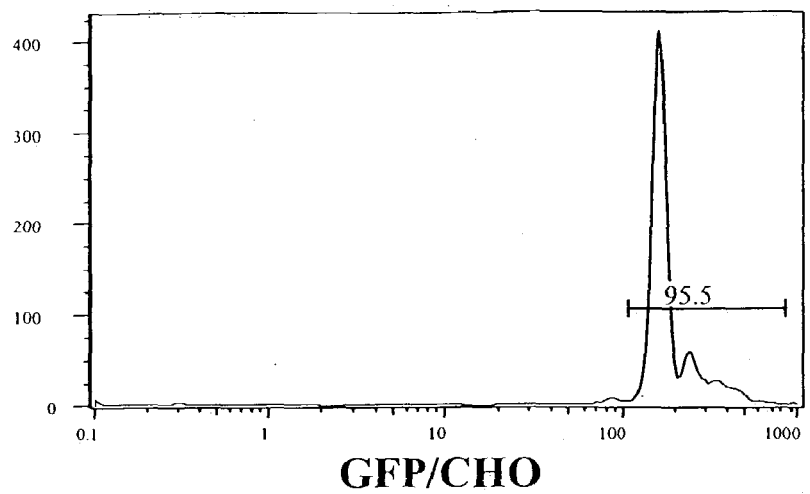
GFP/CHO
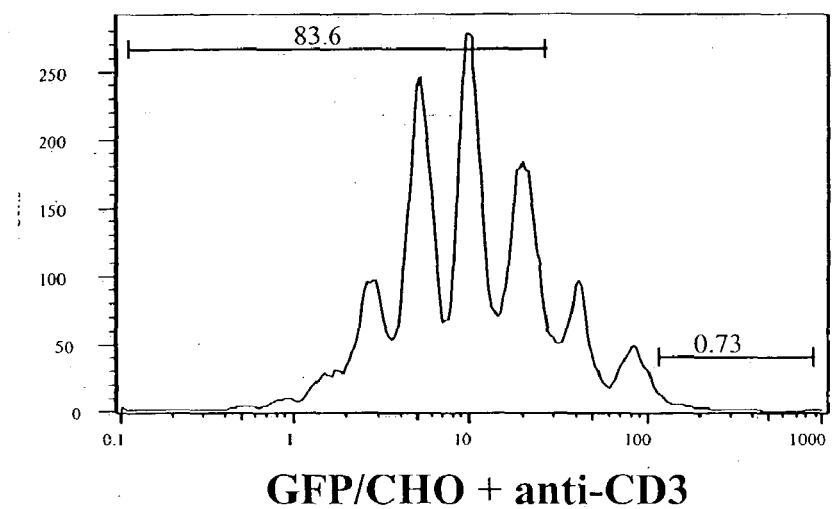
GFP/CHO + anti-CD3
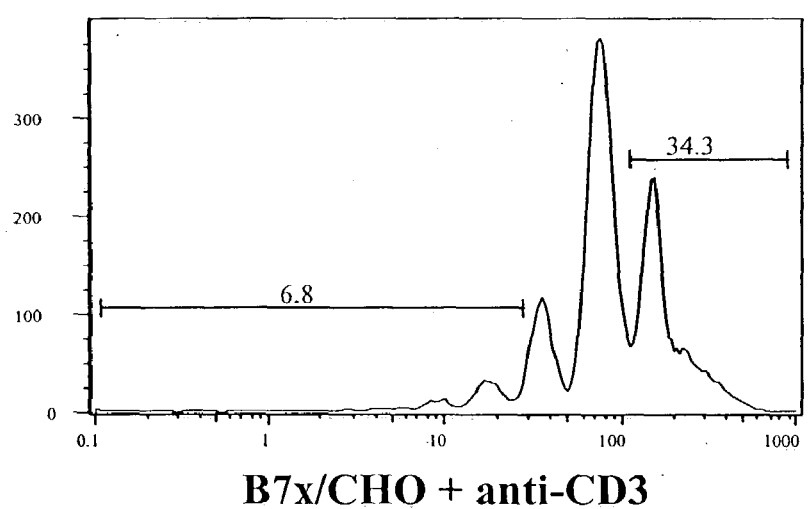
B7x/CHO + anti-CD3

FIGURE 19

```
mouse BTLA   1   MKTVPAMLGTPRLFREFFIL·HLGLWSILCEKATKRNDEE
human BTLA       MKTLPAMLGTGKLFWVFFLIPYLDIWNI·······HGKES 40   CEVQLNIKRNSKHSAWTGELFKIECPVKYCVHRPNVTWCK
                 CDVQLYIKRQSEHSILAGDPFELECPVKYCANRPHVTWCK 80   HNGTIWVPLEVGPQLYTSWEENRSVPVFVLHFKPIHLSDN
                 LNGTTCVKLEDR·Q··TSWKEEKNISFFILHFEPVLPNDN 120   GSYSCSTNFNSQVINSHSVTIHVRERTQNSSEHPLITVSD
                 GSYRCSANFQSNLIESHSTTLYVTDVKSAS··········

160   IPDATNASGPSTMEERPGRTWLLYTLLPLGALLLLL·ACV
                 ·······ERPSKDEMAS·RPWLLYSLLPLGGLPLLITTCF

199   CLLCFLKRIQGKEKKPSDLAGRDTNLVD·······IPASS
                 CLFCCLRRHQGKQNELSDTAGREINLVDAHLKSEQTEAST

232   RTNHQALPSQTGIYDNDRWSS··MQDESELTISLQSERNN
                 RQNSQVLLSETGIYDNDPDLCFRMQEGSEVYSNPCLEENK

270   QGIVYASLNHCVIGRNPRQENNMQEAPTEYASICVRS
                 PGIVYASLNHSVIGLNSRLARNVKEAPTEYASICVRS
```

HUMAN BTLA PROTEIN SEQUENCE

```
  1  mktlpamlgt gklfwvffli pyldiwnihg kescdvqlyi krqsehsila
 51  gdpfelecpv kycanrphvt wcklngttcv kledrqtswk eeknisffil
101  hfepmlpndn gsyrcsanfq snlieshstt lyvtdvkgas erpskdevas
151  rpwllysllp lgglpllitt wfclfcclrr hqgkqnelsd tagreinlvd
201  ahlkseqtea strqnsqvll seagiydndp dlcfrmqegs evcsnpclee
251  nkpgivyasl nhsviglnsr larnvkeapt eyasicvrs
```

HUMAN BTLA NUCLEIC ACID SEQUENCE

```
  1  atgaagacat tgcctgccat gcttggaact gggaaattat tttgggtctt cttcttaatc
 61  ccatatctgg acatctggaa catccatggg aaagaatcat gtgatgtaca gctttatata
121  aagagacaat ctgaacactc catcttagca ggagatccct tgaactaga atgccctgtg
181  aaatactgtg ctaacaggcc tcatgtgact tggtgcaagc tcaatggaac aacatgtgta
241  aaacttgaag atagacaaac aagttggaag gaagagaaga catttcatt tttcattcta
301  cattttgaac caatgcttcc taatgacaat gggtcatacc gctgttctgc aaattttcag
361  tctaatctca ttgaaagcca ctcaacaact ctttatgtga cagatgtaaa aggtgcctca
421  gaacgaccct ccaaggacga agtggcaagc agacc ctggc tcctgtatag tttacttcct
481  ttggggggat gcctctact catcactacc tggttctgcc tgttctgctg cctgagaagg
541  caccaaggaa agcaaaatga actctctgac acagcaggaa gggaaattaa tctggttgat
601  gctcacctta gagcgagca acagaagca agcaccaggc aaaattccca agtactgcta
661  tcagaagctg gaatttatga taatgaccct gacctttgtt tcaggatgca ggaagggtct
721  gaagtttgtt ctaatccatg cctggaagaa acaaaccag gcattgttta tgcttccctg
781  aaccattctg tcattggact gaactcaaga ctggcaagaa atgtaaaaga agcaccaaca
841  gaatatgcat ccatatgtgt gaggagttaa
```

FIGURE 28

MOUSE BTLA PROTEIN SEQUENCE

```
  1  mktvpamlgt prlfreffil hlglwsilce katkrndeec evqlnikrns khsawtqelf
 61  kiecpvkycv hrpnvtwckh ngtiwvplev gpqlytswee nrsvpvfvlh fkpihlsdng
121  syscstnfns qvinshsvti hvrertqnss ehplitvsdi pdatnasgps tmeerpgrtw
181  llytllplga llllacvcl lcflkriqgk ekkpsdlagr dtnlvdipas srtnhqalps
241  gtgiydndpw ssmqdeselt islqsernnq givyaslnhc vigrnprqen nmqeapteya
301  sicvrs
```

MOUSE BTLA NUCLEIC ACID SEQUENCE

```
  1  atgaagacag tgcctgccat gcttgggact cctcggttat tagggaatt cttcatcctc
 61  catctgggcc tctggagcat cctttgtgag aaagctacta gaggaatga tgaagagtgt
121  gaagtgcaac ttaatattaa gaggaattcc aaacactctg cctggacagg agagttattt
181  aaaattgaat gtcctgtgaa atactgtgtt catagaccta atgtgacttg gtgtaagcac
241  aatggaacaa tctgggtacc ccttgaagtt ggtcctcagc tatacactag ttgggaagaa
301  aatcgatcag ttccggtttt tgttctccat tttaaaccaa tacatctcag tgataacggg
361  tcgtatagct gttctacaaa cttcaattct caagttatta atagccattc agtaaccatc
421  catgtgagag aaaggactca aaactcttca gaacaccac taataacagt atctgacatc
481  ccagatgcca ccaatgcctc aggaccatcc accatggaag agaggccagg caggacttgg
541  ctgctttaca ccttgcttcc tttgggggca ttgcttctgc tccttgcctg tgtctgcctg
601  ctctgctttc tgaaaaggat ccaagggaaa gaaaagaagc cttctgactt ggcaggaagg
661  gacactaacc tggttgatat tccagccagt tccaggacaa atcaccaagc actgccatca
721  ggaactggaa tttatgataa tgatccctgg tctagcatgc aggatgaatc tgaattgaca
781  attagcttgc aatcagagag aaacaaccag ggcattgttt atgcttcttt gaaccattgt
841  gttattggaa ggaatccaag acaggaaaac aacatgcagg aggcacccac agaatatgca
901  tccatttgtg tgagaagtta a
```

```
                                                                        Section 1
              (1) 1         10        20        30        40              57
     129 SvJ  (1) GATGAAGAGTGTGAAGTGCAACTTAATATTAAGAGGAATTCCAAACACTCTGCCTGG
 MRL/lpr (bc) (1) GATGAAGAGTGTGAAGTGCAACTTAATATTAAGAGGAATTCCAAACACTCTGCCTGG
     C57Bl/6  (1) GATGAAGAGTGTCCAGTGCAACTTACTATTACGAGGAATTCCAAACAGTCTGCCAGG
       Balb/c (1) GATGAAGAGTGTGAAGTGCAACTTAATATTAAGAGGAATTCCAAACACTCTGCCTGG
         SWR  (1) GATGAAGAGTGTGAAGTGCAACTTAATATTAAGAGGAATTCCAAACACTCTGCCTGG
    NZB/BinJ  (1) GATGAAGACTGTGAAGTGCAACTTAATATTAAGAGGAATTCCAAACACTCTGCCTGG
         NOD  (1) GATGAAGACTGTGAAGTGCAACTTAATATTAAGAGGAATTCCAAACACTCTGCCTGG
     MRL/lpr  (1) GATGAAGAGTGTGAAGTGCAACTTAATATTAAGAGGAATTCCAAACACTCTGCCTGG
      DBA/2J  (1) GATGAAGAGTGTGAAGTGCAACTTAATATTAAGAGGAATTCCAAACAGTCTGCCTGG
        C3H/J (1) GATGAAGAGTGTGAAGTGCAACTTAATATTAAGACGAATTCCAAACACTCTGCCTGG
     129SvEv  (1) GATGAAGAGTGTGAAGTGCAACTTAATATTAAGACGAATTCCAAACACTCTGCCTGG
        SJL.J (1) GATGAAGAGTGTGAAGTGCAACTTAATATTAAGAGGAATTCCAAACACTCTGCCTGG
   Celera old (1) GATGAAGAGTGTGAAGTGCAACTTAATATTAAGAGGAATTCCAAACACTCTGCCTGG
  WEHI 2 old  (1) GATGAAGAGTGTGAAGTGCAACTTAATATTAAGAGGAATTCCAAACACTCTGCCTGG
      Bl/6 old (1) GATGAAGAGTGTCCAGTGCAACTTACTATTACGAGGAATTCCAAACAGTCTGCCAGG
    WEHI 1old (1) GATGAAGAGTGTGAAGTGCAACTTAATATTAAGAGGAATTCCAAACACTCTGCCTGG
    Consensus (1) GATGAAGAGTGTGAAGTGCAACTTAATATTAAGAGGAATTCCAAACACTCTGCCTGG Section 2
              (58) 58        70        80        90       100            114
     129 SvJ  (58) ACAGGAGAGTTATTTAAAATTGAATGTCCTGTGAAATACTGTGTTCATAGACCTAAT
 MRL/lpr (bc) (58) ACAGGAGAGTTATTTAAAATTGAATGTCCTGTGAAATACTGTGTTCATAGACCTCAT
     C57Bl/6  (58) ACAGGAGAGTTATTTAAAATTCAATGTCCTGTGAAATACTGTGTTCATAGACCTAAT
       Balb/c (58) ACAGGAGAGTTATTTAAAATTGAATGTCCTGTGAAATACTGTGTTCATAGACCTAAT
         SWR  (58) ACAGGAGAGTTATTTAAAATTGAATGTCCTGTGAAATACTGTGTTCATAGACCTCAT
    NZB/BinJ  (58) ACAGGAGAGTTATTTAAAATTGAATGTCCTGTGAAATACTGTGTTCATAGACCTAAT
         NOD  (58) ACAGGAGAGTTATTTAAAATTGAATGTCCTGTGAAATACTGTGTTCATAGACCTAAT
     MRL/lpr  (58) ACAGGAGAGTTATTTAAAATTGAATGTCCTGTGAAATACTGTGTTCATAGACCTCAT
      DBA/2J  (58) ACAGGAGAGTTATTTAAAATTGAATGTCCTGTGAAATACTGTGTTCATAGACCTCAT
        C3H/J (58) ACAGGAGAGTTATTTAAAATTGAATGTCCTGTGAAATACTGTGTTCATAGACCTAAT
     129SvEv  (58) ACAGGAGAGTTATTTAAAATTGAATGTCCTGTGAAATACTGTGTTCATAGACCTAAT
        SJL.J (58) ACAGGAGAGTTATTTAAAATTGAATGTCCTGTGAAATACTGTGTTCATAGACCTAAT
   Celera old (58) ACAGGAGAGTTATTTAAAATTGAATGTCCTGTGAAATACTGTGTTCATAGACCTAAT
  WEHI 2 old  (58) ACAGGAGAGTTATTTAAAATTGAATGTCCTGTGGAATACTGTGTTCATAGACCTCAT
      Bl/6 old (58) ACAGGAGAGTTATTTAAAATTCAATGTCCTGTGAAATACTGTGTTCATAGACCTAAT
    WEHI 1old (58) ACAGGAGAGTTATTTAAAATTGAATGTCCTGTGGAATACTGTGTTCATAGACCTCAT
    Consensus (58) ACAGGAGAGTTATTTAAAATTGAATGTCCTGTGAAATACTGTGTTCATAGACCTAAT
```

Section 3

```
                  (115) 115      120       130       140       150       160      171
       129 SvJ    (115) GTGACTTGGTGTAAGCACAATGGAACAATCTGGGTACCCCTTGAAGTTGGTCCTCAG
    MRL/lpr (bc)  (115) GTGACTTGGTGTAAGCACAATGGAACAATCTCGGTACCCCTTGAAGTTGGTCCTCAG
        C57Bl/6   (115) GTGACTTGGTGTAAGCACAATGGAACAATCTGTGTACCCCTTGAGGTTAGCCCTCAG
         Balb/c   (115) GTGACTTGGTGTAAGCACAATGGAACAATCTGGGTACCCCTTGAAGTTGCTCCTCAG
           SWR    (115) GTGACTTGGTGTAAGCACAATGGAACAATCTGGGTACCCCTTGAAGTTGGTCCTCAG
       NZB/BinJ   (115) GTGACTTGGTGTAAGCACAATGGAACAATCTGGGTACCCCTTGAAGTTGGTCCTCAG
           NOD    (115) GTGACTTGGTGTAAGCACAATGGAACAATCTGGGTACCCCTTGAAGTTGCTCCTCAG
        MRL/lpr   (115) GTGACTTGGTGTAAGCACAATGGAACAATCTGGGTACCCCTTGAAGTTGGTCCTCAG
         DBA/2J   (115) GTGACTTGGTGTAAGCACAATGGAACAATCTGGGTACCCCTTGAAGTTGGTCCTCAG
          C3H/J   (115) GTGACTTGGTGTAAGCACAATGGAACAATCTCGGTACCCCTTGAAGTTGGTCCTCAG
        129SvEv   (115) GTGACTTGGTGTAAGCACAATGGAACAATCTGGGTACCCCTTGAAGTTGGTCCTCAG
          SJL.J   (115) GTGACTTGGTGTAAGCACAATGGAACAATCTGGGTACCCCTTGAAGTTGGTCCTCAC
      Celera old  (115) GTGACTTGGTGTAAGCACAATGGAACAATCTCGGTACCCCTTGAAGTTGGTCCTCAG
      WEHI 2 old  (115) GTGACTTGGTGTAAGCACAATGGAACAATCTGGGTACCCCTTGAAGTTGGTCCTCAG
         Bl/6 old (115) GTGACTTGGTGTAAGCACAATGGAACAATCTGTGTACCCCTTGAGGTTAGCCCTCAG
      WEHI 1old   (115) GTGACTTGGTGTAAGCACAATGGAACAATCTGGGTACCCCTTGAAGTTGGTCCTCAG
       Consensus  (115) GTGACTTGGTGTAAGCACAATGGAACAATCTGGGTACCCCTTGAAGTTGGTCCTCAG
```

Section 4

```
                  (172) 172      180       190       200       210      228
       129 SvJ    (172) CTATACACTAGTTGGGAAGAAAATCGATCAGTTCCGGTTTTTGTTCTCCATTTTAAA
    MRL/lpr (bc)  (172) CTATACACTAGTTGGGAAGAAAATCGATCAGTTCCGGTTTTTGTTCTCCATTTTAAA
        C57Bl/6   (172) CTATACACTAGTTGGGAAGAAAATCAATCAGTTCCGGTTTTTGTTCTCCACTTTAAA
         Balb/c   (172) CTATACACTAGTTGGGAAGAAAATCGATCAGTTCCGGTTTTTGTTCTCCATTTTAAA
           SWR    (172) CTATACACTAGTTGGGAAGAAAATCGATCAGTTCCGGTTTTTGTTCTCCATTTTAAA
       NZB/BinJ   (172) CTATACACTAGTTGGGAAGAAAATCGATCAGTTCCGGTTTTTGTTCTCCATTTTAAA
           NOD    (172) CTATACACTAGTTGGGAACAAAATCGATCAGTTCCGGTTTTTGTTCTCCATTTTAAA
        MRL/lpr   (172) CTATACACTAGTTGGGAAGAAAATCGATCAGTTCCGGTTTTTGTTCTCCATTTTAAA
         DBA/2J   (172) CTATACACTAGTTGGGAAGAAAATCGATCAGTTCCGGTTTTTGTTCTCCATTTTAAA
          C3H/J   (172) CTATACACTAGTTGGGAAGAAAATCGATCAGTTCCGGTTTTTGTTCTCCATTTTAAA
        129SvEv   (172) CTATACACTAGTTGGGAAGAAAATCGATCAGTTCCGGTTTTTGTTCTCCATTTAAA
          SJL.J   (172) CTATACACTAGTTGGGAAGAAAATCGATCAGTTCCGGTTTTTGTTCTCCATTTTAAA
      Celera old  (172) CTATACACTAGTTGGGAAGAAAATCGATCAGTTCCGGTTTTTGTTCTCCATTTTAAA
      WEHI 2 old  (172) CTATACACTAGTTGGGAAGAAAATCGATCAGTTCCGGTTTTTGTTCTCCATTTTAAA
         Bl/6 old (172) CTATACACTAGTTGGGAAGAAAATCAATCAGTTCCGGTTTTTGTTCTCCACTTTAAA
      WEHI 1old   (172) CTATACACTAGTTGGGAAGAAAATCGATCAGTTCCGGTTTTTGTTCTCCATTTTAAA
       Consensus  (172) CTATACACTAGTTGGGAAGAAAATCGATCAGTTCCGGTTTTTGTTCTCCATTTTAAA
```

Section 5

```
               (229) 229         240        250        260        270       285
        129 SvJ (229) CCAATACATCTCAGTGATAACGGGTCGTATAGCTGTTCTACAAACTTCAATTCTCAA
     MRL/lpr (bc)(229) CCAATACATCTCAGTGATAACGGGTCGTATAGCTGTTCTACAAACTTCAATTCTCAA
         C57Bl/6 (229) CCAATACATCTCAGTGATAATGGGTCGTATAGCTGTTCTACAAACTTCAATTCTCAA
          Balb/c (229) CCAATACATCTCAGTGATAACGGGTCGTATAGCTGTTCTACAAACTTCAATTCTCAA
            SWR (229) CCAATACATCTCAGTGATAACGGGTCGTATAGCTGTTCTACAAACTTCAATTCTCAA
        NZB/BinJ (229) CCAATACATCTCAGTGATAACGGGTCGTATAGCTGTTCTACAAACTTCAATTCTCAA
            NOD (229) CCAATACATCTCAGTGATAACGGGTCGTATAGCTGTTCTACAAACTTCAATTCTCAA
         MRL/lpr (229) CCAATACATCTCAGTGATAACGGGTCGTATAGCTGTTCTACAAACTTCAATTCTCAA
         DBA/2J (229) CCAATACATCTCAGTGATAACGGGTCGTATAGCTGTTCTACAAACTTCAATTCTCAA
          C3H/J (229) CCAATACATCTCAGTGATAACGGGTCGTATAGCTGTTCTACAAACTTCAATTCTCAA
         129SvEv (229) CCAATACATCTCAGTGATAACGGGTCGTATAGCTGTTCTACAAACTTCAATTCTCAA
           SJL.J (229) CCAATACATCTCAGTGATAACGGGTCGTATAGCTGTTCTACAAACTTCAATTCTCAA
       Celera old (229) CCAATACATCTCAGTGATAACGGGTCGTATAGCTGTTCTACAAACTTCAATTCTCAA
      WEHI 2 old (229) CCAATACATCTCAGTGATAACGGGTCGTATAGCTGTTCTACAAACTTCAATTCTCAA
         Bl/6 old (229) CCAATACATCTCAGTGATAATGGGTCGTATAGCTGTTCTACAAACTTCAATTCTCAA
      WEHI 1old (229) CCAATACATCTCAGTGATAACGGGTCGTATAGCTGTTCTACAAACTTCAATTCTCAA
      Consensus (229) CCAATACATCTCAGTGATAACGGGTCGTATAGCTGTTCTACAAACTTCAATTCTCAA
```

Section 6

```
               (286) 286         300        310      322
        129 SvJ (286) GTTATTAATAGCCATTCAGTAACCATCCATGTGAGAG
     MRL/lpr (bc)(286) GTTATTAATAGCCATTCAGTAACCATCCATGTGAGAG
         C57Bl/6 (286) GTTATTAATAGCCATTCAGTAACCATCCATGTGACAG
          Balb/c (286) GTTATTAATAGCCATTCAGTAACCATCCATGTGAGAG
            SWR (286) GTTATTAATAGCCATTCAGTAACCATCCATGTGAGAG
        NZB/BinJ (286) GTTATTAATAGCCATTCAGTAACCATCCATGTGAGAG
            NOD (286) GTTATTAATAGCCATTCAGTAACCATCCATGTGAGAG
         MRL/lpr (286) GTTATTAATAGCCATTCAGTAACCATCCATGTGAGAG
         DBA/2J (286) GTTATTAATAGCCATTCAGTAACCATCCATGTGAGAG
          C3H/J (286) GTTATTAATAGCCATTCAGTAACCATCCATGTGAGAG
         129SvEv (286) GTTATTAATAGCCATTCAGTAACCATCCATGTGAGAG
           SJL.J (286) GTTATTAATAGCCATTCAGTAACCATCCATGTGAGAG
       Celera old (286) GTTATTAATAGCCATTCAGTAACCATCCATGTGAGAG
      WEHI 2 old (286) GTTATTAATAGCCATTCAGTAACCATCCATGTGAGAG
         Bl/6 old (286) GTTATTAATAGCCATTCAGTAACCATCCATGTGACAG
      WEHI 1old (286) GTTATTAATAGCCATTCAGTAACCATCCATGTGAGAG
      Consensus (286) GTTATTAATAGCCATTCAGTAACCATCCATGTGAGAG
```

FIGURE 30

BTLA NUCLEIC ACIDS

STATEMENT OF RELATED APPLICATIONS

This application claims priority under 35 U.S.C. § 119 to U.S. Provisional Patent Application Ser. No. 60/390,653, filed Jun. 20, 2002, and to U.S. Provisional Patent Application Ser. No. 60/438,593, filed Jan. 6, 2003, the disclosures of which are expressly incorporated herein in their entirety by reference.

FIELD OF THE INVENTION

The present invention relates to immunomodulatory compositions and methods, and in particular, to novel lymphocyte regulatory molecules as well as compositions and methods exploiting the same for therapeutic, diagnostic and research purposes.

BACKGROUND OF THE INVENTION

Positive and negative costimulatory signals play critical roles in the modulation of T cell activity, and the molecules that mediate these signals have proven to be effective targets for immunomodulatory agents. Positive costimulation, in addition to T cell receptor (TCR) engagement, is required for optimal activation of naïve T cells, whereas negative costimulation is believed to be required for the acquisition of immunologic tolerance to self, as well as the termination of effector T cell functions. Upon interaction with B7.1 or B7.2 on the surface of antigen-presenting cells (APC), CD28, the prototypic T cell costimulatory molecule, emits signals that promote T cell proliferation and differentiation in response to TCR engagement, while the CD28 homologue cytotoxic T lymphocyte antigen-4 (CTLA-4) mediates inhibition of T cell proliferation and effector functions (Chambers et al., Ann. Rev. Immunol., 19:565-594, 2001; Egen et al., Nature Immunol., 3:611-618, 2002).

Several new molecules with homology to the B7 family have been discovered (Abbas et al., Nat. Med., 5:1345-6, 1999; Coyle et al., Nat. Immunol., 2: 203-9, 2001; Carreno et al., Annu. Rev. Immunol., 20: 29-53, 2002; Liang et al., Curr. Opin. Immunol., 14: 384-90, 2002), and their role in T cell activation is just beginning to be elucidated. These new costimulatory ligands include B7h, PD-L1, PD-L2, and B7-H3.

B7h (Swallow et al., Immunity, 11: 423-32, 1999), also known as B7RP-1 (Yoshinaga et al., Nature, 402: 827-32, 1999), GL50 (Ling, et al., J. Immunol., 164:1653-7, 2000), B7H2 (Wang et al., Blood, 96: 2808-13, 2000), and LICOS (Brodie et al., Curr. Biol., 10: 333-6, 2000), binds to inducible costimulator (ICOS) on activated T cells, and costimulates T cell proliferation and production of cytokines such as interleukin 4 (IL-4) and IL-10.

PD-L1 (Freeman et al., J. Exp. Med., 192: 1027-34, 2000), also known as B7-H1 in humans (Dong et al., Nat. Med., 5, 1365-9, 1999), and PD-L2 (Latchman et al., Nat. Immunol., 2: 261-8, 2001), also known as B7-DC (Tseng et al., J. Exp. Med., 193, 839-46, 2001) bind to programmed death 1 (PD-1) receptor on T and B cells, although at present the function of these interactions is controversial. Some reports have demonstrated that PD-L1 and PD-L2 have inhibitory effects on T cell responses (Freeman et al., J. Exp. Med., 192: 1027-34, 2000; Latchman et al., Nat. Immunol., 2: 261-8, 2001), while others have shown that both ligands (B7-H1 and B7-DC) positively regulate T cell proliferation and specifically enhance IL-10 or interferon gamma (IFN-γ) production (Dong et al., Nat. Med., 5, 1365-9, 1999; Tseng et al., J. Exp. Med., 193, 839-46, 2001).

Finally, B7-H3, another newly identified B7 homologue, binds an as yet currently unknown counter-receptor on activated T cells, and is reported to enhance proliferation of CD4+ T helper (Th) cells and CD8+ cytotoxic T lymphocytes (CTLs or Tcs) and selectively enhance IFN-γ expression (Chapoval et al., Nat. Immunol., 2, 269-74, 2001; Sun et al., J. Immunol., 168, 6294-7, 2002).

With the exception of PD1 ligands, which show some expression on non-lymphoid tissues, the expression of known B7 family members is largely restricted to lymphoid cells. Collectively, these studies have revealed that B7 family members are ligands on lymphoid cells that interact with cognate receptors on lymphocytes to provide positive or negative costimulatory signals that play critical roles in the regulation of cell-mediated immune responses.

The identification of additional molecules that have T cell costimulatory activity is of keen interest due to their fundamental biological importance and the therapeutic potential of agents capable of affecting their activity. Agents capable of modulating costimulatory signals, and thereby capable of modulating the activation and/or effector functions of CD8+ CTLs and CD4+ Th cells find use in the modulation of immune responses, and are highly desirable.

In particular, many autoimmune disorders are known to involve autoreactive T cells and autoantibodies. Agents that are capable of inhibiting or eliminating autoreactive lymphocytes without compromising the immune system's ability to defend against pathogens are highly desirable.

Conversely, many cancer immunotherapies, such as adoptive immunotherapy, expand tumor-specific T cell populations and direct them to attack and kill tumor cells (Dudley et al., Science 298:850-854, 2002; Pardoll, Nature Biotech., 20:1207-1208, 2002; Egen et al., Nature Immunol., 3:611-618, 2002). Agents capable of augmenting tumor attack are highly desirable.

In addition, immune responses to many different antigens (e.g., microbial antigens or tumor antigens), while detectable, are frequently of insufficient magnitude to afford protection against a disease process mediated by agents (e.g., infectious microorganisms or tumor cells) expressing those antigens. It is often desirable to administer to the subject, in conjunction with the antigen, an adjuvant that serves to enhance the immune response to the antigen in the subject.

It is also desirable to inhibit normal immune responses to antigen under certain circumstances. For example, the suppression of normal immune responses in a patient receiving a transplant is desirable, and agents that exhibit such immunosuppressive activity are highly desirable.

Costimulatory signals, particularly positive costimulatory signals, also play a role in the modulation of B cell activity. For example, B cell activation and the survival of germinal center B cells require T cell-derived signals in addition to stimulation by antigen. CD40 ligand present on the surface of helper T cells interacts with CD40 on the surface of B cells, and mediates many such T-cell dependent effects in B cells. Interestingly, negative costimulatory receptors analogous to CTLA-4 have not been identified on B cells. This suggests fundamental differences may exist in the way T cells and B cells are induced to respond to antigen, which has implications for mechanisms of self-tolerance as well as the inhibition of B cell effector functions, such as antibody production. Were a functional CTLA-like molecule to be found on B cells, the finding would dramatically shift our understanding of the mechanisms of B cell stimulation.

Further, the identification of such receptors could provide for the development of novel therapeutic agents capable of modulating B cell activation and antibody production, and useful in the modulation of immunologic responses.

SUMMARY OF THE INVENTION

In accordance with the foregoing objectives, the present invention provides a novel receptor expressed in both B and T lymphocytes as well as a newly-characterized ligand thereof having a previously-unknown function. The novel receptor of the present invention is denominated "B and T lymphocyte attenuator" (BTLA), and is distinct from CD28, CTLA-4, ICOS and PD-1, while the novel ligand provided herein is B7x, a new member of the B7 family. Methods and compositions for modulating BTLA-mediated lymphocyte signaling such as, e.g., modulating the natural interaction of BTLA and B7x are also provided, having multiple therapeutic applications for immunological tolerance, autoimmunity, immunosuppression, and immunotherapy including cancer immuhotherapy.

As disclosed for the first time herein, BTLA acts a negative regulator of both B and T lymphocyte activity, wherein signaling mediated by BTLA results in the inhibition of BTLA-positive lymphocyte activity. In BTLA-positive T cells BTLA signaling can inhibit TCR-induced T cell responses, such as cell cycle progression, differentiation, survival, cytokine production and cytolytic activation, while in BTLA-positive B cells BTLA signaling can inhibit B cell antigen receptor-induced B cell responses, such as cell cycle progression, differentiation, survival, antigen presentation and antibody production.

Also disclosed for the first time herein is the identification of the new B7 family member B7x as a ligand for BTLA, as well as the previously unrecognized ability of B7x to negatively regulate B and T lymphocyte activity through its interaction with BTLA. The interaction of B7x with BTLA inhibits both B and T cell responses, and is a means by which B7x-positive tumor tissue inhibits the activity of tumor-specific T cells. Further, the present disclosure establishes that B7x is also expressed on non-tumor non-lymphoid tissue, thus identifying the B7x/BTLA interaction as a mechanism for maintaining immunological tolerance. These novel findings enable the use of therapeutic agents capable of interfering with the interaction of BTLA and B7x to modulate lymphocyte activity for the purpose of treating, among other conditions, cancer and autoimmune diseases.

In accordance with these observations, in one aspect, the present invention provides nucleic acid sequences encoding BTLA proteins, and proteins so encoded, which find use in the modulation of B and T lymphocyte activity and in the treatment of cancer and autoimmune disease. In a further aspect, the present invention provides nucleic acid sequences encoding B7x proteins, and B7x proteins so encoded, also finding use in the modulation of B and T lymphocyte activity and in the treatment of cancer and autoimmune disease. Also provided are derivatives of the BTLA and B7x nucleotides and polypeptides of the present invention.

In a further aspect, the invention provides a variety of bioactive agents capable of modulating BTLA signaling and lymphocyte activation. In preferred embodiments, such bioactive agents are capable of modulating the interaction of BTLA and B7x. Suitable bioactive agents include antibodies capable of specifically binding to BTLA or B7x polypeptides (e.g., monoclonal, polyclonal, single chain, and/or bispecific antiobodies as well as Fab and F(ab)$_2$ fragments, variants and derivatives thereof), soluble and membrane-bound BTLA and B7x proteins and polypeptides including fragments and truncated forms thereof, BTLA and B7x fusion proteins, antisense oligonucleotides directed to the BTLA and/or B7x nucleotides disclosed herein, small molecular weight molecules, expression vectors comprising all or a part of the BTLA and/or B7x polynucleotides, inhibitory RNA sequences, and the like.

In one embodiment, antagonists of BTLA signaling are provided for increasing B and T cell activation. In a preferred embodiment, such antagonists comprise blocking agents capable of interfering with the natural interaction of B7x and BTLA, thereby inhibiting BTLA-mediated negative signaling and resulting in an increase in lymphocyte activation and proliferation and effector function.

In an alternative embodiment, agonists of BTLA signaling are provided for inhibiting T and B cell activation. In a preferred embodiment, such bioactive agents comprise mimicking agents capable of binding to BTLA and mimicking and/or augmenting the natural interaction of B7x with BTLA, thereby resulting in inhibition of T and B cell activation and proliferation and effector function.

In a preferred embodiment, the invention provides antibodies that specifically bind to naturally occurring human BTLA and/or murine BTLA proteins, and in particular, to one or more epitopes present in the extracellular domains of BTLA proteins as disclosed herein.

In another preferred embodiment, the invention provides antibodies that specifically bind to naturally occurring human B7x and/or murine B7x proteins, and in particular, to one or more epitopes present in the extracellular domains of B7x proteins as disclosed herein.

In another preferred embodiment, the invention provides B7x fusion proteins that are capable of binding to BTLA and mimicking the natural interaction of B7x and BTLA. In an especially preferred embodiment, the fusion protein comprises all or a portion of the extracellular domain of B7x as disclosed herein coupled with, e.g., an Fc region of an immunoglobulin.

In yet another preferred embodiment, the invention provides BTLA fusion proteins that are capable of binding to B7x and blocking the natural interaction of B7x and BTLA. In an especially preferred embodiment, the fusion protein comprises all or a portion of the extracellular domain of BTLA as disclosed herein coupled with, e.g., an Fc region of an immunoglobulin.

In another aspect, methods for modulating lymphocyte activity are provided comprising contacting a B and/or T lymphocyte with a bioactive agent capable of modulating BTLA activity. In one embodiment, the bioactive agent comprises an antagonist of BTLA activity such as, e.g., a BTLA or B7x blocking agent, resulting in an upregulation or increase in lymphocyte activity by preventing negative BTLA-mediated signaling. In an alternative embodiment, the bioactive agent comprises an agonist of BTLA activity such as, e.g., a BTLA or a B7x mimicking agent, resulting in downregulation of lymphocyte activity by replacing or augmenting BTLA-mediated negative signaling.

In a further aspect, methods for modulating lymphocyte activity are provided comprising contacting a B and/or T lymphocyte with a bioactive agent capable of modulating the interaction of BTLA with B7x. In one embodiment, a bioactive agent capable of interfering with the natural interaction of BTLA and B7x is employed to increase lymphocyte activity and proliferation such as, e.g., a B7x or a BTLA blocking agent. In an alternative embodiment, a bioactive agent capable augmenting or replacing the natural interaction of BTLA and B7x is employed to inhibit lymphocyte activity and proliferation such as, e.g., a B7x or BTLA mimicking agent.

Suitable BTLA blocking agents may be selected from the group comprising or consisting of soluble BTLA polypeptides and fusion proteins, anti-BTLA antibodies capable of binding to at least a portion of the extracellular domain of BTLA and interfering with BTLA-mediated signaling, small molecule inhibitors of BTLA receptor interaction with its ligands, and the like. Alternative BTLA antagonists further include antisense oligonucleotides directed to the BTLA nucleic acid sequence, inhibitory RNA sequences, small molecule inhibitors of BTLA expression and/or intracellular signaling, and the like.

Similarly, suitable B7x blocking agents may be selected from the group comprising or consisting of anti-B7x antibodies capable of binding to at least a portion of the extracellular domain of B7x and interfering with the interaction of B7x and BTLA, small molecule inhibitors of the interaction between B7x and BTLA, soluble B7x polypeptides and fusion proteins having modified B7x amino acid sequences so as to interfere with the interaction of B7x and BTLA and incapable of activating BTLA-mediated signaling, and the like. Alternative B7x antagonists include antisense olignucleotides directed to the B7x nucleic acid sequence, inhibitory RNA molecules, small molecule inhibitors of B7x expression, and the like.

Suitable BTLA mimicking agents may be selected from the group comprising or consisting of function-activating anti-BTLA antibodies capable of binding to at least a portion of the extracellular domain of BTLA and stimulating BTLA-mediated signaling, gene therapy vectors capable of recombinantly producing functional BTLA molecules intracellularly, small molecule enhancers of BTLA expression and/or BTLA-mediated signaling, and the like. Similarly, suitable B7x mimicking agents may be selected from the group comprising or consisting of soluble B7x polypeptides and fusion proteins capable of activating BTLA-mediated signaling, small molecule enhancers of the interaction between B7x and BTLA as well as enhancers of B7x expression, gene therapy vectors capable of recombinantly producing functional B7x molecules intracellularly, and the like.

Thus, in a more specific embodiment methods for stimulating, augmenting and/or increasing lymphocyte activity are provided comprising contacting a B or T lymphocyte with an antagonist of BTLA-mediated signaling, said antagonist comprising at least one bioactive agent selected from the group consisting of soluble BTLA polypeptides, soluble BTLA fusion proteins, anti-BTLA antibodies capable of binding to at least a portion of the extracellular domain of BTLA and interfering with BTLA-mediated signaling, small molecule inhibitors of BTLA expression and/or BTLA-mediated signaling, anti-B7x antibodies capable of binding to at least a portion of the extracellular domain of B7x and interfering with the interaction of B7x and BTLA, small molecule inhibitors of the interaction between B7x and BTLA, soluble B7x polypeptides and B7x fusion proteins incapable of activating BTLA-mediated signaling, and interfering RNA sequences.

In a particularly preferred embodiment, methods for increasing a host immune response to antigenic stimulation are provided, comprising the administration to the host of at least one of the aforementioned antagonists of BTLA-mediated signaling. Desirably, the antigenic stimulation may be from pathogen antigens, vaccine antigens and/or tumor antigens.

In a specific embodiment, methods for stimulating a cellular immune response against tumor antigens other than B7x are provided, comprising administering to a cancer patient at least one of the subject antagonists or blocking agents to inhibit BTLA-mediated negative signaling and thereby increase the T cell response directed against tumor antigens other than B7x present in the cancerous tissue.

In a further specific embodiment methods for inhibiting, attenuating and/or decreasing lymphocyte activity are provided comprising contacting a B or T lymphocyte with an agonist of BTLA-mediated signaling, said agonist selected from the group consisting of soluble B7x polypeptides and B7x fusion proteins capable of activating BTLA-mediated signaling, function-activating anti-BTLA antibodies capable of binding to at least a portion of the extracellular domain of BTLA and stimulating BTLA-mediated signaling, gene therapy vectors capable of recombinantly producing functional BTLA molecules intracellularly, small molecule enhancers of BTLA expression and/or BTLA-mediated signaling, small molecule enhancers of the interaction between B7x and BTLA, small molecule enhancers of B7x expression, and gene therapy vectors capable of recombinantly producing functional B7x molecules intracellularly.

In a particularly preferred embodiment, methods for suppressing a host immune response to antigenic stimulation are provided, comprising the administration to the host of at least one of the aforementioned agonists of BTLA-mediated signaling. Desirably, the antigenic stimulation may be from self antigens in the context of autoimmune disease, or from donor antigens present in transplanted organs and tissues.

In an alternative aspect, the present invention provides bioactive agents and methods for modulating the interaction of a B7x-expressing cell and a BTLA-expressing lymphocyte. In a preferred embodiment, bioactive agents and methods for interfering with the interaction of B7x-positive tumor cells with T cells are provided, resulting in inhibition of negative BTLA-mediated signaling. In an especially preferred embodiment, the T cell is a CD4+ cell or a CD8+ cell. In a further embodiment, the CD4+ T cell is a Th1 cell.

In another preferred embodiment, bioactive agents and methods for mimicking or enhancing the interaction of B7x-positive non-tumor non-lymphoid cells with BTLA-positive T cells are provided, thereby decreasing T cell activity. In an especially preferred embodiment, the T cell is a CD4+ T cell or a CD8+ T cell. In a further embodiment, the CD4+ T cell is a Th1 cell.

In a further aspect, methods for treating cancers characterized by the presence of B7x-expressing tumor cells are provided. In one embodiment, these methods comprise administering to a mammalian subject at least one of the antagonists of BTLA-mediated signaling disclosed herein, either alone or in conjunction with alternative cancer immunotherapy, chemotherapy and/or radiotherapy protocols. In a preferred embodiment, at least one BTLA or B7x blocking agent is administered to a subject having B7x-positive tumor cells, wherein said blocking agent is capable of interfering with the interaction of BTLA and B7x and inhibiting BTLA-mediated signaling. Preferably, administration of said blocking agents is effective to increase T cell activity directed against tumor antigens other than B7x on the tumor cells, and in particular, to increase cytotoxic T cell activity. Still more preferably, administration of the subject antagonists is effective to inhibit the growth of the B7x-expressing tumor cells.

It is also contemplated that the subject BTLA and/or B7x blockade provided herein will find synergistic combination with CTLA-4 blockade as described in U.S. Pat. Nos.

5,855,887; 5,811,097; and 6,051,227, and International Publication WO 00/32231, the disclosures of which are expressly incorporated herein by reference.

In a further aspect, methods for treating autoimmune disorders characterized by the absent or aberrant expression of B7x in non-tumor non-lymphoid host cells subjected to autoimmune attack are provided. In one embodiment, these methods comprise administering to a mammalian subject at least one of the agonists of BTLA-mediated signaling disclosed herein, either alone or in conjunction with alternative immunotherapy and/or immunosuppressive protocols. In a preferred embodiment, at least one BTLA or B7x mimicking agent is administered to a subject having autoreactive BTLA-positive lymphocytes, wherein said mimicking agent is capable of replacing and/or augmenting the interaction of BTLA and B7x and replacing or increasing BTLA-mediated signaling. Preferably, administration of said mimicking agents is effective to decrease autoreactive lymphocyte activity directed against non-tumor non-lymphoid host cells, and particularly autoreactive CD8+ CTL and CD4+ Th1 activity, and B cell activity.

In a still further aspect, methods for improving the outcome of organ and tissue transplantation and prolonging graft survival are provided. In one embodiment, these methods comprise administering to a transplant recipient at least one of the agonists of BTLA-mediated signaling disclosed herein, either alone or in conjunction with alternative immunotherapy and/or immunosuppressive protocols. In a preferred embodiment, at least one BTLA or B7x mimicking agent is administered to the transplant recipient, wherein said mimicking agent is capable of replacing and/or augmenting the interaction of BTLA and B7x and replacing or increasing BTLA-mediated signaling. Preferably, administration of said mimicking agents is effective to decrease the recipient immune response against donor antigens present in the graft, particularly the cytolytic CTL response and the B cell response. Still more preferably, administration of the subject mimicking agents is effective to bias to T helper cell response from an unfavorable Th-1 type response to a more favorable Th-2 type response, as described in more detail herein.

Also provided are adjuvant compositions comprising at least one of the above-described BTLA and/or B7x blocking agents as well as other antagonists of BTLA-mediated signaling.

Also provided are immunosuppressant compositions comprising at least one of the above-described BTLA and/or B7x mimicking agents as well as other agonists of BTLA-mediated signaling.

In an alternative aspect, the present invention provides methods of screening for bioactive agents that are useful for modulating T cell activation. Bioactive agents identified by the screening methods provided herein may be used to react with B7x-expressing cells or BTLA-expressing cells in order to interfere with the interaction between BTLA-expressing B and/or T cells and B7x-expressing non-lymphoid cells, and thereby antagonize the function of the BTLA/B7x interaction. Alternatively, bioactive agents may be used to react with B7x-expressing cells or BTLA-expressing cells in order to mimic the B7x/BTLA interaction, effecting T cell inhibition in the absence of a BTLA/B7x interaction. Alternatively, bioactive agents may be used to modify the natural BTLA/B7x interaction in some way, for example, to increase the association and augment the inhibitory signal.

In an alternative aspect, the invention provides expression vectors comprising the isolated BTLA and/or B7x nucleic acid sequences disclosed herein, recombinant host cells comprising the recombinant nucleic acid molecules disclosed herein, and methods for producing BTLA and/or B7x polypeptides comprising culturing the host cells and optionally isolating the polypeptide produced thereby.

In a further aspect, transgenic non-human mammals are provided comprising a nucleic acid encoding a BTLA and/or B7x protein as disclosed herein. The BTLA or B7x nucleotides are introduced into the animal in a manner that allows for increased expression of levels of a BTLA or B7x polypeptide, which may include increased circulating levels. Alternatively, the BTLA or B7x nucleic acid fragments may be used to target endogenous BTLA or B7x alleles in order to prevent expression of endogenous BTLA or B7x nucleic acids (i.e. generates a transgenic animal possessing a BTLA or B7x protein gene knockout). The transgenic animal is preferably a mammal, and more preferably a rodent, such as a rat or a mouse.

BRIEF DESCRIPTION OF THE DRAWINGS

FIG. 1 shows the amino acid sequences of mouse B7x protein (SEQ ID NO: 1) and human B7x protein (SEQ ID NO: 2).

FIG. 2 shows the nucleotide sequence of mouse B7x nucleic acid (SEQ ID NO:3) encoding mouse B7x protein.

FIG. 3 shows the nucleotide sequence of human B7x nucleic acid (SEQ ID NO:4) encoding human B7x protein.

FIG. 4 shows amino acid sequence alignment of B7x with other mouse B7 family members obtained using the ClustalW with BLOSUM Series of MacVector 7.0. Conserved cysteine residues are marked with an asterisk. Identical amino acids are highlighted in black and similar residues in gray shading (SEQ ID NOS:57-62).

FIGS. 13A and 13B show T cells purified from wildtype and BTLA −/− mice that are stained with B7xIg fusion protein or B7hIg fusion protein as indicated.

FIG. 17 is a series of plots showing flow cytometry analysis of CD4+ T cells. Cells were labeled with CSFE and stimulated with or without plate-bound anti-CD3 (0.25 mg/ml) and CHO transfectants expressing GFP or B7x. Percentages refer to fraction of cells in the non-dividing peak or divided more than two times.

FIG. 18 is a series of plots showing flow cytometry analysis flow cytometry analysis of CD8+ T cells. Cells were labeled with CSFE and stimulated with or without plate-bound anti-CD3 (0.25 mg/ml) and CHO transfectants expressing GFP or B7x. Percentages refer to fraction of cells in the non-dividing peak or divided more than two times.

FIG. 19 shows the amino acid sequences of a mouse BTLA protein (SEQ ID NO: 5) and a human BTLA protein (SEQ ID NO: 6). The mouse and human sequences are aligned, and spaces are shown as (•) for optimal comparison. The signal peptide and the transmembrane region are underlined. Potential N-linked glycosylation sites (−) and cysteine residues (•) predicted to participate in Ig domain disulfide bonding are indicated with markings above the residues. The conserved sequences around putative tyrosine-based signaling motifs are boxed.

(a) FACScalibur analysis of BJAB cells infected with myc-tagged BTLA, Δcyt BTLA, BTLAs and empty vector, and stained with anti-myc mAb.

(b) Anti-myc Western blot. BJAB cells were infected with myc-tagged mouse BTLA or myc-tagged human BTLA, lysed, and anti-myc immunoprecipitates were treated with peptide N-glycosidase F, where indicated.

(c) Anti-phosphotyrosine Western blot. BJAB cells infected with myc-tagged BTLA (WT) or single tyrosine mutant myc-tagged BTLA (Y226F, Y257F, Y282F) were incubated in the absence or presence of pervanadate ($VO_4$), BTLA proteins were immunoprecipitated with anti-myc, and immunoprecipitates were probed with anti-phosphotyrosine.

(d) Anti-phosphotyrosine Western blot. BJAB cells infected with myc-tagged BTLA (WT) or with double or triple tyrosine mutant myc-tagged BTLA (as indicated) were incubated in the absence or presence of pervanadate ($VO_4$), BTLA proteins were immunoprecipitated with anti-myc, and immunoprecipitates were probed with anti-phosphotyrosine.

Figure 24:
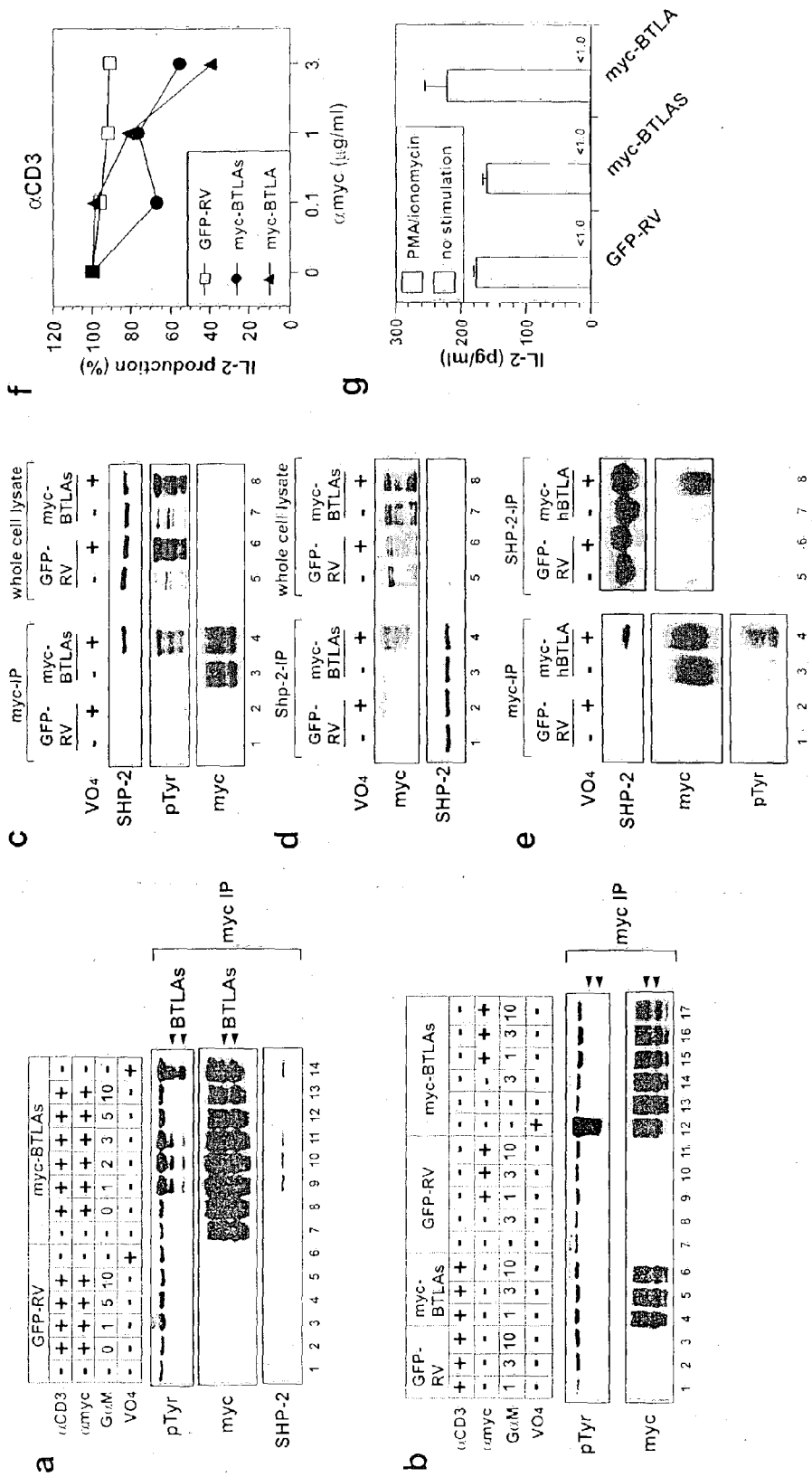

FIG. 24 Inducible association of BTLA with SHP-2.

(a) Anti-phosphotyrosine and anti-SHP-2 Western blots. DO11.10 cells with empty vector (GFP-RV), or expressing BTLAs with extracellular myc epitope (myc-BTLAs). Cells were incubated with anti-CD3, anti-myc, or pervanadate as indicated. Cells were treated with goat anti-mouse IgG (GαM) for indicated time. Anti-myc immunoprecipitate was probed with anti-phosphotyrosine and anti-SHP-2 antibody.

(b) Anti-phosphotyrosine Western blot. Cells and treatment as described in (a) and indicated.

(c) Anti-phosphotyrosine, anti-SHP-1 and anti-SHP-2 Western blots. Cells as described in (a), incubated in the absence (−) or presence (+) of pervanadate. Anti-myc immunoprecipitates and whole cell lysates probed with anti-phosphotyrosine, anti-SHP-1, and anti-SHP-2 antibodies.

(d) Anti-myc and anti-SHP-2 Western blots. Cells as described in (a), incubated in the absence (−) or presence (+) of pervanadate. Anti-SHP-2 immunoprecipitates and whole cell lysates probed with anti-myc and anti-SHP-2 antibodies.

(e) Anti-myc, anti-SHP-2 and anti-phosphotyrosine Western blots. Jurkat T cells with GFP-RV, or expressing a full length human BTLA containing an N-terminal myc epitope. Cells were treated with pervanadate as indicated. Anti-myc and anti-SHP-2 immunoprecipitates were probed with anti-myc, anti-SHP-2 and anti-phosphotyrosine.

(f) DO11.10 cells expressing control vector (GFP-RV), myc-BTLAs (short isoform), or myc-BTLA were stimulated with anti-CD3 plus the indicated amounts of anti-myc, and IL-2 production was determined by ELISA.

(g) DO11.10 cells expressing control vector (GFP-RV), myc-BTLAs (short isoform), or myc-BTLA were stimulated with PMA plus ionomycin as indicated.

FIG. 25

(a) The scheme used to generate BTLA −/− mice.

(b) Southern blot. BglII-digested tail DNA hybridized with probe B.

(c) Northern blot. RNA from splenocytes probed with full length mouse BTLA cDNA probe, and GAPDH probe for control.

(d) Th1 proliferation assay. Resting Th1 cells from DO11.10+/BTLA+/+ (+/+) or DO11.10+/BTLA-/-(-/-) mice were incubated with CD8+ or CD8- DCs with or without OVA323-339 peptide, and [³H] thymidine incorporation was measured.

Figure 26:
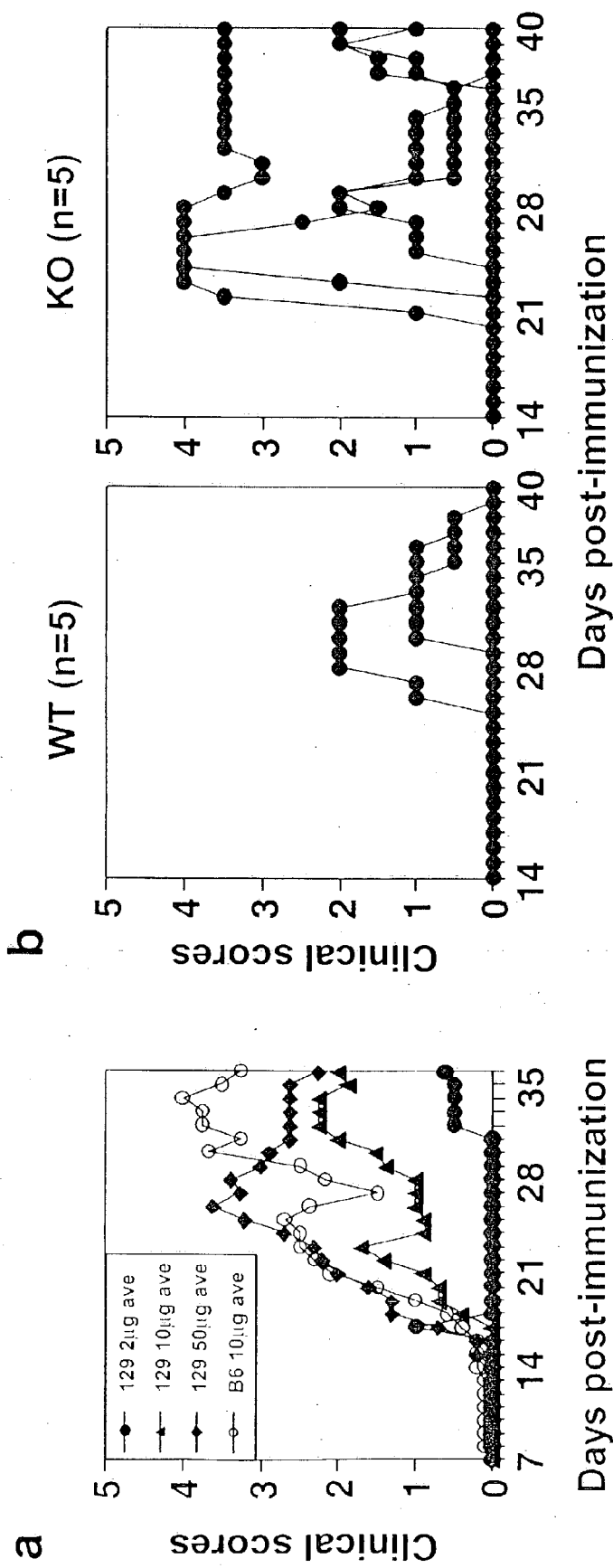

FIG. 26: Increased EAE susceptibility in BTLA-/- mice.

(a) Clinical scoring of WT mice injected with 2 µg, 10 µg, and 50 µg in incomplete Freund's adjuvant. Clinical scores: score 0, normal mouse, no overt signs of disease; 1, limp tail or hind limb weakness, but not both; 2, limp tail or hind limb weakness; 3, partial hind limb paralysis; 4, complete hind limb paralysis; 5, moribund state, death by EAE, sacrifice for humane reasons).

(b) Clinical scoring of WT and BTLA -/- mice injected with suboptimal dose (2 µg) of MOG peptide.

Figure 27:
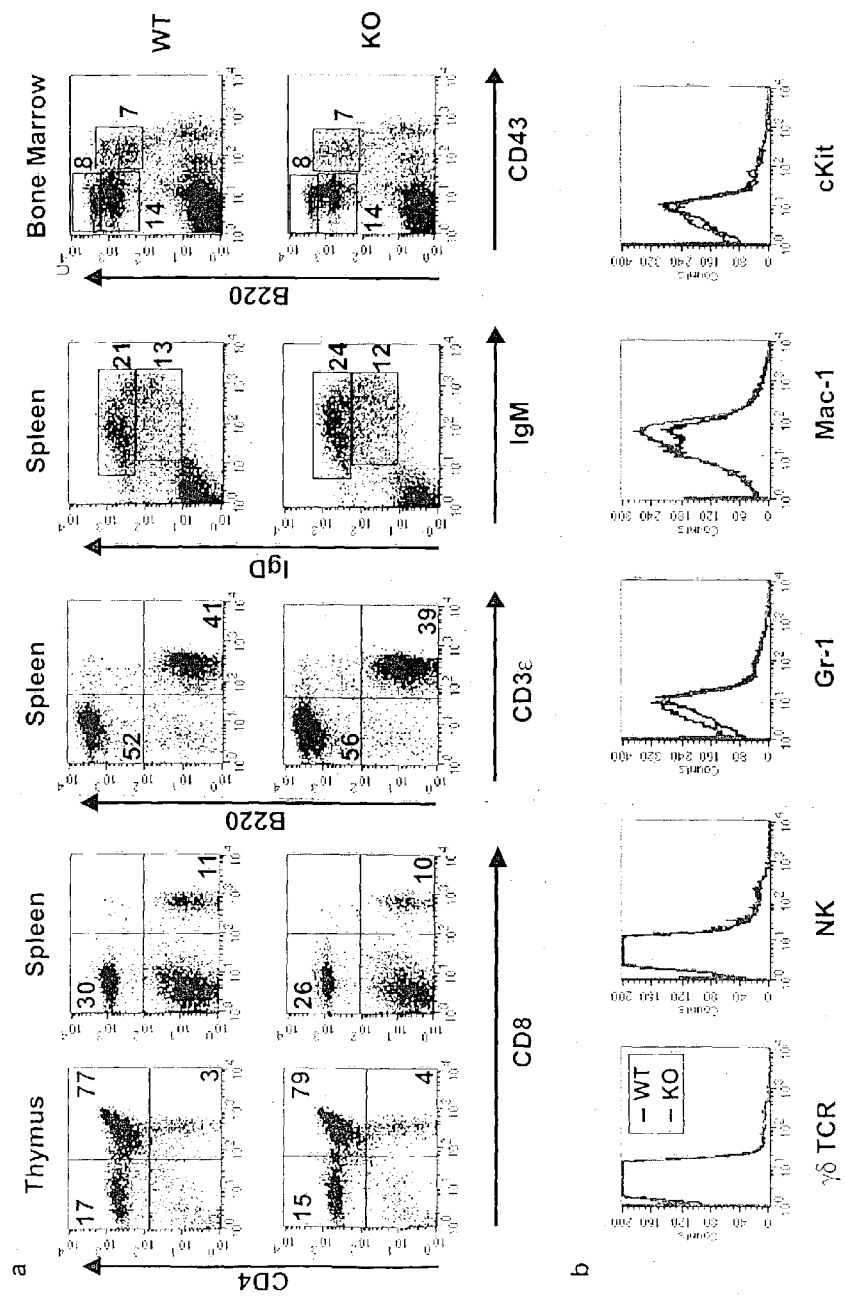

FIG. 27: Normal lymphocyte development in BTLA-/- mice (a) FACS analysis of thymus, spleen and bone marrow cells from BTLA+/+ and BTLA-/- littermates stained with CD4-PE, CD8-FITC, CD3ε-biotin/SA-Cychrome, B220-PE, αIgM-biotin/SA-Cychrome, αIgD-FITC and CD43-FITC.

(b) FACS analysis of splenocytes stained γδ-TCR-FITC, DX5-FITC (pan NK), Gr-1-biotin/SA-Cychrome, Mac-1-biotin/SA-Cychrome, and anti-cKit-biotin/SA-Cychrome. Histograms overlayed for each marker (black line; +/+, red line; -/-).

(c) Thymocytes and splenocytes from 8 weeks old BTLA+/+ and BTLA-/- littermates were counted by trypan-blue dye exclusion. The data are presented as the mean ±SD of five mice.

FIG. 28 shows the sequences of human BTLA nucleic acid (SEQ ID NO:7) and encoded human BTLA protein (SEQ ID NO:8). The nucleic acid and amino acid sequences are found at Genbank accession numbers AY293286.1 and AAP44003.1, respectively.

FIG. 29 shows the sequences of mouse BTLA nucleic acid (SEQ ID NO:9) and encoded mouse BTLA protein (SEQ ID NO:10). The nucleic acid and amino acid sequences are found at Genbank accession numbers AY293285.1 and AAP44002.1, respectively.

FIG. 30 shows the BTLA allelic variation between a number of mouse strains (SEQ ID NOS: 11-27).

Figure 31:
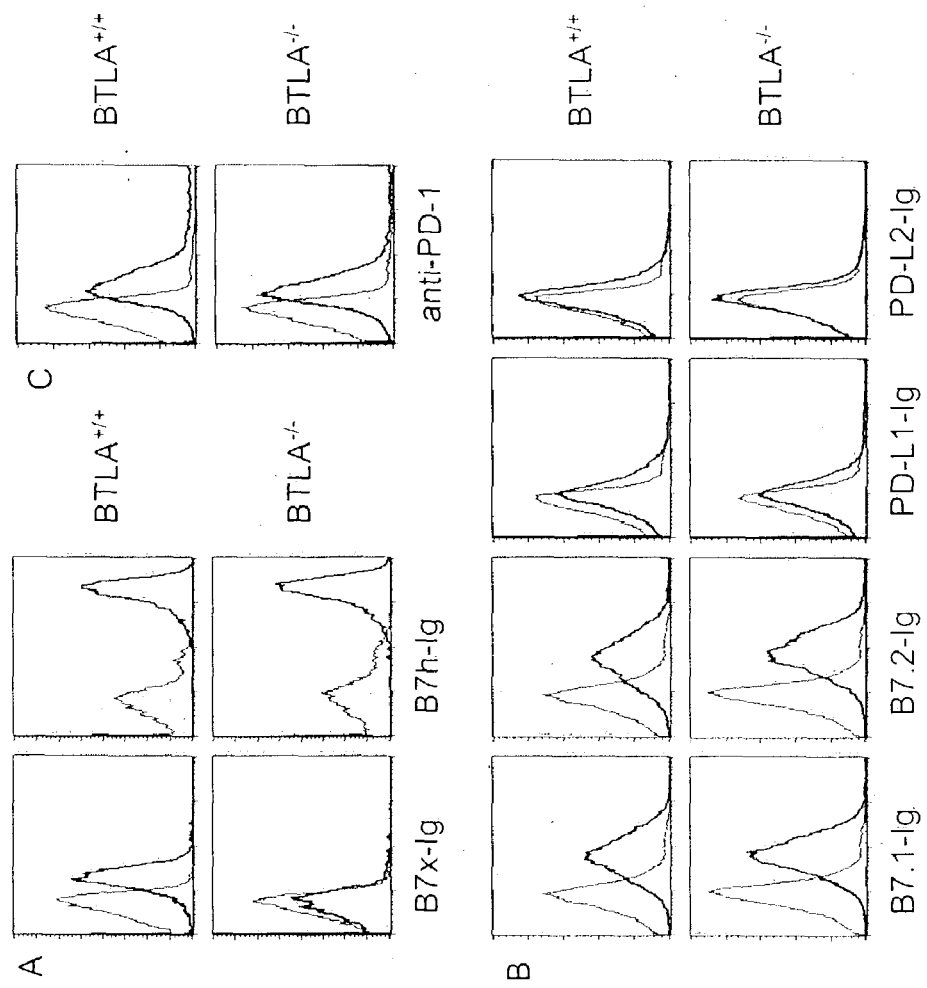

FIG. 31: BTLA interacts with an orphan B7, B7x. (a) Spleen and lymph node cells from BTLA wild-type and BTLA-deficient DO11.10+ TCR transgenic mice were collected and stimulated with 0.3 µM OVA peptide, 10 U/ml of IL-12 and neutralizing antibodies to IL-4, and assayed for Ig fusion binding after 4 d. Cells were stained with anti-CD4-FITC. Left, cells were stained with a human IgG1 antibody as a negative control (filled) or with a B7x-Ig fusion protein (open), followed by goat anti-human IgG-PE. Right, cells were unstained (filled) or stained with B7h-Ig (open), followed by biotinylated anti-Myc (murine IgG1 isotype) and streptavidin-PE. Anti-Myc was used as a negative control for the B7h-Ig fusion protein. (b,c) TH1 cell lines derived from BTLA wild-type and BTLA-deficient DO11.10+ mice were stimulated as above, collected on day 3, and assayed for binding to Ig fusion proteins. All cells were stained with anti-CD4-FITC. In b, Cells were stained with a human IgG1 antibody (filled) or with B7.1-Ig, B7.2-Ig, PD-L1-Ig and PD-L2-Ig fusion proteins (open), followed by goat anti-human Fcγ F(ab)2-PE. In c, Cells were stained with a hamster IgG2-PE as a negative control (filled) or with anti-PD-1-PE. Histograms are gated on CD4+ cells.

Figure 32:
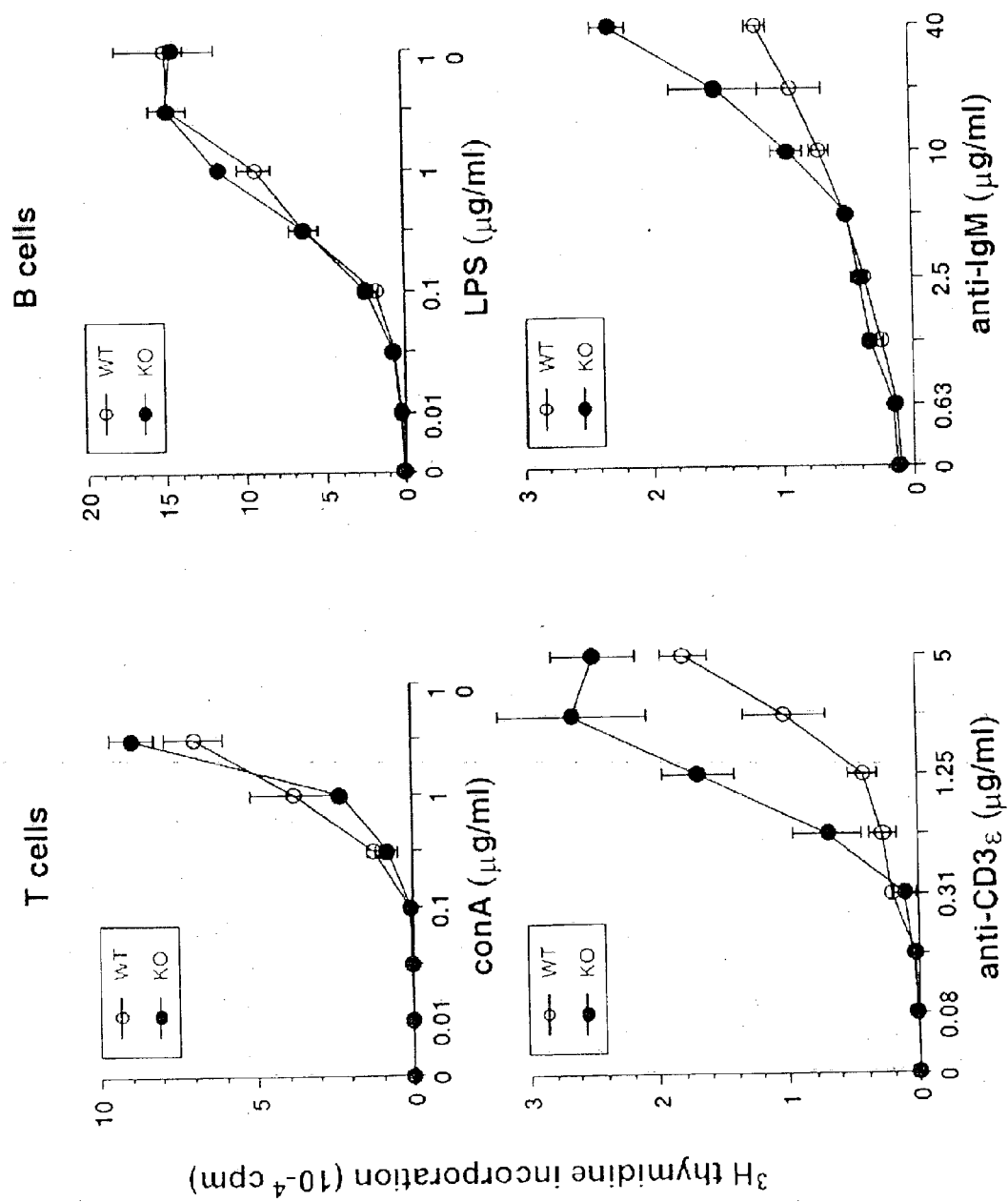

FIG. 32: In vitro responses of BTLA-deficient lymphocytes. T and B cell from wild-type (WT) or BTLA-deficient (KO) mice were purified by cell sorting using anti-CD4-FITC, anti-CD8α-FITC or anti-B220-PE. Cells were stimulated with the indicated final concentrations of plate-bound anti-IgM, LPS, concanavalin A or plate-bound anti-CD3e. Cell proliferation was measured by pulsing with [³H]thymidine for 16 h.

DETAILED DESCRIPTION OF THE PREFERRED EMBODIMENTS

The present invention is directed to the identification and characterization of BTLA, a novel down-regulatory lymphocytic receptor. As shown herein, BTLA is expressed in both B and T cells and exhibits dynamic expression, with very low expression levels in naïve B and T cells, rapid induction upon stimulation of cells with antigen, and increased expression in activated B and T cells. Moreover, there is a high level of BTLA expression in Th1 cells and a much lower level in Th2 cells following Th polarization. The present invention further demonstrates that stimulation of BTLA (e.g., via the interaction of B7x and BTLA) inhibits T cell activity, and that loss of BTLA function leads to T cell hyperactivation. Thus, as disclosed herein, BTLA represents a novel negative regulatory receptor for both B and T lymphocytes, and plays a role in controlling inflammatory responses and autoimmunity.

The present invention is also directed to the characterization of B7x, a new member of the B7 family the expression of which is not limited to lymphoid tissue. As shown herein, B7x is expressed in cells of non-hematopoietic origin, as well as in cells of the hematopoietic lineage, and is highly expressed in a variety of tumor cells. The present invention further demonstrates for the first time that B7x is capable of inhibiting immune-responses, and in particular, both B and T cell responses, via its interaction with BTLA. The present invention further identifies the role of B7x in the maintenance of immunological self-tolerance and the inhibition of autoimmunity. The present invention also identifies the role of B7x in promoting the survival of tumor cells by inhibiting T cell activation.

Aberrant BTLA activity, for example, as a result of aberrant BTLA/B7x interaction or aberrant BTLA or B7x expression, can-promote diseases associated with T cell activity. As noted above, a high level of B7x expression on tumor cells facilitates the inhibition of T cell activation by tumor cells, and tumor cell survival. Conversely, a low level of B7x expression on non-lymphoid tissue can render the tissue susceptible to attack by autoreactive T and B cells, and predisposes a subject to autoimmune disease. Similarly, an increased level of BTLA expression in lymphocytes, or increased effective activity, can sensitize lymphocytes to inhibitory costimulation, making them less responsive to antigen, suppressing the immune system, and potentiating the growth of tumor tissue. Conversely, a decreased level of BTLA expression in lymphocytes, or decreased effective activity, can make lymphocytes refractive to particular inhibitory costimulation signals, such as those of B7x, and lead to a hyperimmune state characterized by a predisposition to autoimmune disease.

In accordance with the foregoing, the present invention provides methods and compositions for modulating immune responses.

As used herein, the term "immune response" includes both T and/or B cell responses, i.e., cellular and/or humoral immune responses. In one embodiment, the compositions and methods disclosed herein can be used to reduce or enhance helper T cell (Th) responses, and more preferably, Th1 cell responses. In another embodiment, the compositions and methods disclosed herein can be used to reduce or, enhance cytotoxic T cell (Tc) responses. The claimed methods can be used to reduce or enhance both primary and secondary immune responses and effector function (e.g., cytolytic activity, cytokine and antibody production, and antigen presentation). The immune response of a subject can be readily determined by the skilled artisan using methods well known in the art, for example, by assaying for antibody production, immune cell proliferation, the release of cytokines, the expression of cell surface markers, cytotoxicity, etc.

In one embodiment, bioactive agents and methods for increasing and/or up-regulating B and T cell activity are provided. In a preferred embodiment, such bioactive agents comprise antagonists of BTLA-mediated signaling. In a particularly preferred embodiment, such bioactive agents comprise blocking agents as described herein, and in a specific embodiment, such blocking agents are capable of interfering with the interaction of BTLA and B7x. In a further embodiment, adjuvant compositions are provided utilizing BTLA and/or B7x blocking agents and other antagonists of BTLA-mediated signaling.

In an alternative embodiment, bioactive agents and methods for inhibiting and/or down-regulating B and T cell activity are provided. In a preferred embodiment, such bioactive agents comprise agonists of BTLA-mediated signaling. In a particularly preferred embodiment, such bioactive agents comprise mimicking agents as described herein, and in a specific embodiment, such mimicking agents are capable of replacing and/or augmenting the interaction of BTLA and B7x. In a further embodiment, immunsuppressive compositions are provided utilizing BTLA and/or B7x mimicking agents and other agonists of BTLA-mediated signaling.

In a further embodiment, methods and compositions for modulating immunoglobulin production by B cells is provided.

By "BTLA signaling", "BTLA-mediated signaling", "BTLA-mediated negative signaling" and variations thereof is meant intracellular signaling in lymphocytes caused by the binding and/or activation of the BTLA receptor by its corresponding ligand(s) resulting in attenuation and/or down-regulation of lymphocyte activity. In one aspect, BTLA-mediated signaling comprises activation of SHP-1 and/or SHP-2.

"Lymphocyte activity" as used herein refers to the immunological processes of B and T cell activation, proliferation, differentiation and survival, as well as associated effector immune functions in lymphocytic cells including cytolytic activity (Tc cells), cytokine production (Th cells), antibody production (B cells), and antigen presentation (B cells). As noted above, there are numerous assays well known to the skilled artisan for detecting and/or monitoring such processes, including but not limited to the assays described in the examples provided herein.

As used herein, the phrase "interaction of BTLA and B7x" refers to direct physical interaction (e.g. binding) and/or other indirect interaction of a functional B7x molecule with a functional BTLA receptor on a lymphocyte, resulting in stimulation of the BTLA receptor and associated intracellular BTLA signaling. Similarly, the phrase "natural interaction of BTLA and B7x" refers to direct physical interaction (e.g. binding) and/or other indirect interaction of a functional and endogenously expressed B7x molecule with a functional and endogenously expressed BTLA receptor on a lymphocyte, resulting in stimulation of the BTLA receptor and associated intracellular BTLA signaling.

As used herein, "functional" means to be able to carry out normal activities, such as to recognize and bind a target, or to activate intracellular signaling pathways upon stimulation.

As used herein, the term "blocking agent" includes those agents that interfere with the interaction of B7x and BTLA, and/ or that interfere with the ability of B7x to inhibit lymphocyte activity, e.g., as measured by cytokine production and/or proliferation. The term "blocking agent" further includes agents that inhibit the ability of BTLA to bind a natural ligand, e.g., B7x, and/or that interfere with the ability of BTLA to inhibit T cell activity. Exemplary agents include function-blocking antibodies, as well as peptides that block the binding of B7x with BTLA but which fail to stimulate BTLA-mediated signaling in a lymphocyte (e.g., BTLA fusion proteins), peptidomimetics, small molecules, and the like. Preferred blocking agents include agents capable of inhibiting the inducible association of BTLA with SHP-1 and/or SHP-2, or the signal transduction that derives from the interaction of SHP-1 and/or SHP-2 with BTLA.

As used herein, the term "mimicking agent" includes those agents that mimic the interaction of B7x and BTLA, and/or that augment, enhance or increase the ability of B7x and/or BTLA to inhibit lymphocyte activity. Exemplary agents include function-activating antibodies, as well as peptides that augment or enhance the ability of B7x to bind to BTLA or substitute for B7x in stimulating BTLA-mediated signaling (e.g., B7x fusion proteins), peptidomimetics, small molecules, and the like.

The methods and compositions described herein will find advantageous use in immunotherapy, including, e.g., autoimmunity, immune suppression, cancer immunotherapy and immune adjuvants.

B7x and BTLA Nucleic Acids and Proteins

Murine B7x encodes a 283 amino acid protein and shares varying degrees of identity with mouse B7.1 (13%), B7.2 (13%), B7h (14%), PD-L1 (20%), PD-L2 (16%) and B7-H3 (24%).

Two human epithelial cell cDNAs encoding a polypeptide (previously called hypothetical protein FLJ22418) having similarity to mouse B7x were identified, and two EST clones (GenBank accession nos. BF680206 and AI799522) corresponding to the same human nucleotide sequence have been identified.

Human B7x encodes a 282 amino acid protein and has 87% amino acid identity with mouse B7x. Notably, this is much higher than the 40-46% identity between human and mouse B7.1 or B7.2.

B7x protein is a type I transmembrane protein that belongs to the immunoglobulin (Ig) superfamily It has a signal peptide in its N-terminus, single extracellular IgV- and IgC-like domains, a transmembrane region and a very short cytoplasmic stub of only 1 amino acid. The absence of a heptad structure and B30.2 domains distinguishes B7x from the butyrophilins and myelin oligodendrocyte glycoproteins.

Numerous potential N-linked glycosylation sites are present in the extracellular portion of B7x. Like other members of the B7 family, B7x has four conserved cysteine residues that are likely involved in the formation of IgV- and IgC-like domains.

In both mouse and human, B7x genes are located on different chromosomes from the other known B7 family members. Mouse B7x consists of 6 exons occupying 70.15 kb in the F3 region of chromosome while human B7x is of similar size and organization in the p12/13.1 region of chromosome 1. A phylogenetic comparison of the seven known members of the B7 family from human and mouse was performed using PAUP. This analysis suggests that the extended B7 family can be divided into 3 groups: group I including B7.1, B7.2 and B7h, group II consisting of PD-L1 and PD-L2, and group III containing B7x and B7-H3.

The BTLA protein comprises a signal sequence, an extracellular V-like Ig domain, a transmembrane region, and an intracellular domain of approximately 100 amino acids that comprises several motifs implicated in signal transduction. Notably, three tyrosine residues within the cytoplasmic domain are contained within sequence motifs that are conserved between mouse and human and are implicated in signal transduction. Particularly, conserved tyrosine residues are found within a Grb2 interaction site and within two ITIM sequences.

In one aspect, the present invention provides nucleic acids encoding B7x proteins, and B7x proteins so encoded, which are capable of modulating T cell activation.

In one aspect, the present invention provides nucleic acids encoding BTLA proteins, and BTLA proteins so encoded, which are capable of modulating T cell activation.

The B7x and BTLA proteins of the present invention may be identified in several ways. "Protein" in this sense includes proteins, polypeptides, and peptides. Included among BTLA proteins are protein fragments, extracellular fragments being particularly preferred, which possess at least one activity of the BTLA protein set forth by SEQ ID NO:8 or 10, and/or at least one epitope of the BTLA protein set forth by SEQ ID NO:8 or 10. Included among B7x proteins are protein fragments, extracellular fragments being particularly preferred, which possess at least one activity of the B7x protein set forth by SEQ ID NO:1 or 2 and/or at least one epitope of the BTLA protein set forth by SEQ ID NO:1 or 2.

A B7x protein may be identified by amino acid sequence identity or similarity to the amino acid sequences set forth in SEQ ID NO:1 or 2.

A B7x protein may be identified by its ability to bind to the surface of T cells, preferably activated CD4+ and/or activated CD8+ T cells. A B7x protein may also be identified by its ability to bind to B cells expressing BTLA. Generally, a B7x protein may be identified by its ability to bind to B or T cells expressing BTLA.

A B7x protein may be identified by its ability to bind to a BTLA protein described herein.

A B7x protein may be identified by its ability to modulate T-lymphocyte activation, preferably Th1 activation. More preferably, a B7x protein may be identified by its ability to bind to BTLA expressed on a T cell and to thereby inhibit T cell activation.

A B7x protein may be identified by its elevated expression in tumor cells.

A BTLA protein may be identified by amino acid sequence identity or similarity to the amino acid sequences set forth in SEQ ID NO:8 or 10.

A BTLA protein may be identified by its ability to bind to the surface of tumor cells expressing B7x.

A BTLA protein may be identified by its ability to bind to a B7x protein described herein.

A BTLA protein may be identified by its expression in Tc and Th cells, and its elevated expression in polarized Th1 cells.

A BTLA protein may be identified by its ability to modulate T cell activation, preferably CD4+ and CD8+ T cell activation, when expressed in the T cell, and upon binding to ligand. Preferably, the ligand is B7x, a fragment thereof, or a fusion protein comprising B7x, or a fragment thereof.

B7x and BTLA proteins may initially be identified by sequence identity or similarity to the sequences set forth in the figures, as further described below. In a preferred embodiment, B7x and BTLA proteins have sequence identity or similarity to the sequences and one or more B7x and BTLA bioactivities, respectively. Such sequence identity or similarity can be based upon the overall sequence.

In a preferred embodiment, B7x proteins provided herein comprise an amino acid sequence having at least about 80%, more preferably at least about 85%, more preferably at least about 90%, more preferably at least about 95%, more preferably at least about 98% identity to the amino acid sequence set forth in SEQ ID NO:1 or 2. In a preferred embodiment, the B7x protein comprises the amino acid sequence set forth in SEQ ID NO:1 or 2.

In a preferred embodiment, BTLA proteins provided herein comprise an amino acid sequence having at least about 80%, more preferably at least about 85%, more preferably at least about 90%, more preferably at least about 95%, more preferably at least about 98% identity to the amino acid sequences set forth in SEQ ID NO:8 or 10. In a preferred embodiment, the BTLA protein comprises the amino acid sequence set forth in SEQ ID NO:8 or 10.

Figure 5:
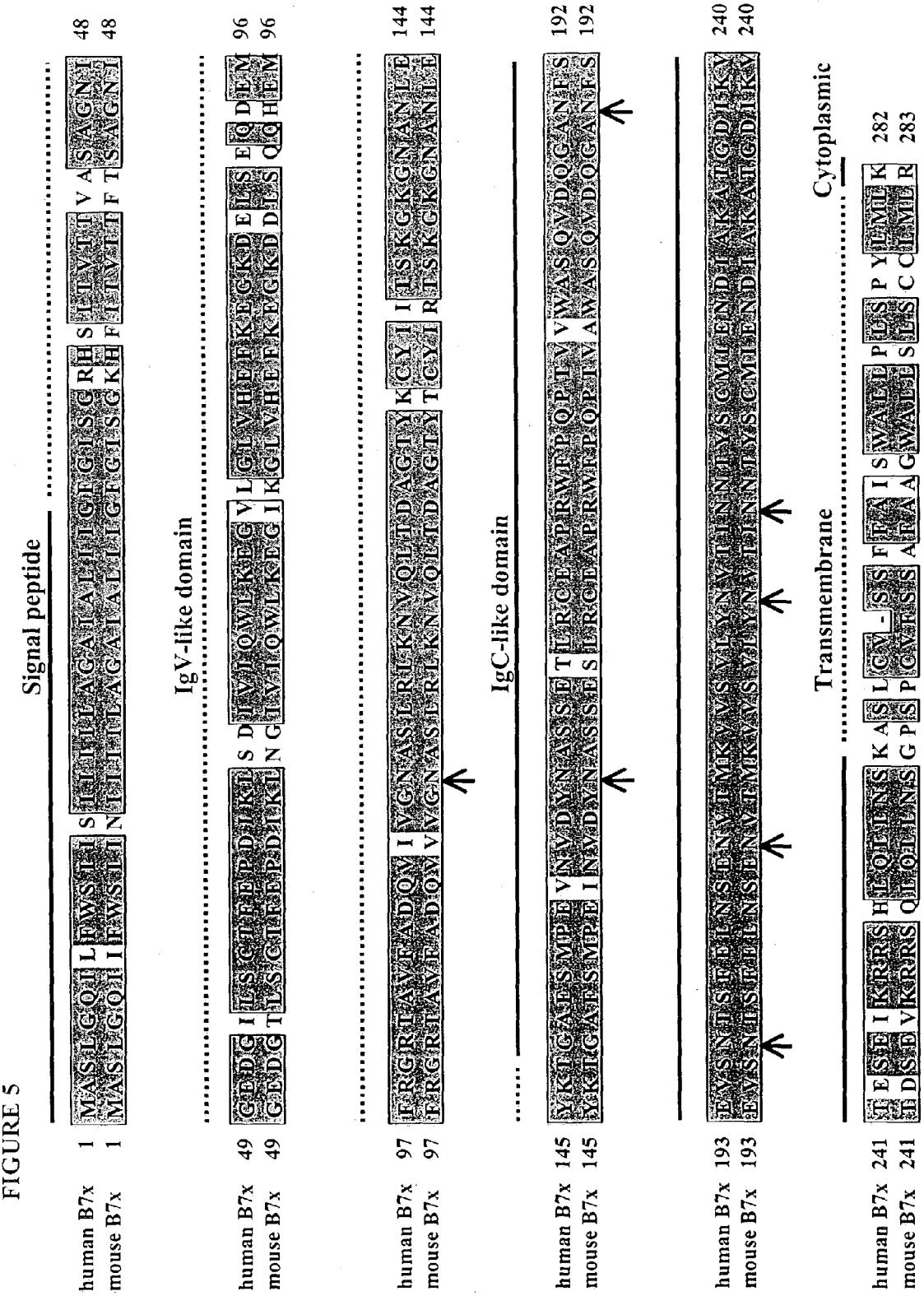
FIG. 5 shows a comparison of human B7x with mouse B7x. Predicted signal peptide, Ig V-like and C-like domains, the transmembrane region and cytoplasmic tail for B7x are indicated. Identical amino acids are highlighted in black and similar residues in gray shading. The potential N-glycosylation sites are arrowed.
Figure 6:
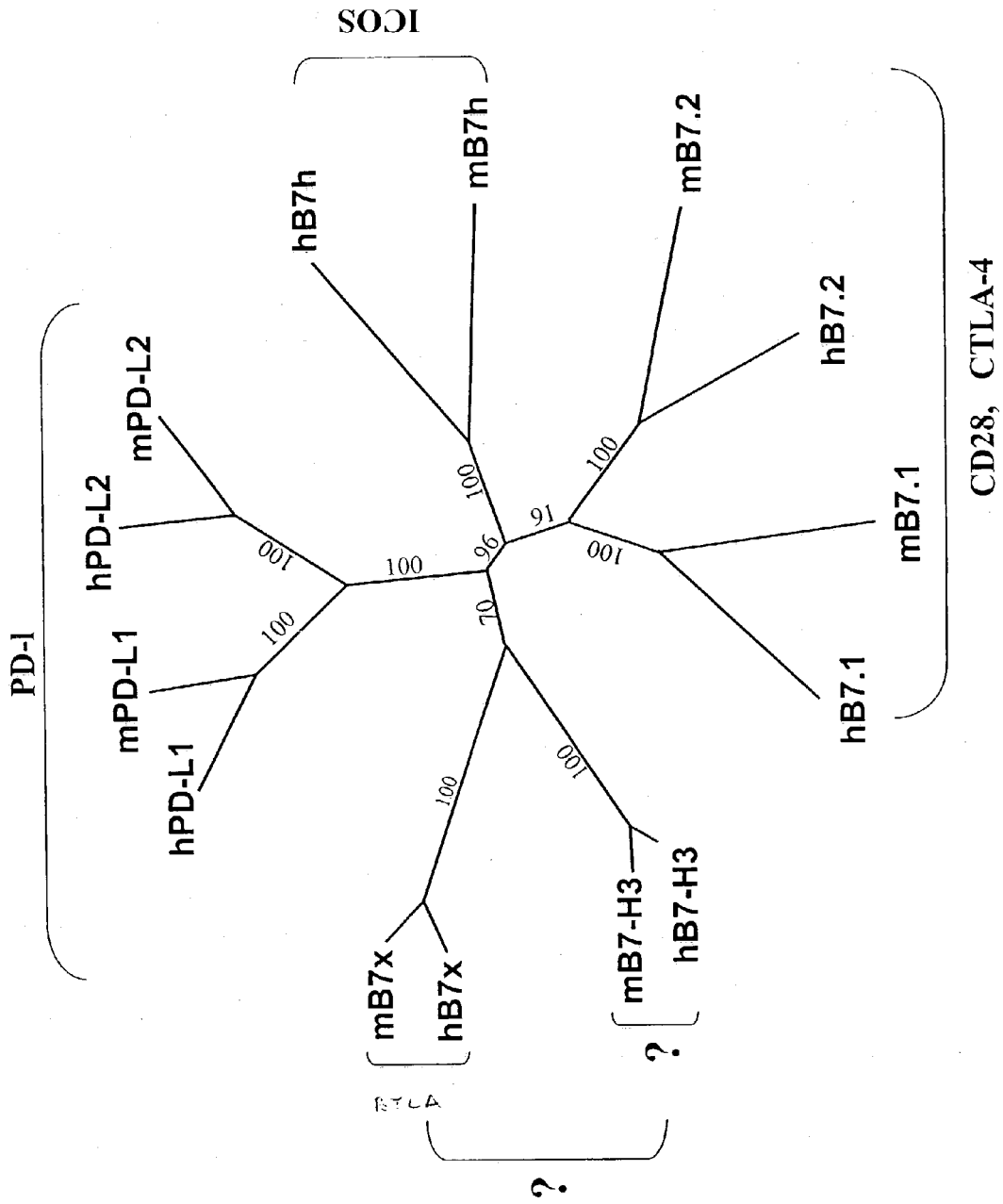
FIG. 6 shows a phylogenetic tree of the B7 family from mouse and human generated by PAUP (4.0b10) using sequence alignment by removal of significant inserts and trimming C- and N-terminal extensions. All branches of the tree were supported by Bootstrap confidence values of >50% after 100 replicates. Numbers show the percentage of bootstrap support for each clade.

In a preferred embodiment, a B7x protein provided herein comprises an extracellular domain as shown in FIG. 5. In a preferred embodiment, the B7x protein comprises an IgV-like domain and an IgC-like domain.

In another preferred embodiment, a B7x protein provided herein comprises an extracellular domain and a transmembrane domain as shown in FIG. 5. In a preferred embodiment, the B7x protein comprises an IgV-like domain and an IgC-like domain, and a transmembrane domain.

In a preferred embodiment, a B7x protein provided herein comprises a cytoplasmic domain as shown in FIG. 5.

In a preferred embodiment, a B7x protein provided herein comprises a cytoplasmic domain and a transmembrane domain as shown in FIG. 5.

In a preferred embodiment, a B7x protein provided herein comprises an extracellular domain, a transmembrane domain, and a cytoplasmic domain as shown in FIG. 5.

In a preferred embodiment, the invention provides B7x protein extracellular fragments that are capable of interacting with BTLA but incapable of activating BTLA-mediated signaling. In another preferred embodiment, the invention provides B7x protein extracellular fragments that are capable of interacting with BTLA and capable of activating BTLA-mediated signaling.

The present invention also provides BTLA proteins.

In a preferred embodiment, a BTLA protein provided herein comprises a signal sequence, an extracellular V-like Ig domain, a transmembrane region, and an intracellular domain of approximately 100 amino acids that comprises three tyrosine residues within a Grb2 interaction site and two ITIM sequences.

In another preferred embodiment, a BTLA protein provided herein comprises an extracellular V-like Ig domain, a transmembrane region, and an intracellular domain of approximately 100 amino acids that comprises three tyrosine residues within a Grb2 interaction site and two ITIM sequences.

Figure 21:
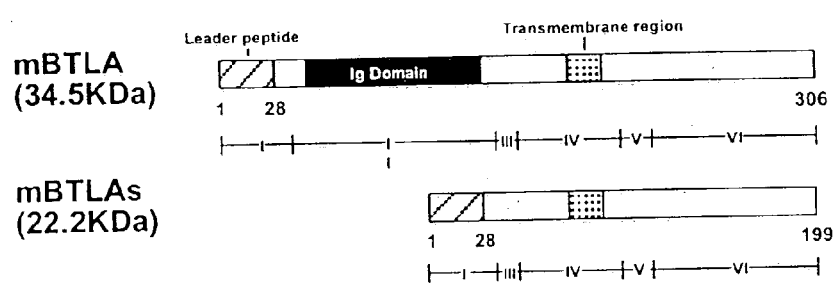
FIG. 21 shows the predicted structural regions of BTLA. Full length murine BTLA (MBTLA) and a minor splice variant (BTLAs) lacking exon 2 and deleting the Ig domain, are shown. Roman numerals shown below the figure indicate the exon from which the predicted region is derived. In parentheses is indicated the theoretical molecular weight of the predicted protein before addition of further modifications.

In another preferred embodiment, a BTLA protein provided herein comprises an extracellular V-like Ig domain, as shown in FIG. 21.

In a preferred embodiment, the invention provides BTLA protein fragments comprising a V-like Ig domain, wherein the Ig-like domain comprises an amino acid sequence having at least about 70% identity to residues 43-134, more preferably 47-133, more preferably 51-117 of the amino acid sequence set forth in SEQ ID NO:8.

In an especially preferred embodiment, the invention provides BTLA protein fragments comprising a V-like Ig domain, wherein the Ig-like domain comprises the amino acid sequence of residues 43-134, more preferably 47-133, more preferably 51-117 of the amino acid sequence set forth in SEQ ID NO:8.

In a preferred embodiment, the invention provides BTLA protein fragments comprising a V-like Ig domain, wherein the Ig-like domain comprises an amino acid sequence having at least about 70% identity to residues 57-142, more preferably residues 57-124 of the amino acid sequence set forth at SEQ ID NO:10.

In an especially preferred embodiment, the invention provides BTLA protein fragments comprising a V-like Ig domain, wherein the Ig-like domain comprises the amino acid sequence of residues 57-142, more preferably residues 57-124 of the amino acid sequence set forth at SEQ ID NO:10.

In a preferred embodiment, the invention provides BTLA protein extracellular fragments having at least about 70% identity to a portion of the extracellular domain of BTLA protein set forth by SEQ ID NO:8, partiulcarly to a portion (at least about 20 amino acids) of the sequence from about residue 31 to about residue 153 in SEQ ID NO:8.

In an especially preferred embodiment, the invention provides BTLA protein extracellular fragments comprising at least about a 20 amino acid sequence from about residue 31 to about residue 153 in SEQ ID NO:8.

In a preferred embodiment, the invention provides BTLA protein extracellular fragments having at least about 70% identity to a portion of the extracellular domain of BTLA protein set forth by SEQ ID NO:8, partiulcarly to a portion (at least about 20 amino acids) of the sequence from about residue 30 to about residue 181 in SEQ ID NO:10.

In an especially preferred embodiment, the invention provides BTLA protein extracellular fragments comprising at least about a 20 amino acid sequence from about residue 30 to about residue 181 in SEQ ID NO:10.

In a preferred embodiment, a BTLA protein provided herein comprises a signal sequence and an extracellular V-like 1g domain, as shown in FIG. 21.

In another preferred embodiment, a BTLA protein provided herein comprises an extracellular V-like Ig domain and a transmembrane region, as shown in FIG. 21.

In another preferred embodiment, a BTLA protein provided herein comprises a signal sequence, an extracellular V-like Ig domain and a transmembrane region, as shown in FIG. 21.

In another preferred embodiment, a BTLA protein provided herein comprises an intracellular domain of approximately 100 amino acids, which further comprises a Grb2 interaction site and two ITIM sequences, as shown in FIG. 21.

In another preferred embodiment, a BTLA protein provided herein comprises a transmembrane region and an intracellular domain of approximately 100 amino acids, which further comprises a Grb2 interaction site and two ITIM sequences, as shown in FIG. 21.

Figure 20:
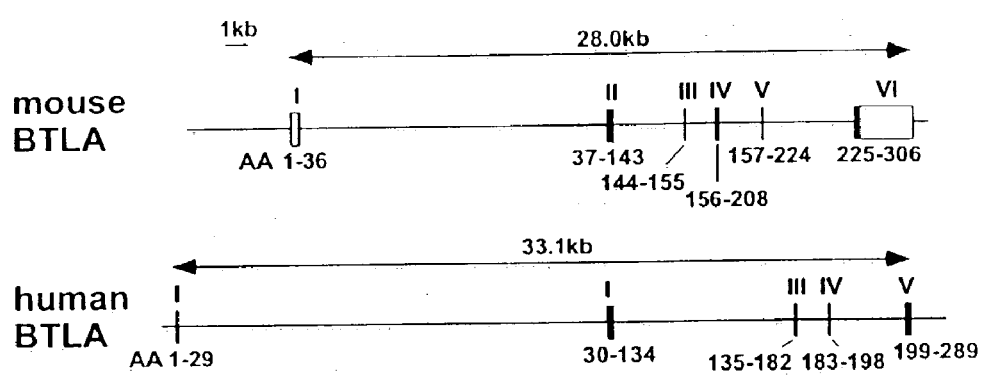
FIG. 20 shows the exon/intron organization of mouse and human BTLA genes. Filled boxes indicate coding sequence within exons, and unfilled boxes indicate 3' and 5' untranslated regions. The amino acid number encoded by each exon is indicated below.

In a highly preferred embodiment, a BTLA protein provided herein lacks the amino acid sequence encoded by exon 2 shown in FIG. 20, and accordingly lacks the Ig domain depicted in FIG. 19. In a preferred embodiment, such a BTLA protein possesses BTLA protein function.

Fragments are included in the definition of B7x and BTLA proteins herein.

In a preferred embodiment, a B7x protein provided herein consist essentially of an extracellular domain as shown in FIG. 5. In a preferred embodiment, the B7x protein consists essentially of an IgV-like domain and an IgC-like domain.

In another preferred embodiment, a B7x protein provided herein consists essentially of an extracellular domain and a transmembrane domain as shown in FIG. 5. In a preferred embodiment, the B7x protein consists essentially of an IgV-like domain and an IgC-like domain, and a transmembrane domain.

In a preferred embodiment, a B7x protein provided herein consists essentially of a cytoplasmic domain as shown in FIG. 5.

In a preferred embodiment, a B7x protein provided herein consists essentially of a cytoplasmic domain and a transmembrane domain as shown in FIG. 5.

BTLA protein fragments are also provided.

In a preferred embodiment, a BTLA protein provided herein consists essentially of an extracellular V-like Ig domain, as shown in FIG. 21.

In a preferred embodiment, a BTLA protein provided herein consists essentially of a signal sequence and an extracellular V-like Ig domain, as shown in FIG. 21.

In another preferred embodiment, a BTLA protein provided herein consists essentially of an extracellular V-like Ig domain and a transmembrane region, as shown in FIG. 21.

In another preferred embodiment, a BTLA protein provided herein consists essentially of a signal sequence, an extracellular V-like Ig domain and a transmembrane region, as shown in FIG. 21.

In another preferred embodiment, a BTLA protein provided herein consists essentially of an intracellular domain of approximately 100 amino acids, which further comprises a Grb2 interaction site and two ITIM sequences, as shown in FIG. 21.

In another preferred embodiment, a BTLA protein provided herein consists essentially of a transmembrane region and an intracellular domain of approximately 100 amino acids, which further comprises a Grb2 interaction site and two ITIM sequences, as shown in FIG. 21.

Recombinant techniques that are well known in the art may be used to combine BTLA or B7x protein fragments disclosed herein with other moieties for a variety of purposes, as further discussed below. These processes involve the manipulation of nucleic acids encoding BTLA and B7x proteins disclosed herein.

In one aspect, the present invention provides B7x nucleic acids, including B7x nucleic acids encoding B7x proteins.

In another aspect, the present invention provides BTLA nucleic acids, including BTLA nucleic acids encoding BTLA proteins.

By "nucleic acid" or oligonucleotide or grammatical equivalents herein means at least two nucleotides covalently linked together. A nucleic acid of the present invention will generally contain phosphodiester bonds, although in some cases, as outlined herein, particularly with respect to antisense nucleic acids or probes, nucleic acid analogs are included that may have alternate backbones, comprising, for example, phosphoramide (Beaucage, et al, Tetrahedron, 49(10):1925 (1993) and references therein; Letsinger, *J. Org. Chem.*, 35:3800 (1970); Sprinzl, et a., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al, *J. Am. Chem. Soc.,* 110:4470 (1988); and Pauwels, et al., *Chemica Scripta,* 26:141 (1986)), phosphorothioate (Mag, et al., *Nucleic Acids Res.,* 19:1437 (1991); and U.S. Pat. No. 5,644,048), phosphorodithioate (Briu, et al., *J. Am. Chem. Soc.,* 111:2321 (1989)), O-methylphophoroamidite linkages (see Eckstein, Oligonucleotides and Analogues: A Practical Approach, Oxford University Press), and peptide nucleic acid backbones and linkages (see Egholm, *J. Am. Chem. Soc.,* 114:1895 (1992); Meier, et al, *Chem. Int. Ed. En.,* 31:1008 (1992); Nielsen, *Nature,* 365:566 (1993); Carlsson, et al., *Nature,* 380:207 (1996), all of which are incorporated by reference)). Other analog nucleic acids include those with positive backbones (Denpcy, et al., *Proc. Natl. Acad. Sci. USA,* 92:6097 (1995)); non-ionic backbones (U.S. Pat. Nos. 5,386,023; 5,637,684; 5,602,240; 5,216,141; and 4,469,863; Kiedrowshi, et al., *Angew. Chem. Intl. Ed. English,* 30:423 (1991); Letsinger, et al., *J. Am. Chem. Soc.,* 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al, *Bioorganic & Medicinal Chem. Lett.,* 4:395 (1994); Jeffs, et al., *J. Biomolecular NMR,* 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars, as well as "locked nucleic acids", are also included within the definition of nucleic acids (see Jenkins, et al., *Chem. Soc. Rev.,* (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

With respect to nucleic acids that encode B7x and BTLA proteins, it will be appreciated by those in the art, that due to the degeneracy of the genetic code, an extremely large number of nucleic acids may be made, all of which encode the B7x and BTLA proteins of the present invention. Thus, having identified a particular amino acid sequence, those skilled in the art could make any number of different nucleic acids, by simply modifying the sequence of one or more codons in a way which does not change the amino acid sequence of the B7x or BTLA protein.

Included among B7x nucleic acids are allelic variants. A B7x allelic variant refers to one of several possible naturally occurring alternate forms of the B7x gene occupying a given locus on a chromosome of an organism or a population of organisms. The existence of naturally occurring alternate forms is referred to as polymorphism. B7x nucleic acids also include splice variants. B7x splice variant refers to a nucleic acid, usually RNA, which is generated by alternative processing of intron sequences in an B7x RNA transcript to produce alternate B7x proteins.

Included among BTLA nucleic acids are allelic variants. A BTLA allelic variant refers to one of several possible naturally occurring alternate forms of the BTLA gene occupying a given locus on a chromosome of an organism or a population of organisms. The existence of naturally occurring alternate forms is referred to as polymorphism. As disclosed herein, BTLA polymorphism has been observed in mice. BTLA nucleic acids also include splice variants. BTLA splice variant refers to a nucleic acid, usually RNA, which is generated by alternative processing of intron sequences in an BTLA RNA transcript to produce alternate BTLA proteins. As disclosed herein, presumed alternatively spliced forms of BTLA have been identified.

In a preferred embodiment, the present invention provides B7x nucleic acids encoding B7x proteins, which comprise a nucleotide sequence having at least about 80%, more preferably at least about 85%, more preferably at least about 90%, more preferably at least about 95%, most preferably at least about 98% identity to the nucleotide sequence set forth in FIG. 2 or FIG. 3.

In another preferred embodiment, the present invention provides B7x nucleic acids encoding B7x proteins, which comprise a nucleotide sequence encoding an amino acid sequence having at least about 80%, more preferably at least about 85%, more preferably at least about 90%, more preferably at least about 95%, most preferably at least about 98% identity to one of the amino acid sequence set forth in FIG. 1.

In a preferred embodiment, the present invention provides B7x nucleic acids encoding a B7x protein, which nucleic acids are about 1.9, 3.5, or 8.2 kb in size.

In another preferred embodiment, the present invention provides B7x nucleic acids encoding a B7x protein, which nucleic acids are about 3.2 kb in size.

In another preferred embodiment the present invention provides BTLA nucleic acids encoding BTLA proteins, which comprise a nucleotide sequence encoding an amino acid sequence having at least about 80%, more preferably at least about 85%, more preferably at least about 90%, more preferably at least about 95%, most preferably at least about 98% identity to one of the amino acid sequences set forth in FIG. 19.

In another preferred embodiment, the present invention provides BTLA nucleic acids encoding BTLA proteins that lack the protein sequence encoded by exon 2, and consequently lack the Ig domain depicted in FIG. 21.

In a preferred embodiment, the present invention provides B7x nucleic acids encoding B7x protein fragments described herein.

In another preferred embodiment, the present invention provides BTLA nucleic acids encoding BTLA protein fragments described herein.

In some embodiments, B7x and BTLA nucleic acids are determined through hybridization studies. Thus, for example, nucleic acids which hybridize under high stringency conditions to the nucleotide sequences set forth in the figures, or to those which encode the amino acid sequences set forth in the figures, or complements thereof, or fragments thereof or their complements, are considered B7x or BTLA nucleic acids. High stringency conditions are known in the art; see for example Sambrook et al., *Molecular Cloning, A Laboratory Manual,* 3rd edition, 2001, Cold Spring Harbor Press, Cold Spring Harbor, N.Y.; and *Short Protocols in Molecular Biology,* ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In other embodiments, less stringent hybridization conditions are used; for example, moderate or low stringency conditions may be used, as are known in the art; see Sambrook et al., *Molecular Cloning, A Laboratory Manual*, 3rd edition, 2001, Cold Spring Harbor Press, Cold Spring Harbor, N.Y.; and Tijssen, supra.

Also provided herein are B7x antisense nucleic acids which will hybridize under high stringency conditions to a B7x nucleic acid. In a preferred embodiment, the B7x antisense nucleic acid inhibits expression of B7x protein. In a preferred embodiment, the B7x antisense nucleic acid inhibits B7x protein activity.

Also provided herein are BTLA antisense nucleic acids which will hybridize under high stringency conditions to a BTLA nucleic acid encoding a BTLA protein. In a preferred embodiment, the BTLA antisense nucleic acid inhibits expression of BTLA protein. In a preferred embodiment, the BTLA antisense nucleic acid inhibits BTLA protein activity.

As is known in the art, a number of different programs can be used to identify whether a protein or nucleic acid has sequence identity or similarity to a known sequence. For a detailed discussion, see D. Mount, *Bioinformatics*, Cold Spring Harbor Press, Cold Spring Harbor, N.Y., 2001, ISBN 0-87969-608-7. Sequence identity and/or similarity is determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989). Useful PILEUP parameters including a default gap weight of 3.00, a default gap length weight of 0.10, and weighted end gaps. Another example of a useful algorithm is the BLAST algorithm, described in Altschul et al., J. Mol. Biol. 215, 403-410, (1990) and Karlin et al., PNAS USA 90:5873-5787 (1993). A particularly useful BLAST program is the WU-BLAST-2 program which was obtained from Altschul et al., *Methods in Enzymology*, 266: 460-480 (1996)]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. An additional useful algorithm is gapped BLAST as reported by Altschul et al. Nucleic Acids Res. 25:3389-3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits. A percent amino acid sequence identity value is determined by the number of matching identical residues divided by the total number of residues of the longer sequence in the aligned region. The longer sequence is the one having the most actual residues in the aligned region (gaps introduced by WU-Blast-2 to maximize the alignment score are ignored).

The alignment may include the introduction of gaps in the sequences to be aligned. In addition, for sequences which contain either more or fewer amino acids than the protein sequences set forth in the figures, it is understood that in one embodiment, the percentage of sequence identity will be determined based on the number of identical amino acids in relation to the total number of amino acids. Thus, for example, the percent sequence identity of sequences shorter than those shown in the figures will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of 0, which obviates the need for a weighted scale or parameters as described below for sequence similarity calculations. Percent sequence identity can be calculated, for example, by dividing the number of matching identical residues by the total number of residues of the shorter sequence in the aligned region and multiplying by 100. The longer sequence is the one having the most actual residues in the aligned region.

Figure 4:
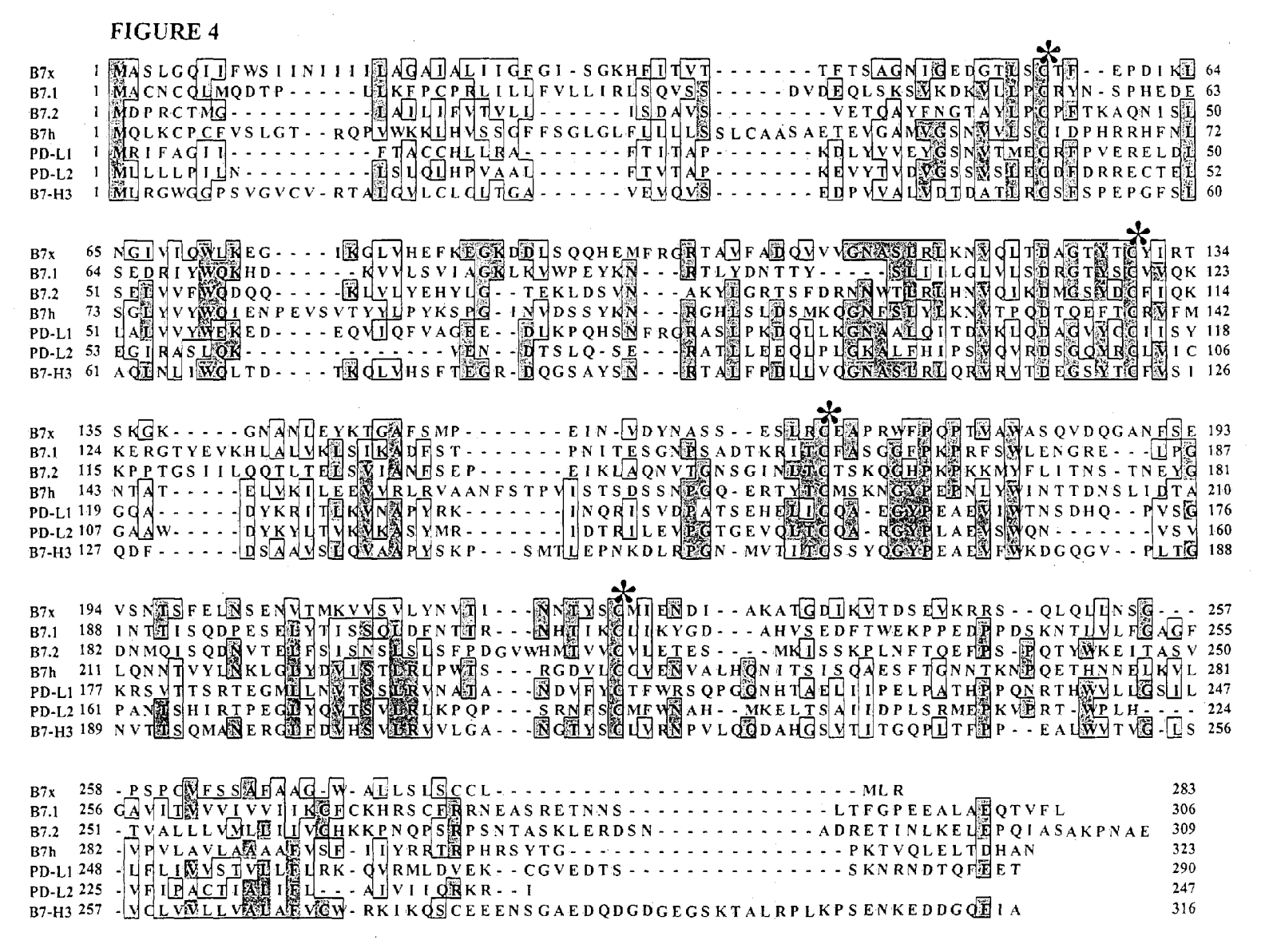

In a similar manner, percent (%) nucleic acid sequence identity is defined as the percentage of nucleotide residues in a candidate sequence that are identical with the nucleotide residues in the B7x nucleic acid set forth in FIG. 2 or 4, or a BTLA nucleic acid sequence encoding a BTLA amino acid sequence set forth in FIG. 19. A preferred method utilizes the BLASTN module of WU-BLAST-2 set to the default parameters, with overlap span and overlap fraction set to 1 and 0.125, respectively.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

B7x and BTLA proteins of the present invention may be shorter or longer than the amino acid sequences set forth in the figures, or encoded by the nucleic acid sequences set forth in the figures.

In one embodiment herein, fragments of B7x proteins are considered B7x proteins if a) they share at least one antigenic epitope; b) have at least the indicated sequence identity; c) and preferably have B7x protein activity as further defined herein.

Similarly, fragments of BTLA proteins are considered BTLA proteins if a) they share at least one antigenic epitope; b) have at least the indicated sequence identity; c) and preferably have BTLA protein activity as further defined herein.

The nucleic acids of the present invention may also be shorter or longer than those shown in the figures, or those encoding the amino acid sequences shown in the figures. In some cases, where a sequence is used diagnostically, that is, when the presence or absence of a B7x or a BTLA nucleic acid is determined, only the indicated sequence identity is required. The nucleic acid fragments provided herein include nucleic acids consisting essentially of portions of the sequences provided herein that have not been exactly identified previously; fragments having sequences with the indicated sequence identity to that portion not previously identified are also provided in an embodiment herein.

In addition, as is more fully outlined below, B7x and BTLA proteins can be made that are longer than those depicted in the figures, for example, by the addition of epitope or purification tags, the addition of other fusion sequences, or the elucidation of additional coding and non-coding sequences. As described below, the fusion of a B7x or BTLA protein to a fluorescent protein, such as Blue Fluorescent Protein (BFP) or Green Fluorescent Protein (GFP), is preferred in one embodiment. In a highly preferred embodiment, a B7x or BTLA protein, or fragment thereof, is fused to the constant region of an immunoglobulin, thereby creating a B7x-Ig or BTLA-Ig fusion protein.

The B7x and BTLA proteins and nucleic acids of the present invention are preferably recombinant. As used herein and further defined below, nucleic acid may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded and single stranded sequence. As will be appreciated by those in the art, the depiction of a single strand ("Watson") also defines the sequence of the other strand ("Crick"); thus the sequences depicted in the figures also include the complement of the sequence.

By the term recombinant nucleic acid herein is meant nucleic acid, originally formed in vitro, in general, by the manipulation of nucleic acid by endonucleases, in a form not normally found in nature. Thus an isolated B7x or BTLA nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a recombinant protein is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a B7x and BTLA proteins from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag, or amino acid substitutions, insertions and deletions, as discussed below.

An isolated polypeptide refers to a polypeptide of the invention that (1) has been separated from at least about 50% of polynucleotide, lipid, carbohydrate, or other material with which it is naturally found when isolated from a source cell, (2) is not linked (by covalent or noncovalent interaction) to all or a portion of a polypeptide to which the isolated polypeptide is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prohylactic or research use.

In a preferred embodiment, the present invention provides B7x protein variants. In another preferred embodiment, the invention provides BTLA protein variants. These variants fall into one or more of three classes: substitutional, insertional or deletional variants. These variants ordinarily are prepared by site specific mutagenesis of nucleotides in the DNA encoding a B7x or BTLA protein, using cassette or PCR mutagenesis or other techniques well known in the art, to produce DNA encoding the variant, and thereafter expressing the DNA in recombinant cell culture as outlined above. However, variant protein fragments having up to about 100-150 residues may be prepared by in vitro synthesis using established techniques. Amino acid sequence variants are characterized by the predetermined nature of the variation, a feature that sets them apart from naturally occurring allelic or interspecies B7x or BTLA proteins. The variants typically exhibit the same qualitative biological activity as the naturally occurring analogue, although variants can also be selected which have modified characteristics, as will be more fully outlined below.

In an especially preferred embodiment, the invention provides B7x variants that exhibit an elevated B7x bioactivity as compared to the activity of B7x proteins set forth in FIG. 1.

In another especially preferred embodiment, the invention provides BTLA variants that exhibit an elevated BTLA bioactivity as compared to the activity of BTLA proteins set forth in FIG. 19.

While the site or region for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence are well known, for example, M13 primer mutagenesis and PCR mutagenesis. Screening of the mutants may be done using assays that measure B7x or BTLA activity, as described herein.

In an especially preferred embodiment, B7x variant proteins are screened for their ability to modulate T-lymphocyte activation as described herein.

In another especially preferred embodiment, B7x variant proteins are screened for their ability to bind BTLA protein.

In another especially preferred embodiment, BTLA variant proteins are screened for their ability to modulate T cell activation as described herein.

In another especially preferred embodiment, BTLA variant proteins are screened for their ability to bind B7x protein.

Amino acid substitutions are typically of single residues; insertions usually will be on the order of from about 1 to 20 amino acids, although considerably larger insertions may be tolerated. Deletions range from about 1 to about 20 residues, although in some cases deletions may be much. larger. Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the B7x protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |

CHART I-continued

| Original Residue | Exemplary Substitutions |
| --- | --- |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the B7x and BTLA proteins as needed. The variant may be designed such that the biological activity of the B7x or BTLA protein is altered. For example, glycosylation sites may be altered or removed.

Covalent modifications of BTLA and B7x polypeptides are included within the scope of this invention. One type of covalent modification includes reacting targeted amino acid residues of a B7x or BTLA polypeptide with an organic derivatizing agent that is capable of reacting with selected side chains or the N-or C-terminal residues of the polypeptide. Derivatization with bifunctional agents is useful, for instance, for crosslinking B7x or BTLA to a water-insoluble support matrix or surface for use in a method for purifying anti-B7x or anti-BTLA antibodies, or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the amino groups of lysine, arginine, and histidine side chains [T. E. Creighton, *Proteins: Structure and Molecular Properties*, W. H. Freeman & Co., San Francisco, pp. 79-86 (1983)], acetylation of the N-terminal amine, and amidation of any C-terminal carboxyl group.

Another type of covalent modification of B7x and BTLA polypeptides included within the scope of this invention comprises altering the native glycosylation pattern of the polypeptide. Altering the native glycosylation pattern is intended for purposes herein to mean deleting one or more carbohydrate moieties found in the native sequence of B7x or BTLA polypeptide, and/or adding one or more glycosylation sites that are not present in the native sequence.

Addition of glycosylation sites to B7x or BTLA polypeptides may be accomplished by altering the amino acid sequence thereof. The alteration may be made, for example, by the addition of, or substitution by, one or more serine or threonine residues to the native polypeptide sequence (for O-linked glycosylation sites). The B7x or BTLA amino acid sequence may optionally be altered through changes at the DNA level, particularly by mutating the DNA encoding the polypeptide at preselected bases such that codons are generated that will translate into the desired amino acids. Another means of increasing the number of carbohydrate moieties on the B7x or BTLA polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem., pp.* 259-306 (1981).

Removal of carbohydrate moieties present on a B7x or BTLA polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. BioPhys.,* 259:52 (1987) and by Edge et al., *Anal. Biochem.,* 118:131 (1981). Enzymatic cleavage of carbohydrate moieties on polypeptides can be achieved by the use of a variety of endo-and exo-glycosidases as described by Thotakura et al., *Meth. Enzymol.,* 138:350 (1987).

Another type of covalent modification of B7x and BTLA protein contemplated by the invention comprises linking the polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

B7x and BTLA polypeptides of the present invention may also be modified in a way to form chimeric molecules comprising a B7x or BTLA polypeptide fused to another, heterologous polypeptide or amino acid sequence. In one embodiment, such a chimeric molecule comprises a fusion of a B7x or BTLA polypeptide with a tag polypeptide which provides an epitope to which an anti-tag antibody can selectively bind. In a preferred embodiment, such a tag is the "flag tag" described below. The epitope tag is generally placed at the amino-or carboxyl-terminus of the B7x or BTLA polypeptide. The presence of such epitope-tagged forms of polypeptide can be detected using an antibody against the tag. Also, provision of the epitope tag enables the B7x or BTLA polypeptide to be readily purified by affinity purification using an anti-tag antibody or another type of affinity matrix that binds to the epitope tag. In an alternative. embodiment, the chimeric molecule may comprise a fusion of a B7x or BTLA polypeptide with an immunoglobulin or a particular region of an immunoglobulin. For a bivalent form of the chimeric molecule, such a fusion could be to the Fc region of an IgG molecule as discussed further below.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.,* 8:2159-2165 (1988)]; the c-myc tag and the 8F9, 3C7, 6E10, G4, B7 and 9E10 antibodies thereto [Evan et al., *Molecular and Cellular Biolopy,* 5:3610-3616 (1985)]; and the Herpes Simplex virus glycoprotein D (gD) tag and its antibody [Paborsky et al., *Protein Engineering,* 3(6):547-553 (1990)]. Other tag polypeptides include the Flag-peptide [Hopp et al., *BioTechnology,* 6:1204-1210 (1988)]; the KT3 epitope peptide [Martin et al., Science, 255:192-194 (1992)]; tubulin epitope peptide [Skinner et al., *J. Biol. Chem.,* 266:15163-15166 (1991)]; and the T7 gene 10 protein peptide tag [Lutz-Freyermuth et al., *Proc. Natl. Acad. Sci. USA,* 87:6393-6397 (1990)].

In some embodiments herein, B7x or BTLA protein family members and B7x or BTLA proteins from other organisms are cloned and expressed as outlined below. Thus, probe or degenerate polymerase chain reaction (PCR) primer sequences may be used to find other related B7x and BTLA proteins from humans or other organisms. As will be appreciated by those in the art, particularly useful probe and/or PCR primer sequences include the unique areas of B7x and BTLA nucleic acid sequences. As is generally known in the art, preferred PCR primers are from about 15 to about 35 nucleotides in length, with from about 20 to about 30 being preferred, and may contain inosine as needed. The conditions for the PCR reaction are well known in the art. It is therefore also understood that provided along with the sequences in the sequences listed herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant B7x and BTLA nucleic acids can be further used as probes to identify and isolate other B7x and BTLA nucleic acids. They can also be used as precursor nucleic acids to make rmodified or variant nucleic acids and proteins.

Using the nucleic acids of the present invention, a variety of expression vectors are made. The expression vectors may be either self-replicating extrachromosomal vectors or vectors which integrate into a host genome. Generally, these expression vectors include transcriptional and translational regulatory nucleic acid operably linked to a nucleic acid encoding a B7x or BTLA protein. The term control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the B7x or BTLA protein; for example, transcriptional and translational regulatory nucleic acid sequences from *Bacillus* are preferably used to express protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

B7x and BTLA proteins of the present invention may be produced by culturing a host cell transformed with an expression vector containing a B7x or BTLA nucleic acid encoding a B7x or BTLA protein, respectively, under the appropriate conditions to induce or cause expression of the protein. The conditions appropriate for B7x or BTLA protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli*, *Bacillus subtilis*, SF9 cells, C129 cells, 293 cells, *Neurospora*, BHK, CHO, COS, and HeLa cells, fibroblasts, *Schwanoma* cell lines, immortalized mammalian myeloid and lymphoid cell lines such as Jurkat and BJAB cells.

In a preferred embodiment, B7x and BTLA proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for B7x or BTLA into mRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase 11 to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, are well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, B7x and BTLA proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of B7x or BTLA into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3-9 nucleotides in length located 3-11 nucleotides upstream of the initiation codon.

The expression vector may also include a signal peptide sequence that provides for secretion of the B7x or BTLA protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In some embodiments, B7x or BTLA proteins are produced in insect cells. Expression vectors for the transformation of insect cells, and in particular, baculovirus-based expression vectors, are well known in the art.

In a preferred embodiment, a B7x or BTLA protein is produced in yeast cells. Yeast expression systems are well known in the art, and include expression vectors for *Saccharomyces cerevisiae, Candida* alB7xans and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1, 10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

B7x and BTLA proteins may also be made as fusion proteins, using techniques well known in the art. Thus, for example, for the creation of monoclonal antibodies, if the desired epitope is small, the B7x or BTLA protein may be fused to a carrier protein to form an immunogen. Alternatively, the B7x or BTLA protein may be made as a fusion protein to increase expression, or for other reasons. For example, when the B7x or BTLA protein is a peptide, the nucleic acid encoding the peptide may be linked to other nucleic acid for expression purposes. Similarly, B7x and BTLA proteins of the invention can be linked to protein labels, such as green fluorescent protein (GFP), red fluorescent protein (RFP), blue fluorescent protein (BFP), yellow fluorescent protein (YFP), etc.

In some embodiments, the B7x or BTLA nucleic acids, and/or proteins, and/or antibodies of the invention are labeled. By labeled herein is meant that a compound has at least one element, isotope or chemical compound attached to enable the detection of the compound. In general, labels fall into four classes: a) isotopic labels, which may be radioactive or heavy isotopes; b) immune labels, which may be antibodies or antigens; c) colored or fluorescent dyes; d) magnetic moieties. The labels may be incorporated into the compound at any position.

In a preferred embodiment, a B7x or BTLA protein is purified or isolated after expression. B7x and BTLA proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the B7x protein may be purified using a standard anti-B7x antibody column. Ultrafiltration and diafiltration techniques, in conjunction with protein concentration, are also useful. For general guidance in suitable purification techniques, see Scopes, R., *Protein Purification*, Springer-Verlag, NY (1982). The degree of purification necessary will vary depending on the use of the B7x or BTLA protein. In some instances no purification will be necessary.

Once expressed, and purified if necessary, the B7x and BTLA proteins and nucleic acids are also useful in a number of applications.

The nucleotide sequences (or their complement) encoding BTLA and B7x proteins have various applications in the art of molecular biology, including uses as hybridization probes, in chromosome and gene mapping and in the generation of anti-sense RNA and DNA. These nucleic acids are also useful for the preparation of B7x and BTLA proteins by the recombinant techniques described herein.

The full-length native sequence of the B7x or BTLA gene, or portions thereof, may be used as a hybridization probe for a cDNA library to isolate other genes (for example, allelic variants or species variants) which have a desired sequence identity to the B7x or BTLA nucleic acids. Optionally, the length of the probes will be about 20 to about 50 bases. The hybridization probes may be derived from the nucleotide sequences herein or from genomic sequences including promoters, enhancer elements and introns of native sequences as provided herein. By way of example, a screening method will comprise isolating the coding region of the B7x gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the B7x gene of the present invention can be used to screen libraries of human cDNA, genomic DNA or mRNA to determine which members of such libraries the probe hybridizes.

Nucleotide sequences encoding a B7x ot BTLA protein can also be used to construct hybridization probes for mapping genes that encode B7x or BTLA proteins, and for the genetic analysis of individuals with B7x- or BTLA-related genetic disorders. The nucleotide sequences provided herein may be mapped to a chromosome and specific regions of a chromosome using known techniques, such as in situ hybridization, linkage analysis against known chromosomal markers, and hybridization screening with libraries.

Nucleic acids which encode B7x or BTLA protein or modified forms thereof can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a B7x protein can be used to clone genomic DNA encoding a B7x protein in accordance with established techniques and the genomic sequences used to generate transgenic animals that contain cells which express the desired DNA. Methods for generating transgenic animals, particularly animals such as mice or rats, have become conventional in the art and are described, for example, in U.S. Pat. Nos. 4,736,866 and 4,870,009.

Alternatively, non-human homologues of the B7x or BTLA protein can be used to construct a "knock out" animal which has a defective or altered gene encoding either B7x or BTLA protein as a result of homologous recombination between the endogenous gene and an altered genomic DNA encoding B7x or BTLA, which is introduced into an embryonic cell of the animal. For example, cDNA encoding a B7x protein can be used to clone genomic DNA encoding a B7x protein in accordance with established techniques. A portion of the genomic DNA encoding a B7x protein can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the B7x protein.

It is understood that the models described herein can be varied. For example, "knock-in" models can be formed, or the models can be cell-based rather than animal models.

anti-B7x and anti-BTLA Antibodies

BTLA and B7x proteins may be used to generate anti-BTLA and anti-B7x antibodies, respectively. The terms "antibody" and "antibodies" as used herein include both monoclonal and polyclonal antibodies as well as antibody fragments, as are known in the art, including Fab, F(ab)$_2$, single chain antibodies (Fv for example), chimeric antibodies, humanized antibodies, etc., either produced by the modification of whole antibodies or those synthesized de novo using recombinant DNA technologies, as described in more detail herein. Antibody fragments include those portions of the antibody that bind to an epitope on the BTLA or B7x polypeptides.

Preferably, when a B7x or BTLA protein fragment is to be used as an immunogen to generate antibodies, the fragment must share at least one epitope or determinant with the full length protein. By epitope or determinant herein is meant a portion of a protein which will generate and/or bind an antibody. Thus, in most instances, antibodies made to a smaller or truncated B7x or BTLA protein will be able to bind to the corresponding full length protein. In a preferred embodiment, the epitope is unique; that is, antibodies generated to a unique epitope show little or no cross-reactivity.

In one embodiment, the invention provides anti-BTLA antibodies. In preferred embodiments, the anti-BTLA antibodies are capable of reducing or eliminating one or more biological functions of the BTLA receptor described herein. That is, the addition of anti-BTLA antibodies (polyclonal, or preferably monoclonal) to BTLA proteins (or cells comprising BTLA proteins) may reduce or eliminate at least one BTLA protein activity, and in particular, BTLA-mediated negative signaling in lymphocytes. Generally, at least a 25% decrease in activity is preferred, with at least about 50% being particularly preferred and about a 95-100% decrease being especially preferred. These antibodies are also sometimes referred to herein as function-blocking antibodies or, more generally, as blocking agents. In a particlarly preferred embodiment, such an antibody has the ability to modulate lymphocyte activity and, still more preferably, to increase and/or up-regulate such activity by inhibiting negative BTLA-mediated signaling. Further, such an antibody may have the ability to modulate immunoglubulin production by B cells expressing BTLA, and more preferably, to increase Ig production.

In an alternative embodiment, the invention provides an anti-BTLA antibody that increases or potentiates the activity of BTLA (a function-activating antibody), and/or mimicks the natural binding interaction of B7x with BTLA (more generally, a "mimicking agent"). In a particularly preferred embodiment, such an antibody has the ability to modulate lymphocyte activity, and more preferably, to decrease and/or down-regulate such activity by stimulating BTLA-mediated negative signaling. Further, such an antibody may have the ability to modulate immunoglobulin production by B cells expressing BTLA, and more preferably, to decrease Ig production.

The anti-BTLA antibodies of the invention bind to BTLA proteins. In a preferred embodiment, the antibodies specifically bind to BTLA proteins. By "specifically bind" herein is meant that the antibodies bind to the protein with a binding constant in the range of at least $10^{-4}$-$10^{-6}$ M$^{-1}$, with a preferred range being $10^{-7}$-$10^{-9}$ M$^{-1}$.

The present invention provides antibodies that specifically bind to naturally occurring human BTLA and/or murine BTLA proteins. In a preferred embodiment, the present invention provides a monoclonal anti-BTLA antibody that specifically binds to murine and/or human BTLA proteins, and in particular to one or more epitopes in the extracellular domains of such proteins. In an especially preferred embodiment, the monoclonal antibody provided is capable of inhibiting BTLA-mediated signaling, e.g., by interfering with the natural interaction of B7x and BTLA.

In another embodiment, the invention provides anti-B7x antibodies. In preferred embodiments, the anit-B7x antibodies are capable of reducing or eliminating one or more biological functions of the B7x polypeptide described herein. That is, the addition of anti-B7x antibodies (polyclonal, or preferably monoclonal) to B7x proteins (or cells comprising B7x proteins) may reduce or eliminate at least one B7x protein activity. Generally, at least a 25% decrease in activity is preferred, with at least about 50% being particularly preferred and about a 95-100% decrease being especially preferred. These antibodies are sometimes referred to herein as function-blocking antibodies or, more generally, blocking agents. Preferably, such an antibody has the ability to modulate lymphocyte activity, and more preferably, to increase and/or up-regulate lymphocyte activity by interfering with the functional interaction of BTLA and B7x. Further, such an antibody may have the ability to modulate immunoglobulin production by B cells expressing BTLA, and more preferably, to increase Ig production.

In an alternative embodiment, the invention provides an anti-B7x antibody that increases or potentiates the activity of B7x (a function-activating antibody).

The anti-B7x antibodies of the invention bind to B7x proteins. In a preferred embodiment, the antibodies specifically bind to B7x proteins. By "specifically bind" herein is meant that the antibodies bind to the protein with a binding constant in the range of at least $10^{-4}$-$10^{-6}$ M$^{-1}$, with a preferred range being $10^{-7}$-$10^{-9}$ M$^{-1}$.

The present invention provides antibodies that specifically bind to naturally occurring human B7x and/or murine B7x proteins. In a preferred embodiment, the present invention provides a monoclonal anti-B7x antibody that specifically binds to murine and/or human B7x protein. In an especially preferred embodiment, the monoclonal antibody provided is capable of interfering with the natural interaction of B7x and BTLA and inhibiting BTLA-mediated signaling The term "antibody", as used herein, includes immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CHI, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FRI, CDR1, FR2, CDR2, FR3, CDR3, FR4. The phrase "complementary determining region" (CDR) includes the region of an antibody molecule which comprises the antigen binding site.

The antibody may be an IgG such as IgG1, IgG2, IgG3 or IgG4; or IgM, IgA, IgE or IgD isotype. The constant domain of the antibody heavy chain may be selected depending upon the effector function desired. The light chain constant domain may be a kappa or lambda constant domain.

The term "antibody" as used herein also encompasses antibody fragments, and in particular, fragments that retain the ability to specifically bind to an antigen (e.g., the extracellular domain of B7x or BTLA). It has been shown that the antigen-binding function of an antibody can be performed by fragments of a full-length antibody. Examples of such binding fragments include (i) a Fab fragment, a monovalent fragment consisting of the VL, VH, CL and CHI domains; (ii) a F(ab').sub.2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antibody." Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123).

Still further, an antibody or fragment thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab').sub.2 fragments, can be prepared from whole antibodies using conventional techniques, such as papain or pepsin digestion, respectively, of whole antibodies. Moreover, antibodies, antibody fragments and immunoadhesion molecules can be obtained using standard recombinant DNA techniques, as described herein.

Antibodies may be polyclonal or monoclonal; xenogeneic, allogeneic, or syngeneic; or modified forms thereof, e.g. humanized, chimeric, etc. Preferably, antibodies of the invention bind specifically or substantially specifically to B7x and/or BTLA. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition typically displays a single binding affinity for a particular antigen with which it immunoreacts.

The antibodies described herein may be humanized antibodies, e.g., antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. Such humanized antibodies may also include antibodies in which CDR sequences derived from the germline of another mammalian species, such as a mouse, have been grafted onto human framework sequences.

As used herein, the term "extracellular domain of B7x" includes a portion of the B7x peptide which, in the cell-associated form, is extracellular. A B7x extracellular domain includes the portion of a B7x polypeptide involved in its interaction with BTLA. Similarly, the term "extracellular domain of BTLA" includes a portion of the BTLA peptide which, in the cell-associated form, is extracellular. A BTLA extracellular domain includes the portion of a BTLA polypeptide involved in its interaction with B7x.

Preferably, the anti-BTLA antibodies of the invention bind to naturally occurring forms of BTLA, but are substantially unreactive, e.g., have background binding to unrelated molecules. More preferably, such antibodies may also be specific for BTLA and substantially unreactive with other co-stimulatory T cell receptors, e.g. CTLA-4, CD28 and PD-1. Similarly, the anti-B7x antibodies of the invention preferably bind to naturally occurring forms of B7x, but are substantially unreactive, e.g., have background binding to unrelated, non-B7 molecules. In a particularly preferred embodiment such antibodies may also be specific for B7x and substantially unreactive with related B7 molecules, e.g. B7.1 or B7.2.

In addition, antibodies specific for naturally occurring B7x or BTLA peptides may or may not bind to mutant forms of such peptides. In one embodiment, mutations in the amino acid sequence of a naturally occurring B7x or BTLA peptide result in modulation of the binding (e.g., either increased or decreased binding) of the antibody to the B7x or BTLA peptide, respectively. Antibodies to B7x and BTLA peptides can be readily screened for their ability to meet this criteria. Assays to determine affinity and specificity of binding are known in the art, including competitive and non-competitive assays. Assays of interest include ELISA, RIA, flow cytometry, etc. Binding assays may use purified or semi-purified B7x or BTLA protein, or alternatively may use cells that express B7x or BTLA, e.g. cells transfected with an expression construct for B7x or BTLA. As is well known in the art, B7x and BTLA polypeptides from a variety of species, whether in soluble form or membrane bound, can be used as immunogens to induce the formation of anti-B7x and anti-BTLA antibodies, respectively. A variety of techniques for the preparation of such antibodies, whether polyclonal, monoclonal or humanized, are well know to the skilled artisan and do not require recitation herein. A concise summary of such techniques with reference to the preparation of antibodies to known B7 antigens is provided in U.S. Patent Publication No. US 2002/0071839, the entire disclosure of which is expressly incorporated herein by reference.

Additional Bioactive Agents

It will be appreciated by those skilled in the art that it is within their skill to generate additional bioactive agents and screen for their activity by following standard techniques. In a preferred embodiment, the B7x and/or BTLA proteins, nucleic acids, variants, modified proteins, cells and/or transgenics containing the said nucleic acids or proteins are used in screening assays. Identification of the B7x and/or BTLA proteins provided herein permits the design of drug screening assays for compounds that bind B7x and/or BTLA proteins, interfere with B7x and/or BTLA protein binding, or modulate B7x and/or BTLA activity.

The assays described herein preferably utilize human B7x protein and human BTLA, although other mammalian proteins may also be used, including rodents (mice, rats, hamsters, guinea pigs, etc.), farm animals (cows, sheep, pigs, horses, etc.) and primates. These latter embodiments may be preferred in the development of animal models of human disease.

In a preferred embodiment, the methods comprise combining a B7x protein and a candidate bioactive agent, and determining the binding of the candidate agent to the B7x protein. In other embodiments, further discussed below, binding interference or bioactivity is determined.

In another preferred embodiment, the methods comprise combining a BTLA protein and a candidate bioactive agent, and determining the binding of the candidate agent to the BTLA protein. In other embodiments, further discussed below, binding interference or bioactivity is determined.

The term "candidate bioactive agent" or "exogenous compound" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, i.e., at zero concentration or below the level of detection. In addition, positive controls, i.e. the use of agents known to bind B7x protein, e.g. BTLA, may be used, and vice-versa.

Candidate agents encompass numerous chemical classes, though typically they are organic molecules, preferably small organic compounds having a molecular weight of more than 100 and less than about 2,500 daltons, more preferably between 100 and 2000, more preferably between about 100 and about 1250, more preferably between about 100 and about 1000, more preferably between about 100 and about 750, more preferably between about 200 and about 500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides, e.g., peptidomimetics. Peptidomimetics can be made as described, e.g., in WO 98/56401

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are organic chemical moieties or small molecule chemical compositions, a wide variety of which are available in the literature.

Additional Therapeutic Agents

In a further embodiment, the bioactive agents disclosed herein may be advantageously combined with one or more additional therapeutic agents.

In one aspect, the antagonists and blocking agents described herein can be administered in combination with additional immune response stimulating agents such as, e.g., cytokines as well as various antigens and vaccine preparations including tumor antigens and tumor vaccines. In preferred embodiments, such cytokines stimulate antigen presenting cells, e.g., GM-CSF, M-CSF, G-CSF, IL-3, IL-12, etc. Additional proteins and/or cytokines known to enhance T cell proliferation and secretion, such as IL-2, IL-2, B7, anti-CD3 and anti-CD28 can be employed simultaneously or sequentially with the blocking agents to augment the immune response. The subject therapy may also be combined with the transfection or transduction of tumor cells with genes encoding for various cytokines or cell surface receptors, as is known in the art. See, e.g. Ogasawara et al. (1993) *Cancer Res.* 53:3561-8 and Townsend et al. (1993) *Science* 259:368-370.

In another aspect, the agonists and mimicking agents as described herein can be administered in combination with other immunosuppressive agents, e.g., antibodies against other immune cell surface markers (e.g., CD40) or against cytokines, other fusion proteins, e.g., CTLA4Ig, or other immunosuppressive drugs (e.g., cyclosporin A, FK506-like compounds, rapamycin compounds, or steroids).

It is further contemplated that the subject compositions and methods may be synergistically combined with immunotherapies based on modulation of other T cell costimulatory pathways, and with CTLA-4 modulation in particular. The subject blocking agents may be advantageously combined with CTLA-4 blocking agents. The CTLA-4 blocking agents inhibit T cell down-regulation mediated by CTLA-4 interaction with B7 family members B71 and B72 expressed on lymphoid and dendritic cells while the subject BTLA and B7x blocking agents inhibit the alternative negative BTLA-mediated signaling resulting from aberrant B7x overexpression in tumor cells. Similarly, the subject mimicking agents may be advantageously combined with CTLA-4 mimicking agents such as CTLA-41g which has already found clinical use as an immunosuppressive agent.

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds suitable for use in the invention, as well as other methods in which Rapamycin has been administered are known in the art (See, e.g. WO 95/22972, WO 95/16691, WO 95/04738, U.S. Pat. Nos. 6,015,809; 5,989,591; 5,567,709; 5,559,112; 5,530,006; 5,484,790; 5,385,908; 5,202,332; 5,162,333; 5,780,462; 5,120,727).

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506 like compounds include, for example, those described in WO 00/01385. Preferably, the language "rapamycin compound" as used herein does not include FK506-like compounds.

Another preferred embodiment of candidate nucleic acids are double stranded RNA capable of inducing RNA interference or RNAi (Bosher, J. M. et al. (2000) Nat. Cell Biol. 2: E31-36). Introducing double stranded RNA can trigger specific degradation of homologous RNA sequences, generally within the region of identity of the dsRNA (Zamore, P. D. et. al. (1997) Cell 101: 25-33). This provides a basis for silencing expression of genes, thus permitting a method for altering the phenotype of cells. The dsRNA may comprise synthetic RNA made either by known chemical synthetic methods or by in vitro transcription of nucleic acid templates carrying promoters (e.g., T7 or SP6 promoters). Alternatively, the dsRNAs are expressed in vivo, preferably by expression of palindromic fusion nucleic acids, that allow facile formation of dsRNA in the form of a hairpin when expressed in the cell. The double strand regions of the iRNA are generally about 10-500 basepairs or more, preferably 15-200 basepairs, and most preferably 20-100 basepairs.

Administration of Therapeutic Compositions

The bioactive agents of the present invention are administered to subjects in a biologically compatible form suitable for pharmaceutical administration in vivo. By "biologically compatible form suitable for administration in vivo" is meant a form of the agent to be administered in which any toxic effects are outweighed by the therapeutic effects of the antibody. The term subject is intended to include living organisms in which an immune response can be elicited, e.g., mammals. Examples of subjects include humans, dogs, cats, mice, rats, and transgenic species thereof. Administration of a bioactive agent as described herein can be in any pharmacological form, including a therapeutically active amount of an anti-B7x or anti-BTLA antibody alone or in combination with each other, or with an additional therapeutic agent as described herein and a pharmaceutically acceptable carrier. Administration of a therapeutically effective amount of the therapeutic compositions of the present invention is defined as an amount effective, at dosages and for periods of time necessay to achieve the desired immunotherapeutic result. For example, a therapeutically active amount of an anti-B7x or anti-BTLA antibody may vary according to factors such as the disease state, age, sex, and weight of the individual, and the ability of peptide to elicit a desired response in the individual. A dosage regime may be adjusted to provide the optimum therapeutic response. For example, several divided doses may be administered daily or the dose may be proportionally reduced as indicated by the exigencies of the therapeutic situation.

The bioactive agent (e.g., antibody) may be administered in a convenient manner such as by injection (subcutaneous, intravenous, etc.), oral administration, inhalation, transdermal application, or rectal administration. Depending on the route of administration, the bioactive agent may be coated in a material to protect the compound from the action of enzymes, acids and other natural conditions which may inactivate the compound.

To administer a bioactive agent comprising a protein, e.g. an anti-B7x or anti-BTLA antibody, by other than parenteral administration, it may be necessary to coat the peptide with, or co-administer the antibody with, a material to prevent its inactivation. An anti-B7x or anti-BTLA antibody may be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Exemplary adjuvants include alum, resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) J. Neuroimmunol 7:27).

The bioactive agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

In one embodiment, a pharmaceutical composition suitable for injectable use include sterile aqueous solutions (where water soluble) or dispersions and sterile powders for the extemporaneous preparation of sterile injectable solutions or dispersion. In all cases, the composition will preferably be sterile and fluid to the extent that easy syringability exists. It will preferably be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating one or more bioactive agents, together or separately with additional immune response stimulating agents or immunosupressants, in the required amount in an appropriate solvent with one or a combination of ingredients enumerated above, as required, followed by filtered sterilization. Generally, dispersions are prepared by incorporating the bioactive agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

When a bioactive agent comprising a peptide is suitably protected, as described above, the protein may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary bioactive agents can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of bioactive agent calculated to produce the desired therapeutic effect in association with the required pharmaceutical carrier. The specification for the dosage unit forms of the invention are dictated by and directly dependent on (a) the unique characteristics of the bioactive agent(s) and the particular therapeutic effect to be achieved, and (b) the limitations inherent in the art of compounding such an agent for the treatment of sensitivity in individuals.

The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

The toxicity and therapeutic efficacy of the bioactive agents described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such agents lies preferably within a range of circulating concentrations that include the ED50 with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the IC50 (i.e., the concentration of the test agent which achieves a half-maximal inhibition of symptoms) as determined in cell culture. Such information can be used to more accurately determine useful doses in humans. Levels in plasma may be measured, for example, by high performance liquid chromatography.

In one embodiment of the present invention a therapeutically effective amount of an antibody to B7x or BTLA is administered to a subject. As defined herein, a therapeutically effective amount of antibody (i.e., an effective dosage) ranges from about 0.001 to 50 mg/kg body weight, preferably about 0.01 to 40 mg/kg body weight, more preferably about 0.1 to 30 mg/kg body weight, about 1 to 25 mg/kg, 2 to 20 mg/kg, 5 to 15 mg/kg, or 7 to 10 mg/kg body weight.

The optimal dose of the antibody given may even vary in the same patient depending upon the time at which it is administered.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of assays designed to monitor transplant status (e.g., whether rejection or an immune response in the subject has occurred) as known in the art or as described herein.

In one embodiment, a pharmaceutical composition for injection could be made up to contain 1 ml sterile buffered water, and 1 to 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, Remington's Pharmaceutical Science, 15th ed., Mack Publishing Company, Easton, Pa. (1980), which is incorporated herein by reference. The compositions comprising the present antibodies can be administered for prophylactic and/or therapeutic treatments. In therapeutic application, compositions can be administered to a patient already suffering from a disease, in an amount sufficient to cure or at least partially arrest the disease and its complications. An amount adequate to accomplish this is defined as a "therapeutically effective dose." Amounts effective for this use will depend upon the clinical situation and the general state of the patient's own immune system. For example, doses for preventing transplant rejection may be lower than those given if the patient presents with clinical symptoms of rejection. Single or multiple administrations of the compositions can be carried out with dose levels and pattern being selected by the treating physician. In any event, the pharmaceutical formulations should provide a quantity of the bioactive agents described herein sufficient to effectively treat the patient.

Dose administration can be repeated depending upon the pharmacokinetic parameters of the dosage formulation and the route of administration used. It is also provided that certain protocols may allow for one or more agents describe herein to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, olyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

The pharmaceutical compositions can be included in a container, pack, or dispenser together with instructions for administration. Kits for practice of the instant invention are also provided. For example, such a kit comprises a bioactive agent such as, e.g., an antibody reactive with B7x or BTLA, together with a means for administering the antibody conjugate, e.g., one or more syringes. The kit can come packaged with instructions for use.

G n Therapy

In a further aspect, the present invention provides compositions and methods for gene therapy.

Nucleic acids encoding B7x or BTLA polypeptides, as well as genetic antagonists or agonists of BTLA or B7x, may be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Nati. Acad. Sci. USA* 83, 4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

Diagnostic Uses

Mutations, deletions, duplications, and/or rearrangements that decrease B7x expression and/or activity lead to a loss of signaling that normally inhibits T cell activation. These may be germline or somatic changes. The functional consequence of this loss of inhibition is a hyperimmune state, characterized by autoimmune disease. Particularly affected are those tissues that harbor cells with the mutation and that show high levels of B7x expression normally, such as kidney, placenta, liver, lung and heart. The clinical manifestations of such B7x mutations may include autoimmune disoders such as e.g., diabetes, pre-eclampsia, rheumatoid arthritis, multiple sclerosis, and the like. Similarly, mutations, deletions, duplications, and/or rearrangements that decrease BTLA expression and/or activity lead to a loss of signaling that normally inhibits T cell activation. These may be germline or somatic changes. The functional consequence of this loss of inhibition is a hyperimmune state, characterized by autoimmune disease. Particularly affected are tissues that harbor antigens with which the affected T cells react, and that show high levels of B7x expression normally, such as kidney, placenta, liver, lung and heart. The clinical manifestations of such BTLA mutations may include autoimmune disorders.

In a preferred embodiment, the invention provides methods of diagnosing an autoimmune predisposition and/or disease. The methods involve measuring the expression and/or activity of BTLA and/or B7x.

Mutations, deletions, duplications, and/or rearrangements that increase B7x expression and/or activity lead to an increase in signaling that normally inhibits T cell activation. These may be germlne or somatic changes. The functional consequence of this increase in inhibitory signaling is a hypoimmune state, characterized by undesired cell growth and undesired cell survival.

As identified herein, B7x is highly expressed in a number of tumor cells. The high level of B7x expression allows such tumor cells to inhibit a T cell immune response that would otherwise be mounted against the tumor tissue.

Similarly, mutations, deletions, duplications, and/or rearrangements that increase BTLA expression and/or activity lead to an increase in signaling that normally inhibits T cell activation. These may be germline or somatic changes. The functional consequence of this increase in inhibitory signaling is a hypoimmune state, characterized by undesired cell growth, undesired cell survival, and increased susceptibility to disease caused by pathogens.

In one embodiment, the present invention provides methods of diagnosing a predisposition to cancer, or the existence or recurrence of cancer. The methods involve measuring the expression and/or activity of BTLA and/or B7x, either generally or in a tissue-specific fashion.

Modulation of Immune Responses

The present invention provides compositions and methods for modulating lymphocyte activity. As demonstrated herein, such compositions and methods are useful for modulating both Tc cell activity and Th cell activity, and in particular, Th-1 type T helper cells.

Surprisingly, also demonstrated herein is the expression of BTLA on activated B cells and its ability to inhibit B cell activity. B cells from mice lacking BTLA function exhibit increased responses to stimulation with anti-IgM, and BTLA deficient mice exhibit a three-fold increase in the amount of specific IgG1, IgG2a, and IgG2b isotypes as compared with control littermates. These observations are the first evidence of an inhibitory B cell activity for BTLA, which enables the use of agents that are capable of modulating BTLA activity to modulate B cell activity and antibody production. Accordingly, the invention also provides compositions and methods for modulating B cell activity and antibody production, which involve the use of agents capable of modulating BTLA activity.

Included among the preferred bioactive agents are B7x antibodies (anti-B7x antibodies), BTLA antibodies (anti-BTLA antibodies), B7x fusion proteins, BTLA fusion proteins, B7x proteins and fragments, BTLA proteins and fragments, peptides, and small molecule chemical compositions. Agonists of BTLA-mediated signaling, such as B7x proteins, B7x fusion proteins, and function activating anti-BTLA antibodies, may be used to stimulate BTLA and inhibit T and B cell activity. Conversely, antagonists of BTLA-mediated signaling, such as BTLA-Ig fusion proteins, function blocking anti-BTLA antibodies and anti-B7x antibodies, may be used to inhibit BTLA-mediated signaling, thereby preventing the attenuation of T and B cell activity mediated by BTLA signaling and, preferably, increasing T and B cell activity.

The anti-B7x antibodies provided herein specifically bind to B7x protein, and in particular, to one or more epitopes present in the extracellular domain of B7x identified above. The anti-BTLA antibodies provided herein specifically bind to BTLA protein, and in particular, to one or more epitopes present in the extracellular domain of BTLA identified above. Preferably, these antibodies effectively inhibit or interfere with the natural interaction between B7x and BTLA.

By inhibiting the interaction of BTLA and B7x, anti-B7x antibodies are used in a preferred embodiment to inhibit the suppression and/or attenuation of lymphocyte activity mediated by BTLA signaling.

By inhibiting the interaction of BTLA and B7x, function blocking anti-BTLA antibodies are used in a preferred embodiment to inhibit the suppression and/or attenuation of lymphocyte activity mediated by BTLA signaling. In an alternative embodiment, a function activating anti-BTLA antibody is used to stimulate BTLA, thereby mimicking the interaction of B7x, and promoting the suppression and/or attenuation of lymphocyte activity mediated by BTLA signaling.

The present invention provides methods of screening for bioactive agents capable of modulating the natural interaction between B7x and BTLA. In a preferred embodiment, the methods involve providing a B7x protein, a BTLA protein, and a candidate agent, and determining the binding of B7x to BTLA in the presence of the candidate agent. Agents that interfere with the binding of BTLA to B7x find use as antagonists of the natural interaction of BTLA-expressing and B7x-expressing cells. Accordingly, such agents find use as modulators of T cell activation. In some cases, an agent may mimic the action of B7x towards BTLA, or the action of BTLA towards B7x.

In one aspect, the present invention provides a medicament for the treatment of diseases associated with lymphocyte activity.

Antigens

As described herein, the compositions and methods provided herein find use in modulating lymphocyte activity in response to antigenic stimulation. Such antigenic stimulation can come from tumor-associated antigens, pathogen antigens and autoantigens. Antigenic stimulation caused by tumor-associated antigens and pathogen antigens may be a result of on-going malignancy or infection, and/or may be a result of vaccine antigens.

A wide variety of antigens may find use in conjunction with the compositions and formulations of the present invention. In particular, the adjuvant compositions provided herein may be advantageously combined with antigenic stimulation from tumor-associated antigens or pathogen antigens to increase lymphocyte activity against the corresponding tumor or pathogen. Generally, suitable antigens may be derived from proteins, peptides, polypeptides, lipids, glycolipids, carbohydrates and DNA found in the subject tumor or pathogen.

Tumor-associated antigens finding utility herein include both mutated and non-mutated molecules which may be indicative of a single tumor type, shared among several types of tumors, and/or exclusively expressed or overexpressed in tumor cells in comparison with normal cells. In addition to proteins and glycoproteins, tumor-specific patterns of expression of carbohydrates, gangliosides, glycolipids and mucins have also been documented.

Exemplary tumor-associated antigens for use in the subject cancer vaccines include protein products of oncogenes, tumor suppressor genes and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins and a number of other self proteins.

Specific embodiments of tumor-associated antigens include, e.g., mutated antigens such as the protein products of the Ras p21 protooncogenes, tumor suppressor p53 and HER-2/neu and BCR-abl oncogenes, as well as CDK4, MUM1, Caspase 8, and Beta catenin; overexpressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor-associated antigens herein are whole cell and tumor cell lysates as well as immunogenic portions thereof, as well as immunoglobulin idiotypes expressed on monoclonal proliferations of B lymphocytes for use against B cell lymphomnas.

Tumor-associated antigens and their respective tumor cell targets include, e.g., cytokeratins, particularly cytokeratin 8, 18 and 19, as antigens for carcinoma. Epithelial membrane antigen (EMA), human embryonic antigen (HEA-125), human milk fat globules, MBr1, MBr8, Ber-EP4, 17-1A, C26 and T16 are also known carcinoma antigens. Desmin and muscle-specific actin are antigens of myogenic sarcomas. Placental alkaline phosphatase, beta-human chorionic gonadotropin, and alpha-fetoprotein are antigens of trophoblastic and germ cell tumors. Prostate specific antigen is an antigen of prostatic carcinomas, carcinoembryonic antigen of colon adenocarcinomas. HMB-45 is an antigen of melanomas. In cervical cancer, useful antigens could be encoded by human papilloma virus. Chromagranin-A and synaptophysin are antigens of neuroendocrine and neuroectodermal tumors. Of particular interest are aggressive tumors that form solid tumor masses having necrotic areas. The lysis of such necrotic cells is a rich source of antigens for antigen-presenting cells, and thus the subject compositions and methods may find advantageous use in conjunction with conventional chemotherapy and/or radiation therapy.

Tumor-associated antigens can be prepared by methods well known in the art. For example, these antigens can be prepared from cancer cells either by preparing crude extracts of cancer cells (e.g., as described in Cohen et al., Cancer Res., 54:1055 (1994)), by partially purifying the antigens, by recombinant technology, or by de novo synthesis of known antigens. The antigen may also be in the form of a nucleic acid encoding an antigenic peptide in a form suitable for expression in a subject and presentation to the immune system of the immunized subject. Further, the antigen may be a complete antigen, or it may be a fragment of a complete antigen comprising at least one epitope.

Antigens derived from pathogens known to predispose to certain cancers may also be advantageously utilized in conjunction with the compositions and methods provided herein. It is estimated that close to 16% of the worldwide incidence of cancer can be attributed to infectious pathogens, and a number of common malignancies are characterized by the expression of specific viral gene products. Thus, the inclusion of one or more antigens from pathogens implicated in causing cancer may help broaden the host immune response and enhance the prophylactic or therapeutic effect of the cancer vaccine. Pathogens of particular interest for use herein include the hepatitis B virus (hepatocellular carcinoma), hepatitis C virus (heptomas), Epstein Barr virus (EBV) (Burkitt lymphoma, nasopharynx cancer, PTLD in immunosuppressed individuals), HTLV1 (adult T cell leukemia), oncogenic human papilloma viruses types 16, 18, 33, 45 (adult cervical cancer), and the bacterium Helicobacter pylori (B cell gastric lymphoma).

Also contemplated herein are pathogen antigens derived from infectious microbes such as virus, bacteria, parasites and fungi and fragments thereof, in order to increase lymphocyte activity in response to active infection or improve the efficacy of prophylactic vaccine therapy. Examples of infectious virus include, but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Also, gram negative and gram positive bacteria serve as antigens in vertebrate animals. Such gram positive bacteria include, but are not limited to *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to: *Helicobacterpyloris, Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus (viridans* group), *Streptococcusfaecalis, Streptococcus bovis, Streptococcus (anaerobic* sps.), *Streptococcus pneumoniae*, pathogenic *Campylobacter* sp., *Enterococcus* sp., *Haemophilus infuenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia*, and *Actinomyces israelli*.

Examples of pathogens also include, but are not limited to, infectious fungi that infect mammals, and more particularly humans. Examples of infectious fingi include, but are not limited to: *Cryptococcus neoformans, Histoplasma capsulatum, Coccidioides immitis, Blastomyces dermatitidis, Chlamydia trachomatis, Candida albicans*. Examples of infectious parasites include *Plasmodium* such as *Plasmodium falciparum, Plasmodium malariae, Plasmodium ovale*, and *Plasmodium vivax*. Other infectious organisms (i.e. protists) include *Toxoplasma gondii*.

Other medically relevant microorganisms that serve as antigens in mammals and more particularly humans are described extensively in the literature, e.g., see C. G. A Thomas, Medical Microbiology, Bailliere Tindall, Great Britain 1983, the entire contents of which is hereby incorporated by reference. In addition to the treatment of infectious human diseases, the compositions and methods of the present invention are useful for treating infections of non-human mammals. Many vaccines for the treatment of non-human mammals are disclosed in Bennett, K. Compendium of Veterinary Products, 3rd ed. North American Compendiums, Inc., 1995.

Treatment of Autoimmune Disease

The present invention also provides compositions and methods for inhibiting autoimmune responses. In a preferred embodiment, compositions and methods for inhibiting the activity of autoreactive T and B cells that specifically recognize autoantigens are provided. Desirably, these compositions and methods may be used to inhibit killing of non-tumor cells mediated by one or more autoantigens.

Preferred compositions for use in the treatment of autoimmune disease comprise the agonists of BTLA-mediated signaling described herein including, e.g., the above-described mimicking agents. Especially preferred agents include B7x protein fragments comprising the B7x extracellular domain, or a portion thereof; B7x-Ig fusion proteins comprising the B7x extracellular domain, or a portion thereof; function-activating anti-BTLA antibody; peptides that mimic B7x (mimetics); and small molecule chemical compositions that mimic the natural interaction of BTLA and B7x. Also preferred are compositions capable of binding to both BTLA and TCR, either in a cross-linking fashion or as polyclonal mixtures.

Also contemplated in the present invention are genetic approaches to autoimmune disease. Particularly, gene therapy may be used to increase the level of BTLA expression on T cells, and/or increase the level of expression of B7x on non-lymphoid cells that are subject to attack by autoreactive lymphocytes. The use of isoforms of BTLA and B7x that exhibit elevated specific activity is also contemplated, the object of each method being to potentiate signaling that is suppressive to T cell activation.

Also provided herein are methods of screening for bioactive agents that increase the level and/or activity of B7x. Further provided are methods of screening for bioactive agents that increase the level and/or activity of BTLA. The present invention contemplates the use of such agents to treat autoimmune diseases, the object being to potentiate signaling that is suppressive to lymphocyte activity.

In one aspect, the present invention provides a medicament for the treatment of autoimmune disease.

Treatment of Cancer

The present invention also provides compositions and methods for treating cancer, and in particular, for increasing the activity of BTLA-positive lymphocytes against B7x-positive tumor cells. In a preferred embodiment, compositions and methods for increasing the T cell response to tumor-associated antigens other than B7x are provided. Desirably, these compositions and methods may be used to inhibit the growth of tumor cells capable of expressing B7x.

Preferred compositions for use in the treatment of cancer are the antagonists of BTLA-mediated signaling described herein including, e.g., BTLA or B7x blocking agents. Especially preferred agents include anti-B7x antibodies; protein fragments comprising the BTLA extracellular domain, or a portion thereof; BTLA-Ig fusion proteins comprising the BTLA extracellular domain, or a portion thereof; function-blocking anti-BTLA antibody; peptides that mimic BTLA (mimetics); and small molecule chemical compositions that interfere with the natural interaction of BTLA and B7x.

Also contemplated in the present invention are genetic approaches to the treatment of cancer. Particularly, gene therapy may be used to decrease the level of BTLA expression on T cells, and/or decrease the level of expression of B7x on tumor cells. The use of isoforms of BTLA and B7x that exhibit dominant negative activity is also contemplated, the object of each method being to inhibit signaling that is normally suppressive to T cell activation. Genetic approaches may involve the use of tissue and cell specific promoters to target expression of BTLA and/or B7x dominant negative variants, antisense nucleic acids, or small inhibitory RNAs to T cells and tumor cells, respectively. The methods may additionally involve the use of tumor-targeted viruses, or other delivery vehicles that specifically recognize tumor cells. The methods may additionally involve the use of T cell-targeted viruses, or other delivery vehicles that specifically recognize T cells.

Also provided herein are methods of screening for bioactive agents that decrease the level and/or activity of B7x. Further provided are methods of screening for bioactive agents that decrease the level and/or activity of BTLA. The present invention contemplates the use of such agents to treat cancer, the object being to inhibit signaling that normally attenuates the lymphocytic response to tumor antigens and tumor tissues.

Particularly preferred are agents that may be selectively targeted to tumor cells, and effect a decrease in B7x expression in tumor cells without reducing the level of B7x expression in non-tumor cells to deleterious levels. Highly preferred are agents that have a precursor form. These "prodrugs" are converted to their active form in the vicinity of tumor tissue typically by an enzymatic activity that is restricted in its distribution to the vicinity of the tumor.

Also highly preferred are agents that can be combined with targeting moieties that selectively deliver the agent to a tumor. These targeting moieties provide a high local concentration of the agent in the vicinity of the tumor tissue, and reduce the amount of agent that must be administered to effect the desired response.

Also contemplated in the present invention is the use of combination therapy to treat cancer, as described above.

In a preferred embodiment, immunization is done to promote a tumor-specific T cell immune response. In this embodiment, a bioactive agent that inhibits BTLA activation is administered in combination with a tumor-associated antigen other than B7x. The combination of a tumor-associated antigen and a BTLA-inhibitory/B7x functional-mimetic promotes a tumor specific T cell response, in which T cells encounter a lower level of inhibition than exerted by the tumor tissue in the absence of the bioactive agent.

In one aspect, the present invention provides a medicament for the treatment of cancer.

Promote Graft Survival

The present invention also provides compositions and methods for modulating normal but undesired immune responses involving T and B cell activity. In a preferred embodiment, compositions and methods for inhibiting the host lymphocyte response to transplanted tissue and organs are provided. Desirably, these compositions and methods may be used to prolong the survival of grafted tissue.

Preferred compositions for use in the prevention of acute and/or chronic graft rejection comprise the agonists of BTLA-mediated signaling described herein including, e.g., the above-described mimicking agents. Especially preferred agents include B7x polypeptides comprising the B7x extracellular domain, or a portion thereof; B7x-Ig fusion proteins comprising the B7x extracellular domain, or a portion thereof; function-activating anti-BTLA antibodies; peptides that mimic B7x (mimetics); and small molecule chemical compositions that mimic the natural interaction of BTLA and B7x.

In addition to their utility in general immunosuppressive strategies, the subject agonists of BTLA-mediated signaling described herein may also have important implications for tolerance induction in tissue and organ transplantation, by biasing the recipient T helper cell immune response away from an unfavorable Th-1-type response and towards a more favorable Th-2 type response. As demonstrated herein, BTLA is highly expressed in Th-1 type T cells in comparison with low expression in Th-2 type T cells after T cell polarization, and thus the subject agonists will preferentially attenuate the activity of Th-1 cells over Th-2 cells. Recent evidence suggests that the creation of a Th-2 type cytokine milieu can be more favorable to tolerance induction, and thus the need for life-long immunosuppressive therapy in transplant patients may be reduced or eliminated by employing the compositions and methods described herein.

In one aspect, the present invention provides a medicament for use in transplantation and immune suppression.

EXAMPLES

EXAMPLES

Methods for Examples 1-3

Mice and cells. Female BALB/c were purchased from Jackson Laboratories (Bar Harbor, Me.) and were used at ages 6-9-weeks-old. Animals were housed in accordance with the Animal Care and Use Committee regulations at the University of California, Berkeley. All cell purifications were performed with magnetic cell sorting separation columns (Milternyi Biotec, Auburn, Calif.) with purities >95%. Macrophages were obtained from peritoneal cavity. All cells were cultured in DMEM supplemented with 10% fetal calf serum, 2 µM L-glutamine, and 100 U/ml penicillin and streptomycin (all from BioWhittaker), and 2 µM 2-mercaptoethanol (Sigma).

Production of fusion protein. B7xIg was prepared by fusing the coding region of the extracellular domain of B7x to a chimeric sequence containing the CH2-CH3 domain of mouse IgG1 and a Myc-His-tag in pcDNA4 (a gift from Dr. William Sha, UC Berkeley). The construct was linearized with Bgl II and transfected into 293T cells with FuGENE 6 Transfection Reagent (Roche, Ind.). Stable transfectants were selected in 1 mg/ml of Zeocin (Invitrogen). To produce fusion protein, stable transfectants were cultured in serum-free DMEM for 72 h, the supernatant was collected and B7xIg was purified by affinity column chromatography over His-Bind resin (Novagen). The purity of the fusion protein was confirmed by SDS-PAGE and by immunoblotting with antibodies against Myc and mouse IgG.

Northern blot analysis. Mouse and human multiple tissue northern blots (Clontech) were probed with cDNA fragments labeled by $^{32}$p-dCTP with Random Primed DNA Labeling kit (Roche). Mouse and human B7x probes consisted of the entire coding regions. β-actin probes were supplied by Clontech. Blots were hybridized for 1 h at 68° C., washed twice at room temperature in 2×SSC containing 0.05% SDS, followed by 0.1×SSC containing 0.1% SDS at 50° C. and examined on an PhosphorImager.

RT-PCR, and retrovirus constructs. Total RNA was isolated using TRI Reagent (Sigma). Reverse transcription was performed using oligo(dT) as the first primer and 2 µg of total RNA with Omniscript Reverse Transcriptase Kit (GIAGEN). RT-PCR was performed using HotStarTag (QIAGEN). B7x-GFP fusion protein constructs were generated using PCR to amplify the coding sequence of B7x without the stop codon and then cloned into the pEGFPN3 vector (Clontech). Following confirmation by DNA sequencing, the constructs of B7x-GFP fusion protein or GFP alone were cloned into a mouse stem cell virus (MSCV) retroviral expression vector (a generous gift from Dr. William Sha, UC Berkeley). Retrovirus was produced by transient transfection of the Pheonix-GP packaging cell line. For infection of CHO cells, retroviruses were pseudotyped with vesicular stomatitis virus G-glycoprotein. Stable clones were selected by flow cytometric single cell sorting. For experiments using B7.2 only or B7.2/B7x cotransfected cells, the transfectants were matched for B7.2 expression levels.

CHO cell stimulation of T cells. CHO cells transfected with vector were incubated with mitomycin C (50 µg/ml, Sigma) for 16 h. The cells were treated with PBS-EDTA(10 mM), washed twice, resuspended in complete DMEM and left on ice for 2 h. The cells were subsequently washed twice and resuspended in completed DMEM. Purified T cells ($10^5$/well) were incubated with mitomycin-treated CHO transfectants ($10^5$/well) in anti-CD3 (500A2)-bound-96-well plates. To analyze T cell proliferation, cultures were pulsed with 1 µCi/well of [$^3$H]thymidine for the last 16 h of a 72-h incubation.

Cytokines ELISA. Aliquots of supernatants were collected at 48 h after initiation of cell cultures. IL-2, IL-4, IFN-γ and IL-10 were measured with monoclonal antibodies and recombinant cytokine standards from PharMingen.

Flow cytometry. After incubation with the anti-Fc receptor antibody 24G2 for Fc receptor-blocking, cells were stained with B7x-Ig or mouse IgG1 as a control for 45 min on ice and then stained with an anti-mouse-IgG PE-conjugate (Caltag) for 30 min. In some experiments, cells were stained with PE-conjugated anti-ICOS (eBioscience), anti-F480 (eBioscience), anti-CD4 and anti-CD8 (Caltag); or biotin-conjugate anti-B7.2 (Pharmingen), anti-CD28 (Pharmingen), anti-PD-1 (eBioscience), and then stained with PE-Streptavidin (Caltag). The cells were analyzed on an XL (Coulter Electronics, Hialeah, Fla.)

CSFE staining and analyses. Purified T cells ($10^7$/ml) were washed with HBSS, labeled with 2.5 µM CSFE (Molecular Probes, OR) for 10 min at 37° C., and then washed twice with cold completed DMEM. T cells were stimulated with plate-bound anti-CD3 500A2 and the indicated CHO transfectants. On day 4 of culture, cells were stained with PE-anti-CD4 or PE-anti-CD8, and analyzed by flow cytometry Example 1

Expression of B7x

Figure 7:
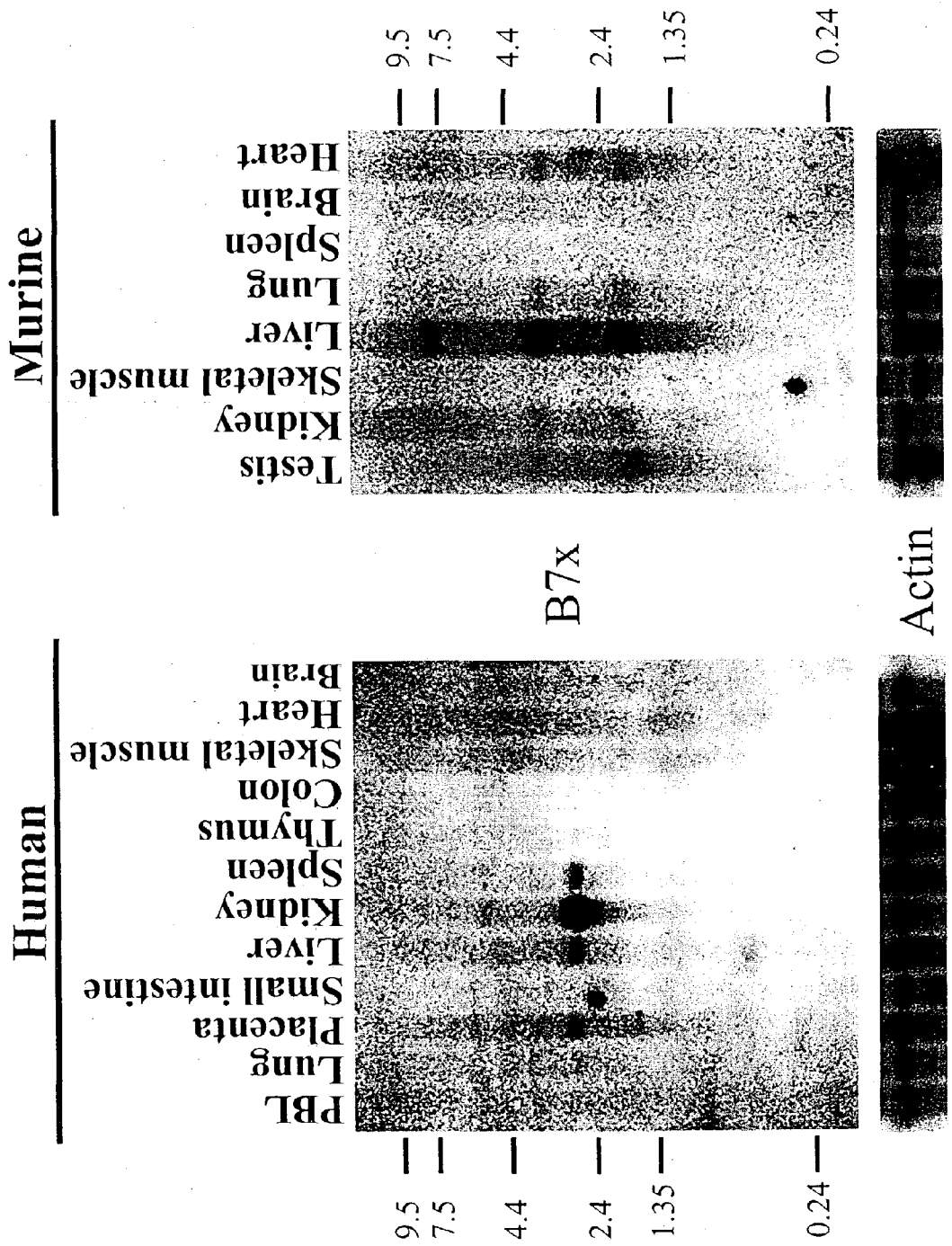
FIG. 7 shows Northern blot analysis of human poly(A) RNA (left panel) and mouse poly(A) RNA (right panel) from a variety of tissues with B7x and actin cDNA probes.
Figure 8:
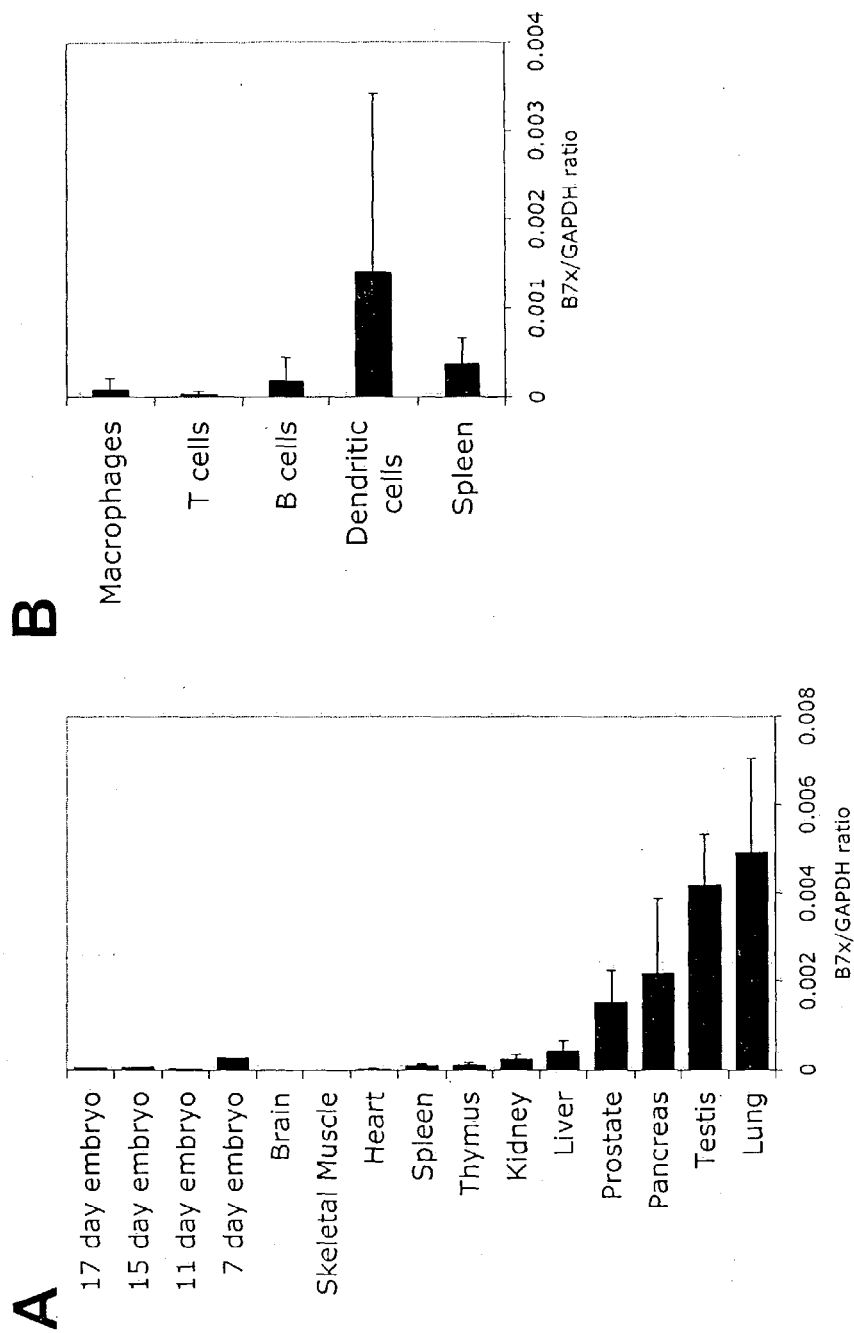
FIG. 8 shows RT-PCR analysis of B7x mRNA expression in a variety of mouse tissues and immune cells. (A) Real timePCR was performed on cDNA from multiple mouse tissues. cDNA from the Clontech Mouse MTC panel I was used as well as cDNA made from tissues dissected out of 2 C57/BL6 mice. The results shown are the average and standard deviation between the 3 mouse cDNA samples. (B) Real time PCR was performed on CD11c+ Denndritic cells, B cells and T cells that were purified from the spleen and compared to the whole spleen. Thioglycolate induced macrophages were purified by overnight adherence and removal of non-adherent cells. The results shown represents the average and standard deviation between 4-10 individual mouse samples.

The expression of B7x mRNA in human and mouse tissues was analyzed by Northern blot hybridization. Human B7x was present in a single 3.2-kb mRNA readily detectable in kidney, liver, spleen and placenta. Mouse B7x had three transcripts of 1.9, 3.5 and 8.2 kb, and was expressed significantly in liver, testis, kidney, lung and heart (FIG. 7). With RT-PCR, B7x mRNA was also detected in mouse spleen, prostate, lymph node, thymus, eye, pancreas, B cells, T cells, macrophages, and dendritic cells. (FIG. 8, and data not shown).

Figure 9:
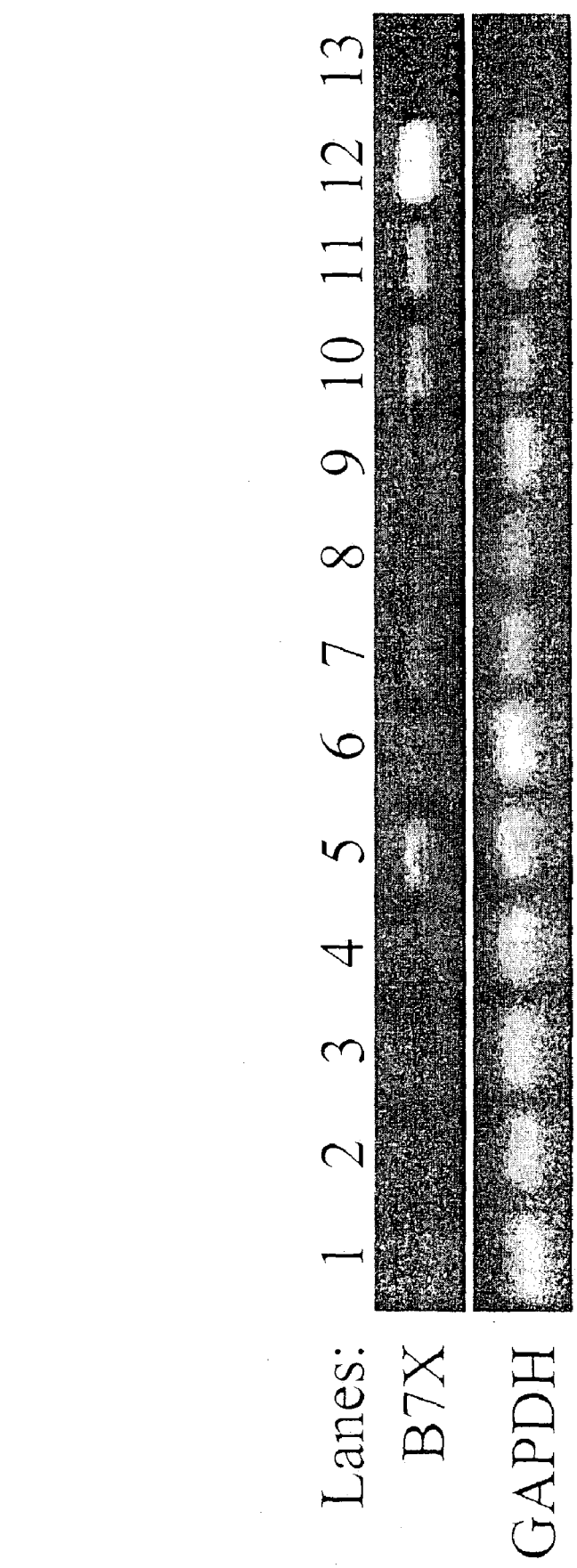
FIG. 9 shows shows RT-PCR analysis of B7x mRNA expression in a variety of tumor cells. Lanes: 1: EL4, 2:B16BL6, 3: B16F10, 4: Lewis lung carcinoma, 5: TRAMP C2, 6:MC38, 7: SA1/N, 8: SM1, 9: C6VL, 10: DC2.4, 11: CHO cells, 12: CHO cells transfected with B7x gene, 13: no DNA control.

Interestingly, 5 of 8 mouse B7x ESTs located in database searches had been derived from mammary tumors, and 3 of 6 human B7x ESTs originated from ovarian and uterine tumors. To determine whether expression of B7x might be a regular feature of tumors, we used Northern blot analysis to examine a panel of mouse tumors for B7x mRNA expression. Most of the tumor cell lines tested, including NB41A3 (neuroblastoma), P815 (mastocytoma), L1210 (lymphocytic leukemia), R1.1 (T lymphoma), Hepa 1-6 (hepatoma), P19 (teratocarcinoma), M-MSV-BALB/3T3 (fibroblast transformed by Moloney murine sarcoma virus), K-BALB (fibroblast transformed by Kirsten murine sarcoma virus) and RAW264.7 (macrophage tumor) expressed readily detectable B7x transcript (data not shown). In addition, RT-PCR analysis of B7x mRNA expression revealed tha B7x is expressed in a variety of tumor cells (FIG. 9).

Figure 10:
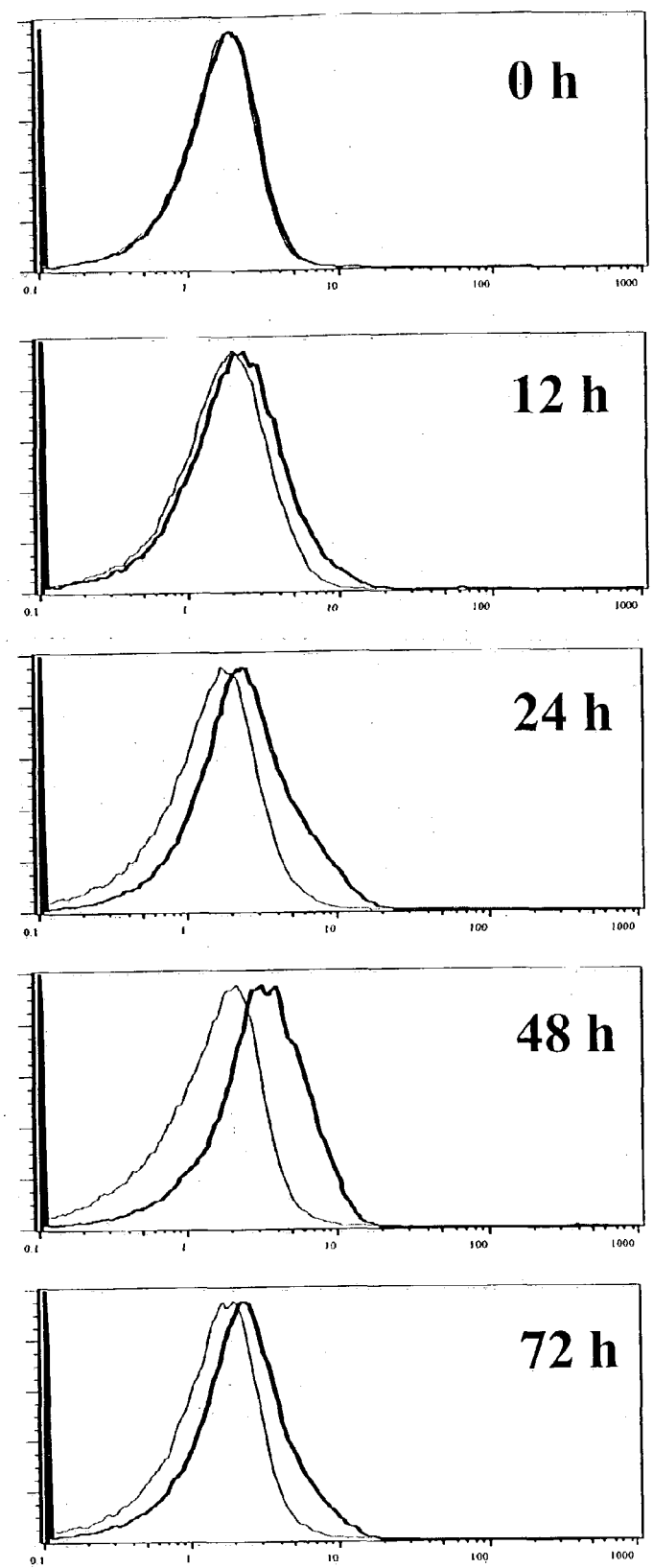
FIG. 10 shows activated CD4+ T cells stained with B7xIg fusion protein (open histograms) or control mouse IgG1 (shaded histograms).
Figure 11:
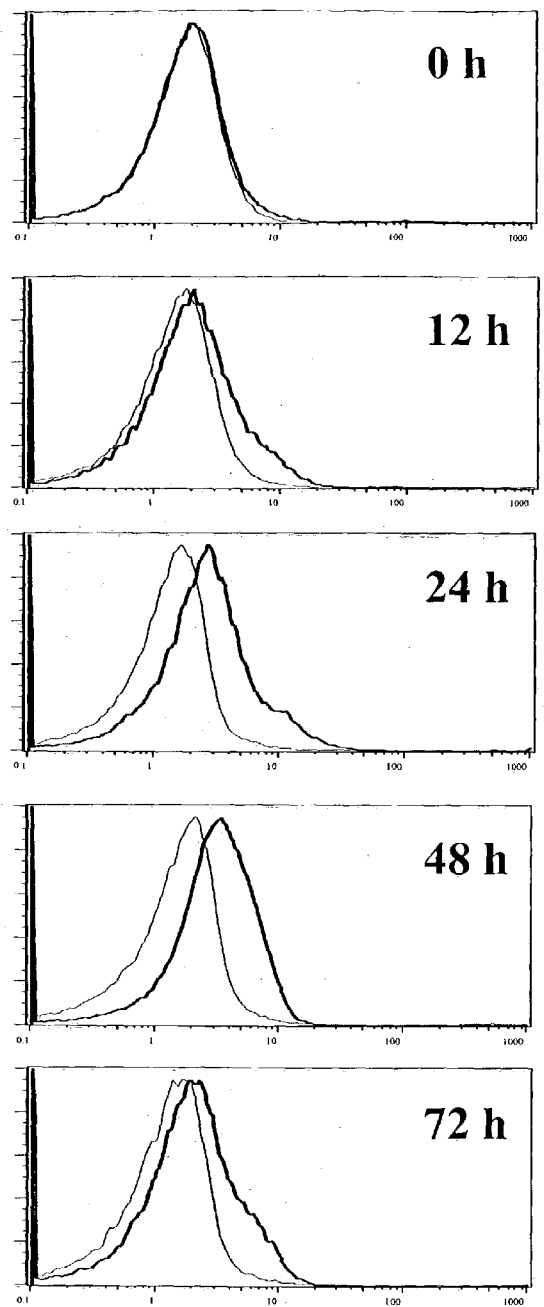
FIG. 11 shows activated CD8+ T cells stained with B7x-Ig fusion protein (open histograms) or control mouse IgG1 (shaded histograms).

To determine if T cells express a B7x counterreceptor, we performed flow cytometric analyses with a B7xIg fusion protein prepared by linking the extracellular domain of B7x to the CH2-CH3 domains of mouse IgG1. Resting T cells did not bind B7x-Ig. However, stimulation of T cells with PMA (50 ng/ml) and ionomycin (1 µg/ml) resulted in rapid acquisition of B7x binding on both CD4 and CD8 T cells within 12 hours of stimulation (FIGS. 10 and 11). These results suggest that a receptor for B7x is rapidly induced on both CD4 and CD8 T cells in response to stimulation.

Figure 12:
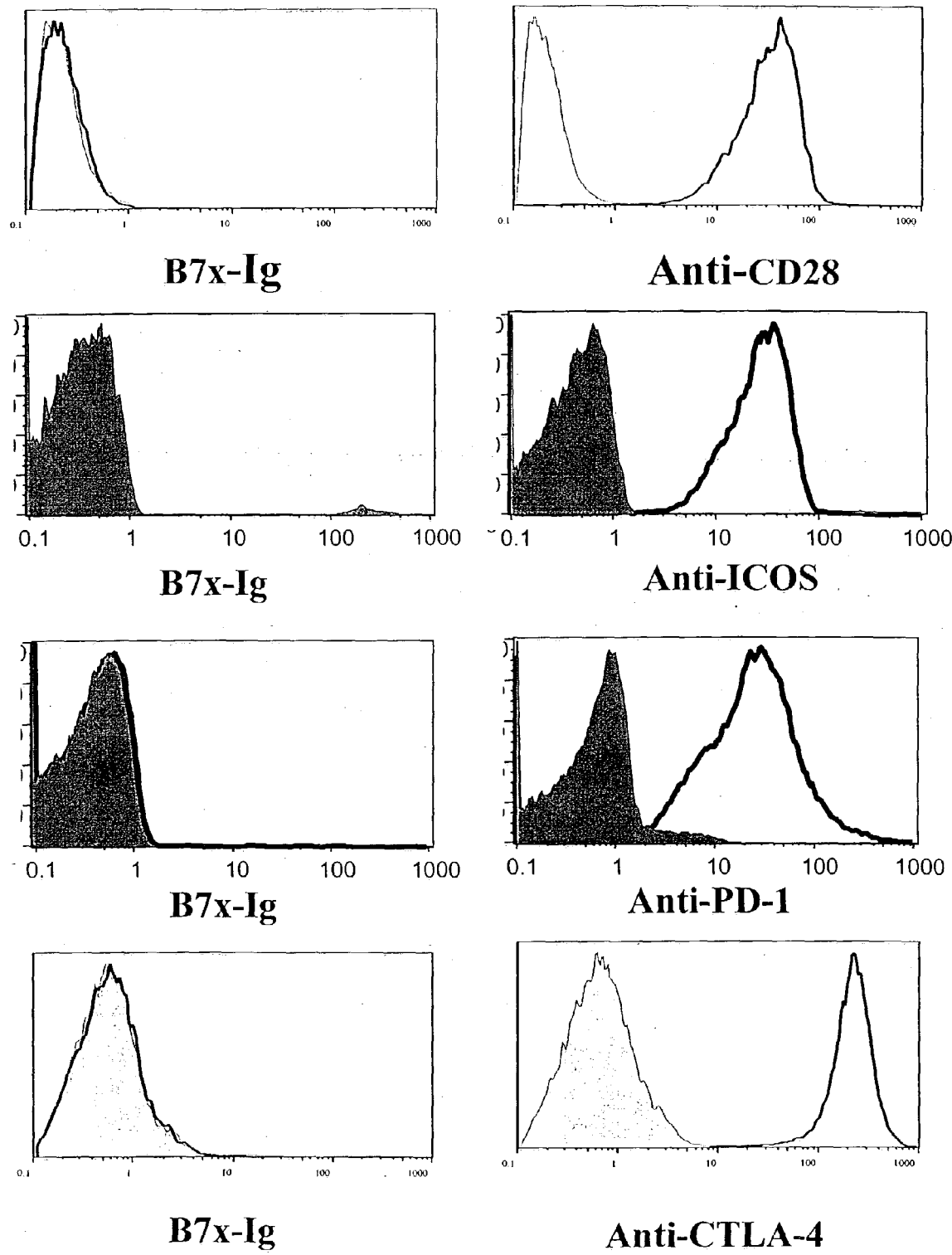
FIG. 12 shows 293 cells (shaded histograms), and transfected 293 cells expressing CD28, ICOS, or PD-1 (open histograms), and DT320 cells expressing CTLA-4(open histograms), stained with B7xIg fusion protein or control antibody (anti-CD28, anti-ICOS, anti-PD-1, anti-CTLA-4).

Having determined that T cells express a counter-receptor for B7x, we next examined the possibility that this receptor might be one of the T cell surface molecules know to bind other B7 family members. B7xIg failed to bind to transfected 293 cells expressing high levels of CD28, CTLA-4, ICOS, or PD-1 (FIG. 12). Thus, B7x binds to an activation-induced counter-receptor on T cells that is distinct from the known CD28 family members.

Example 2

B7x Inhibits T cell Activation Processes

Figure 14:
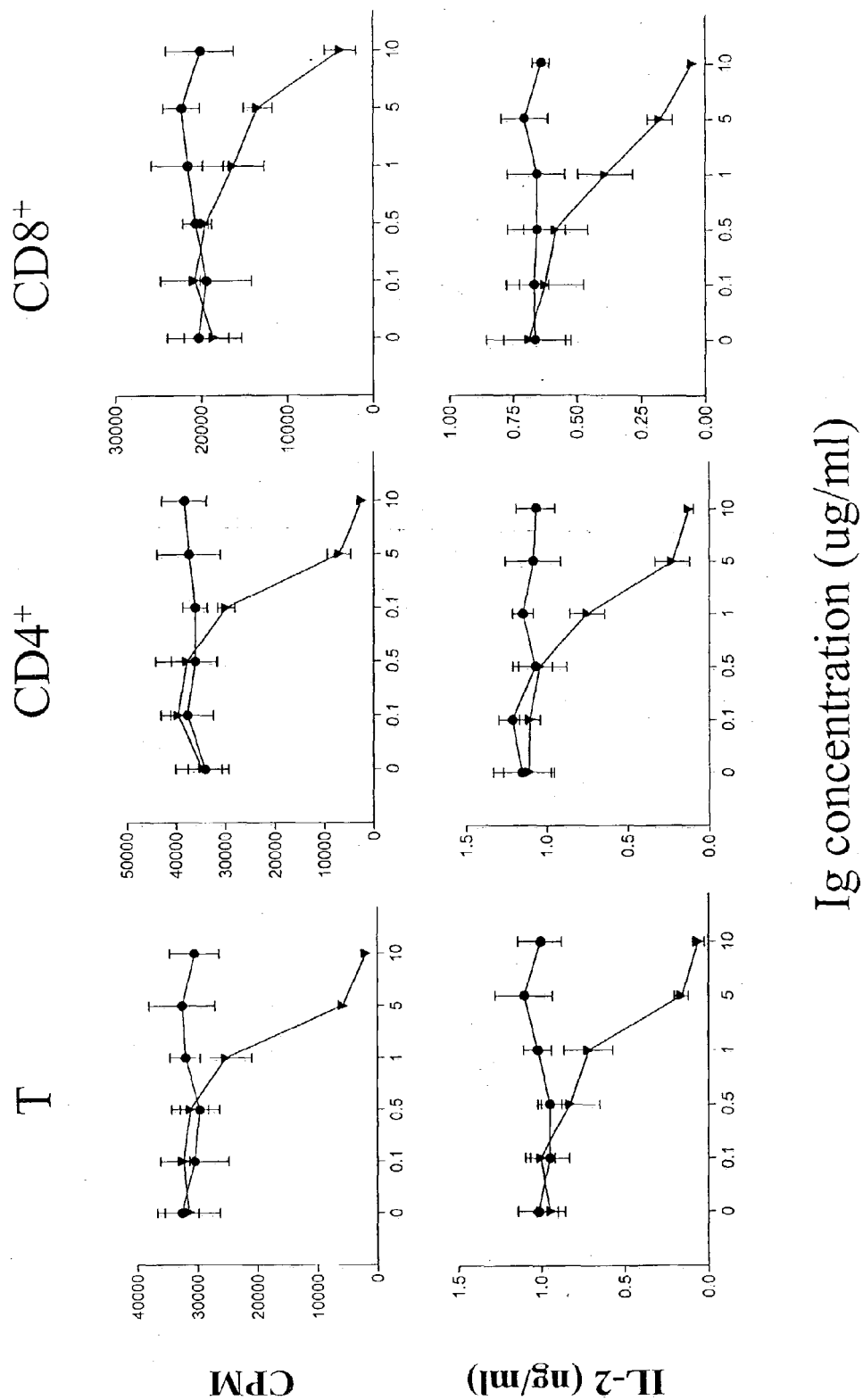
FIG. 14 is a series of graphs representing the results from experiments in which murine T cells, and T cell subsets (CD4+ and CD8+) were stimulated with plate-bound anti-CD3 and varied amounts of plate-bound B7x-Ig (▼) or control Ig (•). IL-2 production and $^3$H-thymidine incorporation were measured.
Figure 15:
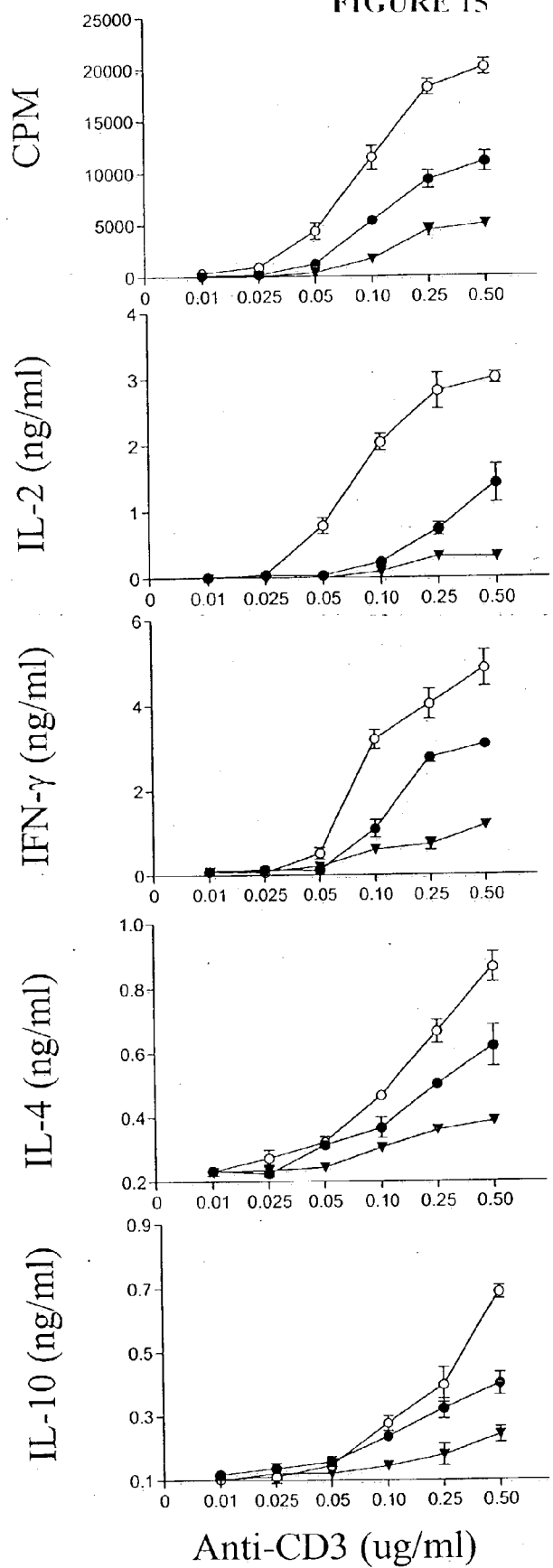
FIG. 15 is a series of graphs representing the results from experiments in which purified T cells were stimulated with varied amounts of plate-bound anti-CD3 and CHO transfectants expressing GFP (•), B7.2 (O) or B7x (▼). The production of IL-10, IL-4, IFN-γ, and IL-2, and the incorporation of and $^3$H-thymidine were measured.
Figure 16:
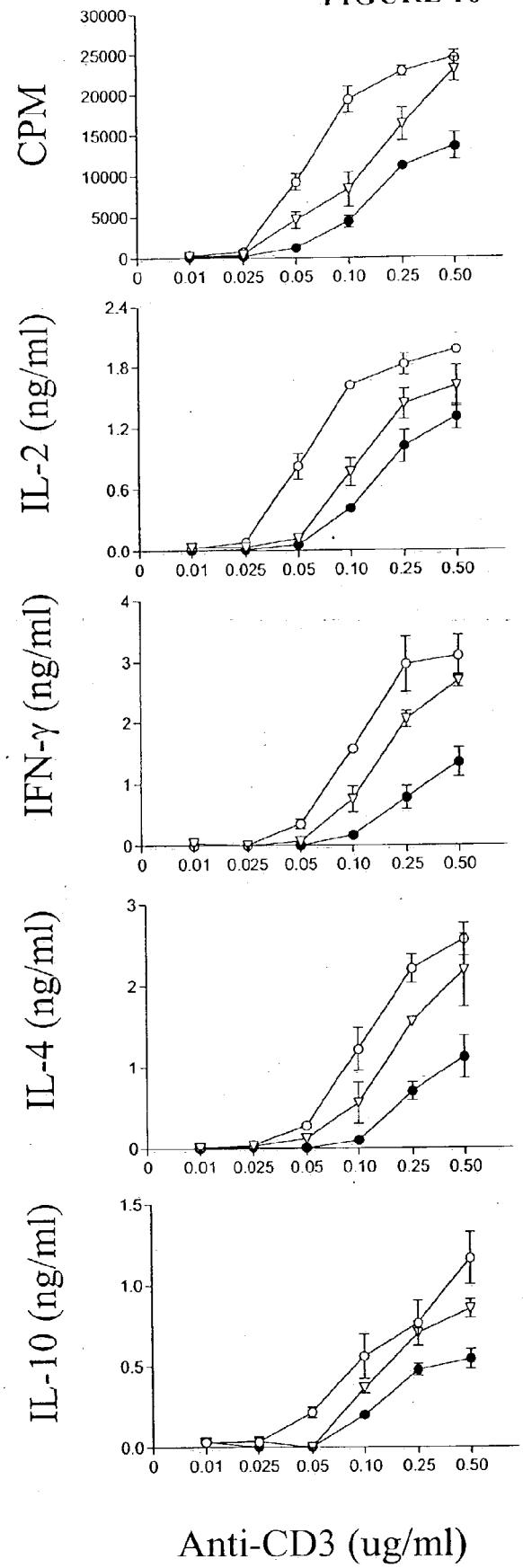
FIG. 16 is a series of graphs representing the results from experiments in which murine T cells were stimulated with varied amounts of plate-bound anti-CD3 and CHO transfectants expressing GFP (•), B7.2 (O) or B7x/B7.2(V). The production of IL-10, IL-4, IFN-γ, and IL-2, and the incorporation of and $^3$H-thymidine were measured.

Initial experiments used purified T cells activated with plate-bound anti-CD3 in the presence of different amounts of immobilized B7xIg. B7xIg decreased proliferation and IL-2 production in a dose-dependent fashion. Additional experiments with purified T cell subsets showed that B7xIg inhibited both CD4 and CD8 T cell responses (FIG. 14). We next employed a conventional costimulation assay. Purified T cells were activated with different amounts of plate-bound anti-CD3 in the presence of CHO transfectants expressing either GFP, B7.2 or B7x. As expected, T cells stimulated in the presence of B7.2/CHO exhibited enhanced proliferation and cytokine production compared to control GFP/CHO. In contrast, B7x/CHO significantly reduced T cell proliferation and cytokine production (FIG. 15). In order to determine the effect of B7x on T cell activation in the face of costimulation, we also used CHO cells which expressed B7.2 or coexpressed B7.2 and B7x. The presence of B7x resulted in a partial inhibition of proliferation and cytokine production by B7.2-costimulated T cells, an effect that was more pronounced at lower levels of anti-CD3 (FIG. 16). Together these results show that B7x can strongly inhibit TCR-mediated T cell proliferation and cytokine production, even in the presence of CD28-mediated costimulation.

Example 3

B7x Limits the Number and the Division Rate of T cells That Enter Cell Cycle

Having determined that B7x has a potential counter-receptor on T cells and that the interaction of B7x with its receptor leads to a dramatic inhibition of T cell activation, we further investigated the mechanism of B7x action. T cells were labeled with carboxyfluorescein diacetate succinimidyl ester (CSFE) and stimulated with various CHO transfectants with or without plate-bound anti-CD3. Cells were harvested on day 4 and stained for CD4 and CD8 expression. B7x-mediated inhibition was determined by electronically gating on CD4+ or CD8+ T cells populations and measuring CFSE fluorescence intensity (FIGS. 17 and 18). T cells did not divide when incubated with GFP/CHO only. When stimulated with anti-CD3 and GFP/CHO, T cells went through at least 7-8 divisions, with most CD4+ and CD8+ T cells dividing more than 2 times. However, when T cells were incubated with anti-CD3 and B7x/CHO, they were limited to 3-4 divisions. Further, only about 1% of T cells did not divide when stimulated with anti-CD3, whereas 31.4% of CD4+ and 34.3% of CD8+ T cells could not divide in the presence of B7x. These differences in the number of divisions as well as the percentage of non-dividing cells indicate that the interaction of B7x and its receptor on T cells leads to decreased proliferation by limiting the number and the division rate of both CD4+ and CD8+ T cells that enter cell cycle.

Further Description of FIGS. 14-18

FIG. 14: T cells, and T cell subsets (CD4+ and CD8+) from BALB/c mice were stimulated with plate-bound anti-CD3 (0.25 mg/ml for CD4+ and total T cells; 2 ug/ml for CD8+ T cells) and plate-bound B7x-Ig (▼) or control Ig (•) (FIG. 14). IL-2 production and $^3$H-thymidine incorporation were measured. The results revealed that B7x inhibits TCR-mediated T cell responses, particularly cytokine production and proliferation. Error bars in FIG. 14 indicate standard deviation of triplicate cultures. The data presented in FIG. 14 are representative of three independent experiments.

FIG. 15: Purified T cells were stimulated with plate-bound anti-CD3 and CHO transfectants expressing GFP (•), B7.2 (O) or B7x (▼) (FIG. 15). Aliquots of supernatants were collected at 48 h after initiation of cultures and cytokines (IL-10, IL-4, IFN-γ, and IL-2) measured by ELISA, and cell proliferation was measured after 72 h with [$^3$H]thymidine incorporation. The results reveal that B7x inhibits TCR-mediated T cell responses, particularly cytokine production and proliferation. The error bars in FIG. 15 indicate standard deviation of triplicate cultures. The data in FIG. 15 are representative of five independent experiments.

FIG. 16: T cells purified from BALC/c mice were stimulated with plate-bound anti-CD3 and CHO transfectants expressing GFP (•), B7.2 (O) or B7x/B7.2(▼). The production of IL-10, IL-4, IFN-γ, and IL-2, and the incorporation of and $^3$H-thymidine were measured (FIG. 16). Aliquots of supernatants were collected at 48 h after initiation of cultures and cytokines measured by ELISA. Proliferation was measured after 72 h with [$^3$H]thymidine incorporation. The error bars in FIG. 16 indicate standard deviation of triplicate cultures. The data in FIG. 16 are representative of three independent experiments.

FIG. 17: T cells were labeled with CSFE and stimulated with or without plate-bound anti-CD3 (0.25 mg/ml) and CHO transfectants expressing GFP or B7x. On day 4, cells were harvested, stained with PE-anti-CD4 and analyzed by flow cytometry (FIG. 17). The results reveal that B7x limits the number and division rate of T cells that enter the cell cycle. Percentages in FIG. 17 refer to fraction of cells in the non-dividing peak or divided more than 2 times. The data in FIG. 17 are representative of three independent experiments. These data show that B7x limits the number and division rate of CD4+ T cells that enter the cell cycle.

FIG. 18: T cells were labeled with CSFE and stimulated with or without plate-bound anti-CD3 (0.25 mg/ml) and CHO transfectants expressing GFP or B7x. On day 4, cells were harvested, stained with PE-anti-CD8 and analyzed by flow cytometry. Percentages refer to fraction of cells in the non-dividing peak or divided more than 2 times. These data are representative of three independent experiments. These data show that B7x limits the number and division rate of CD8+ T cells that enter the cell cycle.

General Materials and Methods for Examples 4-9

Plasmid constructions. Myc-tagged BTLA constructs were prepared as follows. The open reading frame of mBTLAs was amplified from a colony obtained from screening a DO11.10 TH1 cDNA library with primers J10-RV1-Bgl2 (5'-AGCTCTGAAGATCTCTAGGGAGGAAG-3') (SEQ ID NO:28) and J10-Xho1 (5'.-CATGCTCGAGGAAGGTC-CAGACAGAGGTATTG-3'.) (SEQ ID NO:29). The product was digested with BglII and XhoI and cloned into the IRES-GFP-RV retrovirus48 at the BglII and XhoI sites to produce mBTLAs-RV. The N-terminal Myc-tagged version of mBTLAs (Myc3-mBTLAs-RV) contains a triple Myc tag inserted downstream of the signal peptide. To produce this construct, a PCR product containing the mBTLA signal sequence and 3. overhang homologous to the Myc tag was prepared with mBTLAs-RV as the template and primers J10-RV1-Bgl2 and J10-A2 (5.GTTCAGATCCMGGAT-GCTCCAGAGGCCC-3.) (SEQ ID NO:30). This PCR product was annealed to a second PCR product comprising three copies of the Myc epitope with 5. and 3. overhangs homologous to the N- and C-terminal portions of BTLA, respectively, which had been amplified from the triple Myc/Bluescript template with primers J10-A3 (5.-GAGCATCCTTGGATCTGAACAAAAGCTGATTA-3.) (SEQ ID NO:31) and J10-A4 (5.-CTTTCTCACA-GAGCTCGTACAGGTCCTCT-3.) (SEQ ID NO:32). The triple Myc/Bluescript template contains 'anchor' sequences 5. (GS) and 3. (YEL) to the Myc3 coding sequence, which are included in the final Myc-tagged mBTLA protein. We then amplified the two annealed pieces with primers J10-RV1-Bgl2 and J10-A4. This product was annealed to a third PCR product containing a 5. Myc homologous tail and the C-terminal portion of BTLA amplified from the template mBTLAs- RV with primers J10-A5 (5.-GTACGAGCTCT-GTGAGAAAGCTACTAAGAGG-3.) (SEQ ID NO:33) and J10-Xho1, and the full-length chimeric cDNA was amplified with primers J10-RV1-Bgl2 and J10 Xho1. The resulting product was digested with BglII and XhoI and ligated into the BglII and XhoI sites of IRES-GFP-RV to yield Myc3-mBTLAs-RV.

To produce the N-terminal Myc-tagged version of mBTLA (Myc3-mBTLARV), primers J10-RV1-Bgl2 and J10-A4 were used to amplify the signal sequence linked to the triple Myc epitope from template Myc3-mBTLAs-RV. A second PCR product was amplified with primers J10-A5 and J10Xho1 and the template mJ11W1. The two PCR products were annealed and amplified with primers J10-RV1-Bgl2 and J10 Xho1, digested, and ligated into the retroviral vector to produce Myc3-mBTLA-RV. A further modification was made by using the Quick Change mutagenesis kit (Stratagene) to convert a cysteine downstream of the Myc tag to alanine to mimic more accurately the predicted signal sequence processing in which this cysteine would be removed (SignalP V2.0). .cyt-Myc3-mBTLA-RV was generated using Quick Change mutagenesis of Myc3-mBTLA-RV with the primers mJ11 trunc top (5.-TGATATTCCAT-AAAC CTGCCACTGAGCCAG-3.) (SEQ ID NO:34) and mJ11 trunc bottom (5.-TGGCAGGTTTATG GAATAT-CAACCAGGTTAGTG-3.) (SEQ ID NO:35). mBTLA-Myc2-RV, which expresses mBTLA with two C-terminal Myc epitopes, was generated by 'splicing by overlap extension' (SOEing) together two PCR products (generated from primers J10-RV1-Bgl2 and 3. mj11 Myc tail (5.-GCTTTTGTTCACTTCTCACA CAAATGGATGC-3.) (SEQ ID NO:36) with template mJ11W1, and primers 5. mj11 Myc tail (5.-TGAGGAGTGAACAAAAGCTGATT-AGCGMG-3.) (SEQ ID NO:37) and new 3. Xho Myc tail (5.-CCGCTCGAGCTCCTACAGGTCCTCTTC-3.) (SEQ ID NO:38) with template triple Myc/Bluescript) with primers J10-RV1-Bgl2 and new 3. XhoI Myc tail and Pfu polymerase. After digestion with BglII and XhoI, the PCR product was ligated into the retroviral expression vector Tb-lym-GFP RV49, which had been digested with BglII and XhoI, to generate mBTLA-Myc2-RV.

The N-terminal Myc-tagged version of hBTLA containing a triple Myc tag inserted downstream of the signal peptide (Myc3-hBTLA-RV) was prepared similarly. Three separate PCR products were generated using the following primers and templates: 5. Bgl2 hj11 (5'-GAAGATCG-CAGGAAATGAAGACATTGCCT-3'.) (SEQ ID NO:39) and 3. Myc/hj11 bottom (5'-TCAGCTTTTGTTCCCCATG-GATGTTCCAGATGTCC-3') (SEQ ID NO:40) with hj11#14u; 5. hj11/Myc top (5.-CATCCATGGGGAA-CAAAAGCTGATTAGCGAAGAG-3.) (SEQ ID NO:41) and 3. hj11/Myc bottom (5.-CACATGATTCTTTCAGGTC-CTCTTCGCTAATCAGC-3.) (SEQ ID NO:42) with triple Myc/Bluescript; and 5. Myc/hj11 top (5.-GAGGACCT-GAAAGAATCATGTGATGTACAGCTTTA-3.) (SEQ ID NO:43) and 3. Xho hj11 (5.-CCGCTCGAGTTGGAGTCA-GAAACAGACTTAAC-3.) (SEQ ID NO:44) with hj11#14u. These PCR products were sequentially annealed and amplified, and cloned into tb-lym-GFP-RV, which had been digested with BglII and XhoI. hBTLA containing three carboxy-terminal Myc epitopes (hBTLA-Myc3-RV) was generated by SOEing together two PCR products (from primers 5. Bgl2 hJ11 and 3. hJ11 Myc tail (5.-TGAGGAGT-GAACAAAAGCTGATTAGCGAAG-3.) (SEQ ID NO:45) with template hJ11#14u, and primers 5. hj11 Myc tail (5.-TGAGGAGTGAACAAAAGCTGATTAGCGAAG-3.) (SEQ ID NO:46) and new 3. Xho Myc tail with template triple Myc/Bluescript) with primers 5. Bgl2 hJ11 and new 3. Xho Myc tail and Pfu polymerase. After digestion with BglII and XhoI, the PCR product was ligated into retroviral expression vector Tb-lym-GFP-49, which had been digested with BglII and XhoI, to generate hBTLA-Myc3-RV. Embyronic stem cells (MC50) were a gift of R. Schreiber.

Tyrosine mutations. Single tyrosine-to-phenylalanine mutations of hBTLAMyc3-RV were produced using Quick Change mutagenesis and Pfu polymerase (Stratagene) with the following oligonucleotide pairs: Y226F top2 (5.-GAAACTGGAATTTATGATAATGACCCTGACCTTTG-3.) (SEQ ID NO:47) and Y226F bot (5.-GGGTCATTAT-CAAAAATTCCAGTTTCTGATAGCAG-3.) (SEQ ID NO:48); Y257F top2 (5.-ACCAGGCATTGTTTATGCTTC-CCTGAACCATTCTG-3.) (SEQ ID NO:49) and Y257F bot (5.-AGGGAAGCAAAAACAATGCCTGGTTTGT-3.) (SEQ ID NO:50) Y282F top2 (5.-GCACCAACAGAATAT-GCATCCATATGTGTAGG-3.) (SEQ ID NO:51) and Y282F bot (5.-ATATGGATGCAAATTCTGTTGGTGCT-TCTTTTA-3.) (SEQ ID NO:52). We produced double and triple tyrosine-to-phenylalanine mutations of hBTLA-Myc3-RV by using the oligonucleotide pair Y257F top2 and Y257F bot first with the Y226F-mutated hBTLA-Myc3-RV template to produce Y226F/Y257F and then with the Y282F-mutated template to produce Y257F/Y282F. The oligonucleotide pair Y282F top2 and Y282F bot was used with the Y226F-mutated template to produce Y226F/Y282F, and with the Y226F/Y257F-mutated template to produce Y226F/Y257F/Y282F.

Cell culture and expression analysis. Activation of DO11.10 TCR transgenic T cells50 and retroviral infections, northern analysis and immunoblotting49 were done as described. We prepared tissue and cellular RNA with the RNeasy Midi kit (Qiagen). A 20. stock of pervanadate was prepared 5 min before use by diluting 12.5 µl of 1 M NaVO4 and 4 µl of 30% H2O2 to 600 µl in distilled water. The Opteia Mouse IL-2 set (PharMingen) was used to measure for IL-2 by enzyme-linked immunosorbent assay (ELISA).

Immunoblotting and analysis of N-linked glycosylation. To analyze the glycosylation status cells (15. 106 per ml) were lysed in Triton X-100 lysis buffer (25 mM HEPES (pH 7.5), 0.15 M NaCl, 1% Triton (v/v), 1 mM pervanadate, 1 µg/ml of leupeptin, 1 µg/ml of pepstatin, 1 µg/ml of aprotinin and 1 mM phenyl methylsulfonyl fluoride) for 30 min at 4° C. and centrifuged at 14,000 g for 10 min. Extracts from 15. 106 cells were immunoprecipitated with 1 µg of monoclonal antibodies to Myc (clone 9E10; Santa Cruz) and 20 µl of a 1:1 slurry of protein G-Sepharose (PGS) (Pharmacia). After being washed three times in Triton lysis buffer, the pellets were boiled for 10 min in 10 µl of PNGase denaturing buffer (NEB). After centrifugation to remove PGS, eluted proteins were transferred to PCR tubes containing 1 µl of 10% Nonidet P-40 (NP-40) and 1 µl of 10. G7 buffer (NEB), divided into two 6-µl aliquots, and treated without or with 1 µl of PNGase F (NEB) for 1 h at 37° C. We boiled samples with 6 µl of 2. SDS-PAGE sample buffer and resolved them on 10% polyacrylamide gels. The proteins were transferred to nitrocellulose, blocked in 3% bovine serum albumin (BSA) in TBS-T buffer, blotted with rabbit anti-Myc (Santa Cruz) and horseradish peroxidase (HRP)-conjugated goat anti-rabbit IgG (Jackson), and analyzed by enhanced chemiluminescence (ECL). To analyze the phosphorylation status cells were treated with 1 mM pervanadate for 2 min at 37° C., placed on ice for 1 min, lysed in an equal volume of 2.1% Triton X-100 lysis buffer for 30 min and centrifuged for 10 min at 8,000 g. Extracts from 15 . 106 cells were immunoprecipitated using 1 µg of anti-Myc (clone 9E10) and PGS. Blots were first analyzed for phosphotyrosine (pTyr) using HRP-conjugated (clone 4G10, Upstate Biotechnology), and then stripped and reanalyzed using rabbit anti-Myc and HRP-conjugated goat anti-rabbit IgG.

TCR crosslinking. To analyze the induction of tyrosine phosphorylation and association with SHP-1 and SHP-2 on TCR crosslinking, we infected DO11.10 hybridoma T cells with GFP-RV48 or Myc3-mBTLAs-RV and purified them by sorting. Cells were incubated with 4 µg/ml of hamster anti-CD3ε (clone 145-2C11, PharMingen) and 2 µg/ml of anti-Myc for 30 min at 4° C., and crosslinked with 100 µg/ml of prewarmed goat anti-mouse IgG (GαM; Caltag) for various times, as indicated. We used fluorescence-activated cell sorting (FACS) to confirm the cross-reactivity of goat anti-mouse IgG with hamster anti-CD3ε. As a positive control for phosphorylation, some cells were incubated with 1 mM pervanadate for 2 min at 37° C. Cells were lysed in RIPA buffer, and 1 ml of lysates from 25. 106 cells were immunoprecipitated with 2 µg of anti-Myc (9E10). We used the following antibodies to analyze the immunoprecipitates: anti-pTyr (RC20H, Transduction Laboratories), polyclonal rabbit anti-Myc (A-14, Santa Cruz), rabbit anti-SHP-2 (C-18, Santa Cruz), rabbit anti-SHP-1 antibody (C-19, Santa Cruz) and anti-Myc (9E10). To measure the effect of crosslinking on IL-2 production, 3. 104 DO11.10 cells expressing GFP-RV, Myc3-mBTLAs-RV or Myc3-mBTLA-RV were stimulated with 1 µg/ml of immobilized anti-CD3ε in combination with various concentrations of immobilized polyclonal rabbit anti-Myc or 50 ng/ml of PMA plus 1 µM ionomycin. Culture supernatants of triplicate cultures were collected after 24 h, and the IL-2 concentration was determined by ELISA.

FACS analysis. Human IgG1 and goat anti-human PE were gifts of M. Cella (Washington Univ., St. Louis, Mo., USA). The construct for the B7h-Ig fusion protein3, a gift of W. Sha (Univ. California Berkeley), and the cDNA encoding the fusion protein were inserted into the GFP-RV retroviral vector48, and the retrovirus was used to infect J558 cells. We purified fusion protein from infected J558 supernatant with His-Bind resin (Novagen). B7.1-Ig, B7.2-Ig, PD-L1-Ig and PD-L2-Ig fusion proteins (Fc portion; human IgG1 isotype)

were obtained from R&D Systems. All analyses were done on a FACSCalibur. To measure the surface expression of BTLA, Bjab cells were infected with amphotrophic retrovirus prepared in Phoenix A packaging cells to express empty vector, Myc3-mBTLA-RV, .cyt-Myc3-mBTLA-RV and Myc3-mBTLAs- RV. Expression of the Myc epitope on GFP-positive cells was assayed on a FACScalibur with rabbit anti-Myc polyclonal serum (Santa Cruz) and PE-conjugated goat F(ab.)2 anti-rabbit IgG (Jackson Research Laboratories).

Antibody responses. Eight-week-old littermate wild-type, Btla+/. and Btla./. mice on a pure 129SvEv background (n=5) were injected intraperitoneally with 100 µg of NP17-KLH (Biosearch Technologies) in alum (Pierce) on days 0 and 14. Sera was collected on day 28, and the titers of anti-NP were determined by ELISA using NP25-BSA (Biosearch Technologies) for antibody capture and the SBA Clonotyping system/HRP kit for IgG subclass-specific ELISA (Southern Biotech).

In vitro responses of BTLA-deficient lymphocytes. T and B cells from wildtype or BTLA-deficient mice were purified by cell sorting using fluorescein isothiocyanate (FITC)-conjugated anti-CD4 (Caltag), FITC-conjugated anti- CD8α (PharMingen) or phycoerythrin (PE)-conjugated anti-B220 (PharMingen). Cells (5 . 105 per ml) were stimulated with various concentrations of plate-bound anti-1gM (Affinipure F(ab.)2 fragment goat anti-mouse IgM 115-006-075, Jackson ImmunoResearch), LPS (serotype 055:B5, Sigma), concanavalin A or plate-bound anti-CD3e (PharMingen, 145-2C11). Cell proliferation was measured after 48 h by pulsing with [3H]thymidine for 16 h.

Production and interaction of B7x-Ig. In the public databases we identified a B7 homolog, B7x, that was conserved in mouse (accession code XP__143450.2 and AAH32925.1), rat (accession code XP__227553.1) and human (accession code NP__078902.1) and was highly conserved in sequence. B7x-Ig was prepared by fusing the coding region of the extracellular domain of B7x to the CH2-CH3 domain of mouse IgG1 and a Myc-His tag in pcDNA4 (a gift of W. Sha, Univ. California Berkeley, Berkeley, Calif., USA). The construct was linearized with BglII and transfected into 293T cells with FuGENE 6 (Roche). Stable transfectants were selected in 1 mg/ml of Zeocin (Invitrogen). To obtain fusion protein, we cultured stable transfectants in serum-free Dulbecco's modified Eagle's medium for 72 h, collected the supernatant and purified B7x-Ig by affinity column chromatography over His-Bind resin (Novagen). The purity of the fusion protein was confirmed by SDS-PAGE and by immunoblotting with antibodies against Myc and mouse IgG. The following reagents were used to measure receptor and B7 ligand interactions: anti-CD4-FITC (Caltag); human IgG1 antibody (Sigma); biotinylated anti-Myc (Santa Cruz); streptavidin-PE (PharMingen); B7.1-Ig, B7.2-Ig, PD-L1-Ig and PD-L2-Ig fusion proteins (Fc portion; human IgG1 isotype; R&D Systems); goat anti-human Fcγ F(ab.)2-PE (Jackson ImmunoResearch); and anti-PD-1-PE (PharMingen).

Example 4

Identification of BTLA

In a previous Affymetrix screen, we identified an anonymous Th1-specific EST. The full-length cDNA of this EST, cloned from a murine cDNA library, predicts a protein with a signal sequence, extracellular V-like Ig domain, transmembrane region and intracellular domain of approximately 100 amino acids (FIG. 19). A homology search identified a single human gene homologue, having a similar domain structure (FIG. 19). Notably, three tyrosine residues within the cytoplasmic domain are contained within three sequence motifs that are conserved between mouse and human, the first, a potential Grb2 interaction site, and the others, ITIM, sequences (FIG. 19). In addition to BTLA, a minor alternatively spliced transcript, BTLAs, was detected by RT-PCR in mouse tissue. BTLAs lacks exon 2, and thus the Ig domain. Additionally, an alternatively spliced human BTLA transcript lacking exon 3, and thus the TM domain, and portions of the cytoplasmic and extracellular domains, was detected.

Methods for Example 4

We used an EST (aa839766) expressed by Th1, but not Th2, cells to screen a Th1 cDNA phage library made in the Lambda ZAP vector (Stratagene) and isolated a partial clone, BTLAs, that lacked an Ig domain. Full length BTLA cDNA, amplified from WEHI cell RNA by RT-PCR with primers J10-3K (5'-TTTGGCCTMGATGCTGCTA-3') (SEQ ID NO:53) and J10-7F (5'-CACAGATTGGGTAC-GACATG-3'.) (SEQ ID NO:54), was inserted into the GEM-T Easy Vector (Promega) to produce mJ11W1. We obtained additional full-length BTLA cDNA isolates by screening a second mouse splenocyte cDNA library (Stratagene) using the 5. region of mj11W1 as a probe. Coding sequence and intron-exon boundaries were further determined by sequencing 129SvEv strain bacterial artificial chromosome clones containing the BTLA region (Genome Systems). Some Ig domain sequence polymorphisms occur among mouse strains. Human BTLA cDNA, amplified from Ramos B lymphoma RNA by RT-PCR with primers hJ10 (5'-TTTTCCATCACTGATATGTGCAGG-3') (SEQ ID NO:55) and hJ10 AS (5'-GGTCCCTGTTGGAGTCA-GAAAC-3') (SEQ ID NO:56) based on the Celera human genome assembly, was inserted into the GEM-T Easy Vector to produce hJ11#14u. The Celera database sequence predicted the human BTLA amino acid sequence set forth in FIG. 19 (SEQ ID NO:6), which differs from the BTLA sequence obtained from Ramos cells (SEQ ID NO:8) at amino acid residue 138. This is likely due to polymorphism, given the different human sources. The BTLA sequence as found in Ramos cells (SEQ ID NOs:7 and 8) was used for experiments disclosed herein.

Example 5

Figure 22:
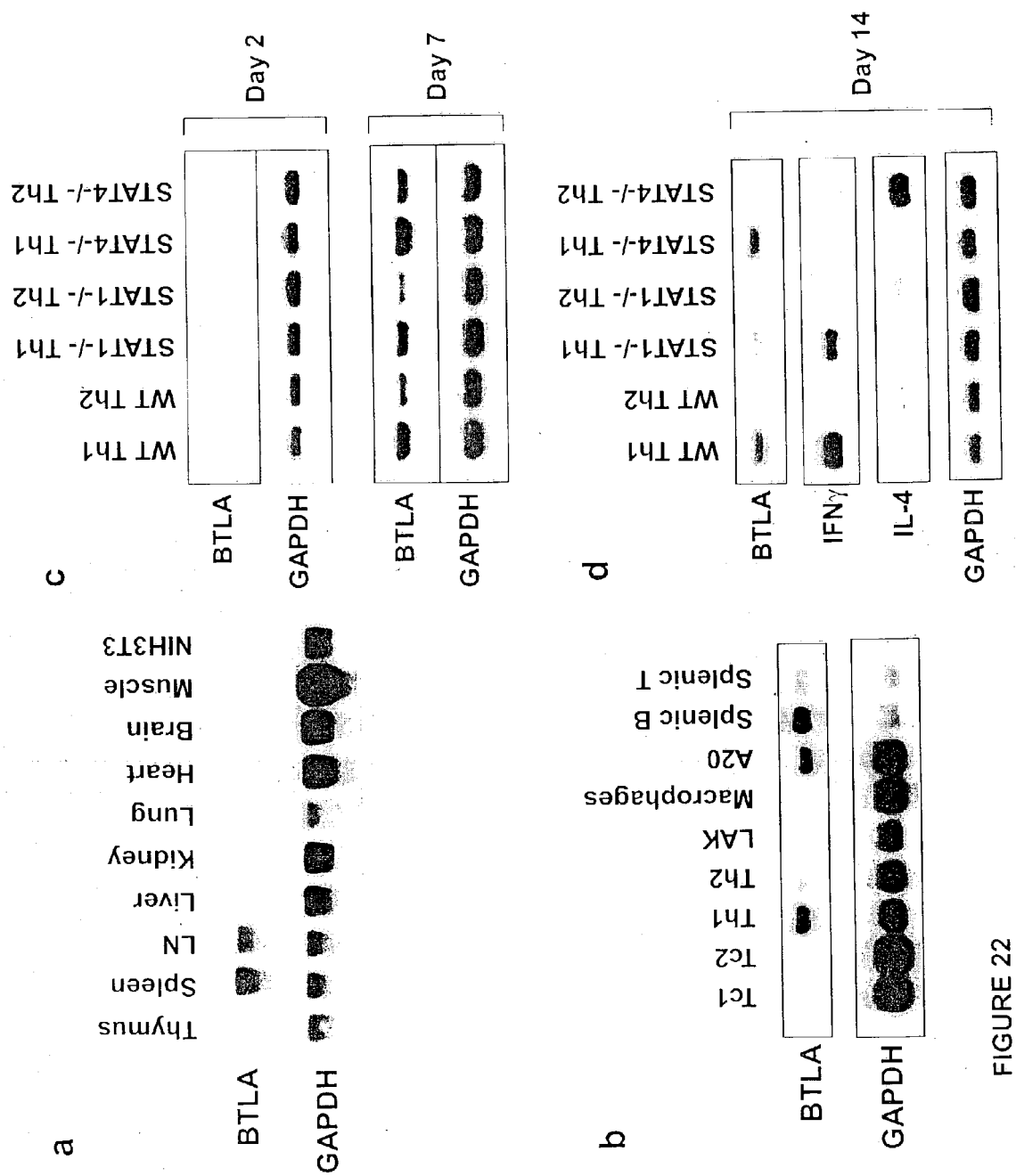
FIG. 22 shows Northern blot analyses of the expression of BTLA. 10 mg of tissue or cellular RNA, or total RNA from the indicated cells, probed with a full-length BTLA or GAPDH cDNA probe.

Expression of BTLA (FIG. 22)

BTLA is expressed strongly in spleen and lymph node tissues, but very weakly or undetectably by several somatic tissues. It is expressed by both splenic B and T cells, with slightly higher levels in the former. Further, we confirmed BTLA is expressed highly in Thl cells and resting splenic B cells, but weakly in Th2 and Tc2 cells. The A20 B cell line, but not macrophages and LAK cells, also showed BTLA expression. BTLA is expressed weakly on day 2 after primary T cell activation with no difference between Th1 and Th2 conditions. On day 7, BTLA expression is slightly higher in Th1 than Th2 cells, and after a second 2 round of polarization, BTLA expression was much stronger in Th1 than Th2 cells, and slightly diminished in Stat1−/−, but not Stat4−/−, Th1 cells. Thus, BTLA is lymphoid specific and becomes selectively expressed on Th1 cells after full polarization.

Methods for Example 5, Further Description of FIG. 22

Northern blot analysis of an organ blot probed with a full-length BTLA or GAPDH19,20 cDNA probe against 10 mg of tissue or cellular RNA prepared with RNEASY® Midi kit (QIAGEN). Northern blot analysis was also performed on blots containing total RNA from the indicated cells. Tc1 and Tc2 cells were prepared from in vitro polarized 2C21 TCR transgenic T cells, LAK cells by culturing C57/B6 splenocytes with 1000 U/ml IL-2 for 9 days, and macrophages BALB/c bone marrow derived with L-cell conditioned media and confirmed as >95% Mac-1 positive. Splenic B and T cells were purified to >98% purity by cell sorting.

Example 6

Figure 23:
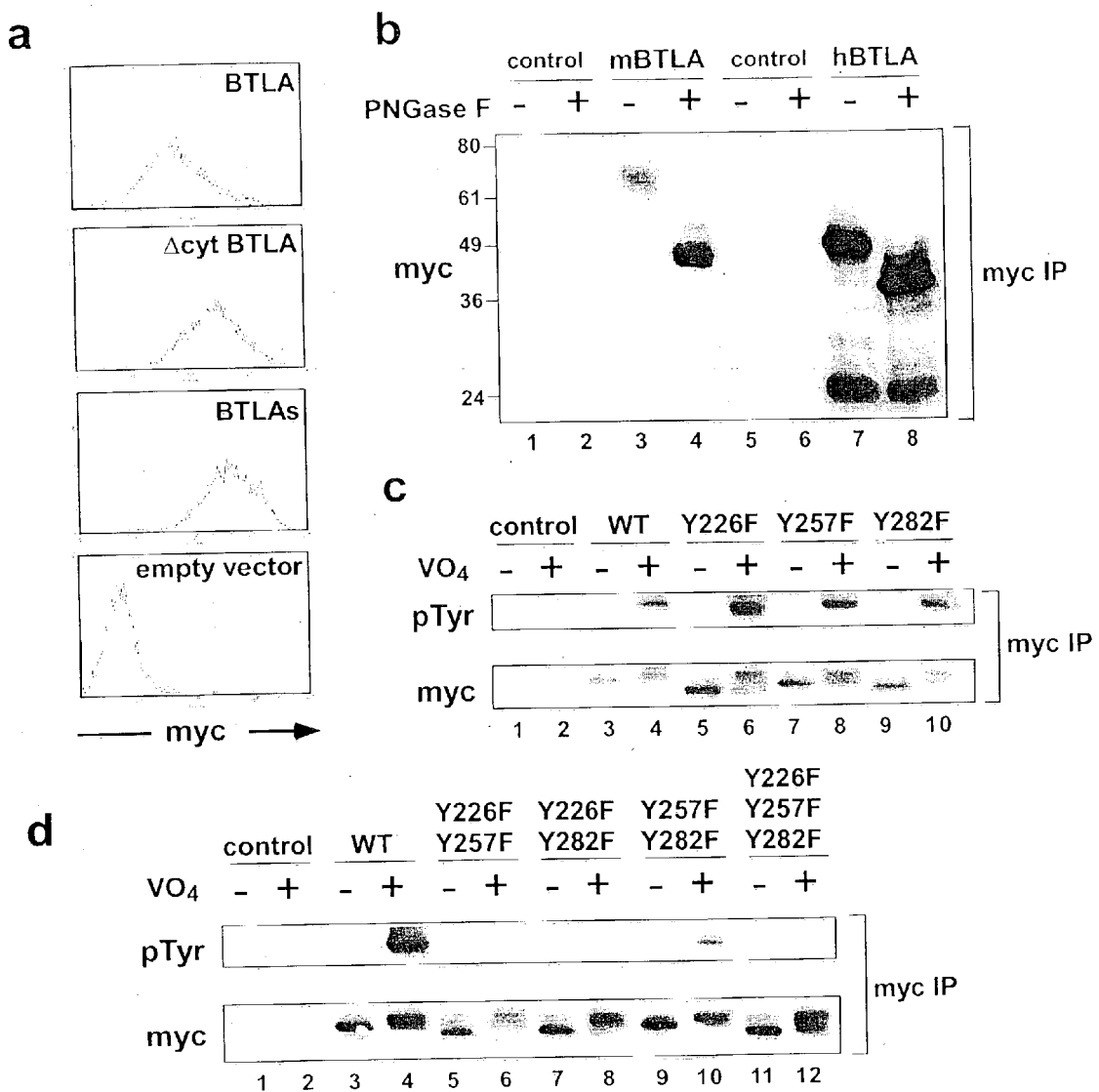
FIG. 23: BTLA is a transmembrane, glycosylated protein that is inducibly tyrosine phosphorylated.

Characterization of BTLA (FIG. 23)

To test whether BTLA is a transmembrane protein, we expressed three forms of myc-epitope tagged BTLA in the BJAB cell line. Cell surface expression of wild type BTLA was detected as predicted. Notably, deleting either the cytoplasmic or Ig domain increased surface expression, suggesting roles for these domains in controlling the level of surface expression, perhaps similar to CTLA-4 surface regulation by its cytoplasmic domain.

Next we confirmed that BTLA is a glycoprotein. Peptide N-glycosidase F treatment reduced the apparent molecular weight of both human and murine BTLA, consistent with N-linked glycosylation sites predicted present between the Ig domain and transmembrane region. The apparent molecular weight of peptide N-glycosidase F treated human and murine BTLA was still higher than predicted by its core amino acid sequence, suggesting additional modifications such as O-link glycosylation. Finally, pervanadate treatment induced tyrosine phosphotyrosine of BTLA. Single phenylalanine mutations of tyrosines 226, 257 or 282 left pervanadate-induced BTLA phosphorylation intact, but the triple tyrosine mutation blocked phosphorylation completely. The Y226F/Y257 double mutations severely reduced pervanadate-induced phosphorylation, suggesting tyrosine 282 is either weakly phosphorylated or requires prior phosphorylation at Y226 or Y257. In summary, BTLA is an Ig domain transmembrane glycoprotein that is inducibly tyrosine phosphorylated at conserved cytoplasmic ITIM like motifs.

Further Description of FIG. 23

(a) Transmembrane cell surface expression of BTLA.

BJAB cells infected with myc-tagged BTLA, Δcyt BTLA, BTLAs and empty vector were stained with anti-myc mAb (9E10, Santa Cruz) and visualized by phycoerythrin (PE)-conjugated goat anti-mouse IgG (CALTAG). Cells were analyzed on a FACScalibur and gated for GFP+ cells. (b) Murine and human BTLA contain N-linked oligosaccharides. BJAB cells infected with mouse BTLA or human BTLA were lysed and BTLA proteins were immunoprecipitated with anti-myc Ab (9E10, Santa Cruz). The immunoprecipitates were treated with peptide N-glycosidase F where indicated and analyzed by anti-myc Western blotting. (c) Tyrosine phosphorylation of BTLA upon pervanadate stimulation. BJAB cells infected with WT or single tyrosine mutants were incubated in the absence or presence of pervanadate for 2 min at 37° C. Cells were lysed and BTLA proteins were immunoprecipitated with anti-myc Ab. The immunoprecipitates were first analyzed using antipTyr (RC20H) Western blotting (top). Membrane was then stripped and incubated with rabbit anti-myc Ab (bottom). (d) BJAB cells infected with double or triple tyrosine mutants were analyzed for tyrosine phosphorylation by pervanadate treatment. Samples were prepared similarly as described above.

Example 7

Inducible Association of BTLA with SHP-2 (FIG. 24)

Sequences surrounding Y226 suggest potential Grb2 interaction, Y257 an ITIM motif, and Y282 are similar to the ITSM motif in PD-113 and SLAM (CD150/IPO-3). To evaluate such potential interactions, we developed a system of inducible BTLA phosphorylation. An extracellular myc-tagged BTLAs was expressed stably in the DO11.10 hybridoma. In similar strategy used for crosslinking PD-1 with the BCR complex, we crosslinked BTLA with the TCR using antibodies to CD3 and the myc epitope, followed by secondary crosslinking. With this approach, we detected BTLA tyrosine phosphorylation that was dependent upon secondary crosslinking and not induced with only CD3 or anti-myc antibodies alone and was specific to BTLA-transfected cell.

BTLA tyrosine phosphorylation was time dependent, appearing rapidly and optimal at 2-3 minutes, and extinguished by 10 minutes after secondary crosslinking. We surveyed various signaling molecules for co-immunoprecipitation with myc-BTLA. Notably, we found strong association with SHP-2 that occurred with the same time course as BTLA phosphorylation that was dependent upon co-crosslinking. Since SHP-2 association with BTLA was also induced by pervanadate, this condition was used to further examine SHP-2/BTLA association. Pervanadate treatment induced BTLA tyrosine phosphorylation, and SHP-2 was co-precipitated only with phosphorylated BTLA. In anti-SHP-2 immunoprecipitations, BTLA co-precipitates only in pervanadate treated cells, and not in untreated cells.

Finally, we confirmed this inducible SHP-2 association occurs for human BTLA. A myc-tagged human BTLA was expressed in the human T cell line Jurkat. Immunoprecipitated myc-hBTLA co-precipitated with SHP-2 only in pervanadate treated cells, and was specific to myc-hBTLA expression. Likewise, immunoprecipitation with anti-SHP-2 led to the coprecipitation of myc-BTLA only in pervanadate treated cells. Under these conditions, we did not detect specific co-immunoprecipitation of BTLA with Grb2, SHIP, or SHP-1.

Crosslinking BTLA with TCR attenuated IL-2 production in a T cell hybridoma. Myc-tagged BTLA and BTLAs was stably expressed in DO11.10 hybridoma T cells. The control DO11.10 hybridoma infected with GFP-RV showed anti-CD3-induced IL-2 production that was not affected by plate-bound anti-myc antibody. In contrast, IL-2 production by myc-BTLA expressing DO11.10 cells showed inhibition by plate-bound anti-myc antibody that was dose-dependent. No differences in PMA/Ionomycin-induced IL-2 production were observed.

Further Description of FIG. 24

(a) Tyrosine phosphorylation of BTLA upon TCR crosslinking. DO11.10 hybridoma T cells were infected with the empty retroviral vector (GFP-RV) or retrovirus expressing BTLAs containing an extracellular myc Epitope (myc-BTLAs) and infected cells purified by sorting. For crosslinking, cells were incubated (+) with 4 mg/ml of anti-CD3ε (clone 145-2C11, PharMingen) (αCD3) or 2 mg/ml of anti-myc (clone 9E10, Santa Cruz) (amyc) as indicated for 30 min at 4° C. After washing, cells were treated with 100 mg/ml of pre-warmed goat anti-mouse IgG antibody (CALTAG) (GaM) for indicated time. As a positive control for phosphorylation, cells were incubated with 1 mM pervanadate for 2 min at 37° C. Cells were lysed in RIPA buffer, and 1 ml lysates of 25×106 cells were immunoprecipitated with 2 mg of anti-myc antibody (9E10). Immunoprecipitates were analyzed first with anti-phosphotyrosine (RC20H, Transduction Laboratories) as described (upper panel), membranes stripped and re-probed with polyclonal rabbit anti-myc antibody (A-14, Santa Cruz) (middle panel), and finally with rabbit anti-SHP-2 antibody (C-18, Santa Cruz) (bottom panel). Arrowheads indicate the major glysosylated forms of BTLAs.

(b) BTLA tyrosine phosphorylation requires co-crosslinking. Cells described in (a) were treated (+) as described above, only with αCD3 or αmyc antibodies, as indicated, followed by secondary GαM, and analyzed as in (a) for phosphotyrosine (pTyr) (top panel) or Myc (bottom panel).

(c) Cells described in (a) were incubated in the absence (−) or presence (+) of pervanadate for 2 min at 37° C., lysed in 1% NP-40 lysis buffer and immunoprecipitated using anti-myc antibody as in (a). Immunoprecipitates and whole cell lysates (25×10$^6$) were first analyzed using antiphosphotyrosine (p-Tyr) (RC20H) (middle panel), stripped and probed for SHP-2 (top panel, and finally for Myc as in (a).

(d) Cells described in (a) were incubated in the absence (−) or presence (+) of pervanadate for 2 min at 37° C., lysed in 1% NP-40 lysis buffer and immunoprecipitated using anti-SHP-2, and immunoprecipitates and whole cell lysates analyzed using anti-myc antibody (upper panel) stripped and re-probed for SHP-2 (lower panel).

(e) Jurkat T cells were infected with GFP-RV or with a retrovirus expressing a full length human BTLA containing an N-terminal myc epitope. Infected Jurkat T cells were sorted three times to obtain a >95% population containing high surface expression of myc-hBTLA. The indicated cells were treated (+) with pervanadate for 4 min at 37° C., lysed in 1% Triton lysis buffer, immunoprecipitated with anti-myc (9E10) (left panel) or anti-SHP-2 (Santa Cruz) (right panel), and immunoprecipitates analyzed for myc, SHP-2 and phosphotyrosine as above.

(f-g) The 3×104 DO11.10 expressing control vector (GFP-RV), myc-BTLAs, or myc-BTLA were stimulated with 1 mg/ml immobilized anti-CD3ε mAb in combination with the indicated concentrations of immobilized anti-myc antibody (9E10) (f) or 50 ng/ml PMA plus 1 mM ionomycin (g). Culture supernatants of triplicate cultures were collected at 24 hours and IL-2 concentration was determined by ELISA. In (f), IL-2 titer was normalized by the IL-2 concentration induced by aCD3 stimulation alone.

Example 8

Generation and Analysis of BTLA−/− Mice. (FIG. 25)

To test for an in vivo role as an inhibitory receptor, we targeted the BTLA gene to produce BTLA−/− mice. 129SvEv background BTLA−/− lacked BTLA mRNA expression in peripheral lymphocytes. No T or B cell developmental defects in thymus or bone marrow in BTLA−/− mice. We produced mixed 129/Balb/c background BTLA−/− DO11.10 TCR transgenic mice for in vitro analysis of T cells. Fully polarized BTLA−/− Th1 cells showed enhanced proliferative responses in response to OVA-pulsed dendritic cells in vitro. Approximately two-fold increased proliferative responses were observed to 0.3 mM OVA peptide presented by CD8+ or CD8-CD11c+ dendritic cells. After NP-KLH/alum immunization, we observed approximately three-fold increase in NP-KLH specific IgG1, IgG2a and IgG2b isotypes in BTLA−/− compared to control littermate 129/SvEv mice at 4 weeks. These results suggest BTLA ligation during T cell activation might attenuate the strength of Th1 responses.

Figure 25:
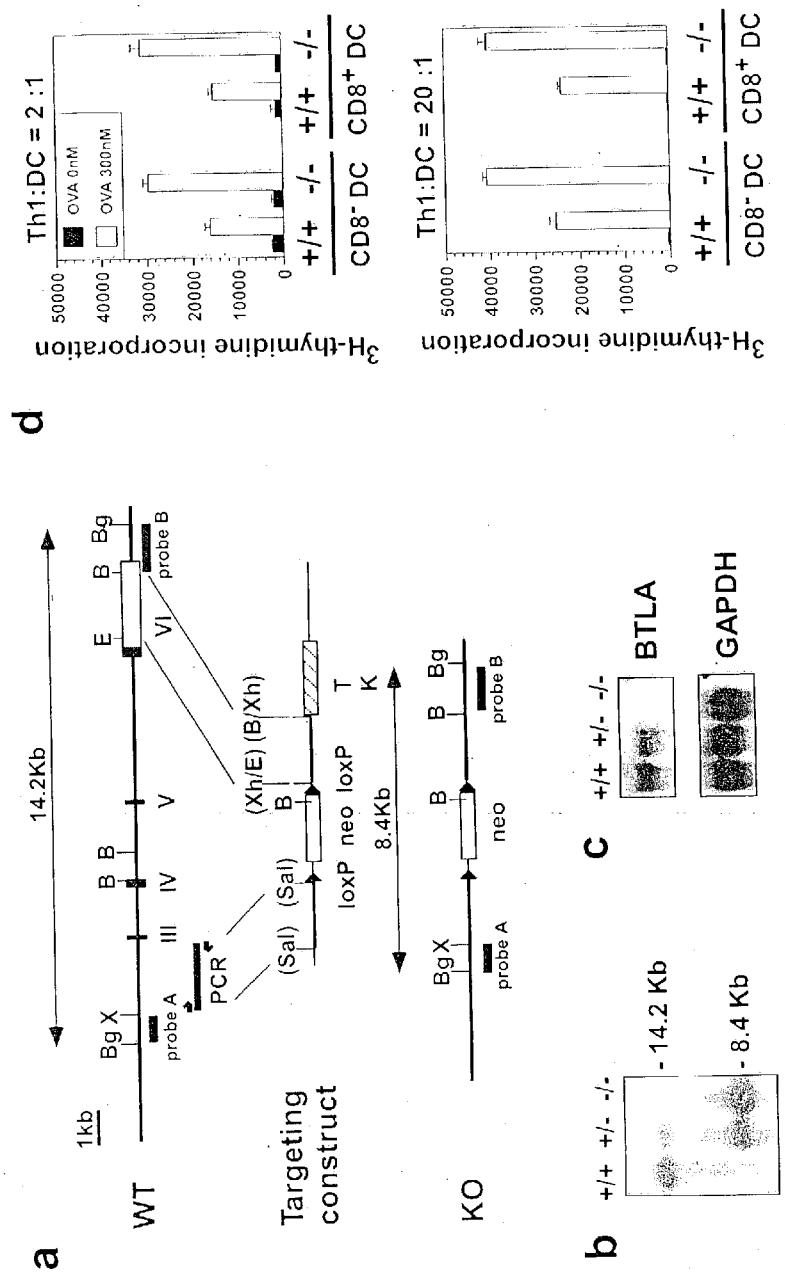

Further Description of FIG. 25

(a) The figure shows the BTLA locus and targeting construct. Exons III through VI, encoding extracellular, transmembrane and cytoplasmic regions are indicated. BglII digestion of the germline locus generates a 14.2 kb restriction fragment hybridizes to probes A and B, and 8.4 fragment in correctly targeted clones. B, BamHI; Bg, BglII; E, EcoRI; Sal, SalI; X, XbaI; Xh, XhoI. TK, thymidine kinase gene; neo, neornycinresistance cassette.

(b) Southern analysis. BglII-digested tail DNA hybridized with probe B.

(c) Northern analysis. RNA was prepared directly from splenocytes of mice of the indicated genotype, and Northern blots hybridized to a full length mouse BTLA cDNA probe, stripped and re-probed for GAPDH.

(d) Proliferative responses of polarized Th1 cells induced by incubation with Ag-pulsed DCs. BTLA−/− mice were back-crossed onto the DO11.10 TCR background. Naïve CD4 T cells from DO11.10+ BTLA+/+ or BTLA−/− mice were activated in vitro passed biweekly in Th1 conditions. Resting Th1 cells (5×10$^4$) were incubated with BALB/c derived CD8+ or CD8− DCs (2.5×104 (top) or 0.25×104 (bottom) with or without 300 nM of OVA323-339 peptide. Cell proliferation was measured by pulsing with [$^3$H]thymidine for 16 hours.

Further Description of FIG. 29

(a) Thymus, spleen and bone marrow cells from 8 week old BTLA+/+ and BTLA−/− littermates were stained using CD4-PE, CD8-FITC, CD3ε-biotin/SA-Cychrome, B220-PE, αIgM-biotin/SA-Cychrome, αIgD-FITC and CD43-FITC (PharMingen). For splenocytes and bone marrow cells, 2.4G2 (antimouse CD16/32 Ab, PharMingen) was used to block non-specific binding of staining antibodies to Fc receptors. The percentages of the live cells in the quadrants or gates are indicated. (b) Splenocytes were stained with γδ-TCR-FITC, DX5-FITC (pan NK), Gr-1-biotin/SA-Cychrome, Mac-1-biotin/SA-Cychrome, and anti-cKit-biotin/SA-Cychrome (PharMingen.) The histograms were overlayed for each marker (black line; +/+, red line; −/−). (c) Thymocytes and splenocytes from 8 weeks old BTLA+/+ and BTLA−/− littermates were counted by trypan-blue dye exclusion. The data are presented as the mean ±SD of five mice.

Example 9

B7x Binding to Lymphocytes Requires BTLA Expression (FIG. 13)

T cells purified from wildtype and BTLA −/− mice were stained B7x-Ig fusion protein, which revealed that BTLA is required for binding of B7xIg fusion protein to T cells, implicating BTLA as a counter-receptor for B7x. Additionally, as shown in FIG. 31 (b) and (c), BTLA expression is not required for the binding of B71.1Ig, B7.2Ig, PD-L1Ig, PD-L2Ig and B7hIg, to Th1 cells.

Example 10

In vitro Responses of BTLA-deficient Lymphocytes
(FIG. 32)

T and B cell from wild-type (WT) or BTLA-deficient (KO) mice were purified by cell sorting using anti-CD4-FITC, anti-CD8α-FITC or anti-B220-PE. Cells were stimulated with the indicated final concentrations of plate-bound anti-IgM, LPS, concanavalin A or plate-bound anti-CD3ε. Cell proliferation was measured by pulsing with [$^3$H]thymidine for 16 h. These results support that BTLA has inhibitory effect on lymphocyte responses.

Example 11

Increased EAE Susceptibility in BTLA−/− Mice
(FIG. 26)

To test for an in vivo action of BTLA in T cells, we considered experimental allergic encephalitis (EAE). Our data suggest BTLA may be inhibitory, so we required a system that could potentially reveal enhanced T cell responses in BTLA−/− mice. Since presently we have pure 129 background BTLA−/− mice, we determined the antigen dose-titration of the MOG peptide in this background. 10 μg and 50 μg of peptide induced severe disease in 129SvEv mice, but 2 μg induced disease, which was more mild and delayed. At this antigen does, BTLA−/− mice showed higher incidence, increased clinical score, earlier disease onset and prolonged duration compared to littermate wild type controls. Histologocial analsysis supported these results (data not shown), demonstrating infiltration of the CNS in MOG-induced EAE in BTLA-deficient mice.

Further Description of FIG. 26

(a) Titration of MOG peptide in 129 SvEv mice. 129 SvEv mice were injected subcutaneously with MOG peptide at 2 μg, 10 μg, and 50 μg (n=5) in IFA and 500 μg of mycobacterium on day 0. 300 ng of Pertussis toxin was injected intravenously on day 1 and 3. C57BL/6 mice were injected with 10 μg of MOG used as positive controls. Mice were monitored daily for clinical symptoms. Clinical scores: score 0, normal mouse, no overt signs of disease; 1, limp tail or hind limb weakness, but not both; 2, limp tail or hind limb weakness; 3, partial hind limb paralysis; 4, complete hind limb paralysis; 5, moribund state, death by EAE, sacrifice for humane reasons)

(b) Active induction of EAE by suboptimal dose of MOG peptide in BTLA−/− mice. 6-8 weeks old pure 129 SvEv BTLA−/− or wild type littermate control mice (n=5) were injected with 2 μg of MOG peptide as described in (a). Mean clinical scores: Wt, 0.6±0.9; BTLA−/−, 2.4±1.7. Mean peak clinical score; Wt, 1.5±0.7; BTLA−/− 3.0±1.2.

For further discussion, see Watanabe N, et al., BTLA is a lymphocyte inhibitory receptor with similarities to CTLA-4 and PD-1. Published online: 8 Jun. 2003, doi:10.1038/ni944 Nat Immunol. Jun. 8, 2003 [Epub ahead of print] PMID: 12796776, which is expressly incorporated herein by reference.

---

We claim:

1. A recombinant BTLA nucleic acid, encoding a BTLA protein having at least about 98% identity to the amino acid sequence set forth in SEQ ID NO:8, wherein said BTLA protein comprises an extracellular V-like Ig domain, a transmembrane region, and an intracellular domain, and is capable of inducible association with SHP-2 in T cells.

2. The recombinant BTLA nucleic acid according to claim 1, encoding a BTLA protein comprising the amino acid sequence set forth in SEQ ID NO:8.

3. The recombinant BTLA nucleic acid according to claim 1, wherein said nucleic acid comprises the nucleotide sequence set forth in SEQ ID NO:7.

4. An expression vector, comprising the recombinant BTLA nucleic acid according to any one of claims 1, 2, and 3 operably linked to regulatory sequences recognizable by a host cell transfected with the recombinant BTLA nucleic acid.

5. An isolated host cell, comprising the recombinant BTLA nucleic acid according to any one of claims 1, 2, and 3.

6. An isolated host cell, comprising the expression vector of claim 4.

7. A process for producing a BTLA protein, comprising culturing the host cell of claim 6 under conditions suitable for the expression of BTLA protein.

8. The process of claim 7, further comprising isolating the BTLA protein.

* * * * *

SEQUENCE LISTING

<160> NUMBER OF SEQ ID NOS: 56

<210> SEQ ID NO 1
<211> LENGTH: 283
<212> TYPE: PRT
<213> ORGANISM: Mus musculus

<400> SEQUENCE: 1

```
Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160
```

```
Ala Ser Ser Glu Ser Leu Arg Cys Glu Ala Pro Arg Trp Phe Pro Gln
            165                 170                 175

Pro Thr Val Ala Trp Ala Ser Gln Val Asp Gln Gly Ala Asn Phe Ser
        180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Pro Ser Pro Cys Val Phe Ser Ser Ala Phe Ala Ala Gly Trp Ala
            260                 265                 270

Leu Leu Ser Leu Ser Cys Cys Leu Met Leu Arg
            275                 280
```

<210> SEQ ID NO 2
<211> LENGTH: 282
<212> TYPE: PRT
<213> ORGANISM: Homo sapiens

<400> SEQUENCE: 2

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
```

-continued

```
                245                 250                 255
        Lys Ala Ser Leu Cys Val Ser Ser Phe Phe Ala Ile Ser Trp Ala Leu
                    260                 265                 270

Leu Pro Leu Ser Pro Tyr Leu Met Leu Lys
                    275                 280

<210> SEQ ID NO 3
<211> LENGTH: 852
<212> TYPE: DNA
<213> ORGANISM: Mus musculus

<400> SEQUENCE: 3
atggcttcct tggggcagat catcttttgg agtattatta acatcatcat catcctggct     60
ggggccatcg cactcatcat tggctttggc atttcaggca agcacttcat cacggtcacg    120
accttcacct cagctggaaa cattggagag acgggaccc tgagctgcac ttttgaacct     180
gacatcaaac tcaacggcat cgtcatccag tggctgaaag aaggcatcaa aggtttggtc    240
cacgagttca agaaggcaa agacgacctc tcacagcagc atgagatgtt cagaggccgc    300
acagcagtgt ttgctgatca ggtggtagtt ggcaatgctt ccctgagact gaaaaacgtg    360
cagctcacgg atgctggcac ctacacatgt tacatccgca cctcaaaagg caaagggaat    420
gcaaacctag agtataagac cggagccttc agtatgccag agataaatgt ggactataat    480
gccagttcag agagtttacg ctgcgaggct cctcggtggt tcccccagcc cacagtggcc    540
tgggcatctc aagtcgacca aggagccaac ttctcagaag tctcgaacac cagctttgag    600
ttgaactctg agaatgtgac catgaaggtc gtatctgtgc tctacaatgt cacaatcaac    660
aacacatact cctgtatgat tgaaaatgac attgccaaag ccactgggga catcaaagtg    720
acagattcag aggtcaaaag gcggagtcag ctgcagctgc tcaactccgg gccttccccg    780
tgtgtttttt cttctgcctt tgcggctggc tgggcgctcc tatctctctc ctgttgcctg    840
atgctaagat ga                                                        852

<210> SEQ ID NO 4
<211> LENGTH: 849
<212> TYPE: DNA
<213> ORGANISM: Homo sapiens

<400> SEQUENCE: 4
atggcttccc tggggcagat cctcttctgg agcataatta gcatcatcat tattctggct     60
ggagcaattg cactcatcat tggctttggt atttcaggga gacactccat cacagtcact    120
actgtcgcct cagctggaaa cattgggag gatggaatcc tgagctgcac ttttgaacct     180
gacatcaaac tttctgatat cgtgatacaa tggctgaagg aaggtgtttt aggcttggtc    240
catgagttca agaaggcaa agatgagctg tcggagcagg atgaaatgtt cagaggccgg    300
acagcagtgt ttgctgatca agtgatagtt ggcaatgcct ctttgcggct gaaaaacgtg    360
caactcacag atgctggcac ctacaaatgt tatatcatca cttctaaagg caagggggaat    420 gctaaccttg agtataaaac tggagccttc agcatgccgg aagtgaatgt ggactataat    480
gccagctcag agaccttgcg cgtgtgaggct ccccgatggt tcccccagcc cacagtggtc    540
tgggcatccc aagttgacca gggagccaac ttctcggaag tctccaatac cagctttgag    600
ctgaactctg agaatgtgac catgaaggtt gtgtctgtgc tctacaatgt tacgatcaac    660
aacacatact cctgtatgat tgaaaatgac attgccaaag caacagggga tatcaaagtg    720
acagaatcgg agatcaaaag gcggagtcac ctacagctgc taaactcaaa ggcttctctg    780
```

```
tgtgtctctt ctttctttgc catcagctgg gcacttctgc ctctcagccc ttacctgatg    840
ctaaaataa                                                            849
```

<210> SEQ ID NO 5
<211> LENGTH: 306
<212> TYPE: PRT
<213> ORGANISM: Mus musculus

<400> SEQUENCE: 5

```
Met Lys Thr Val Pro Ala Met Leu Gly Thr Pro Arg Leu Phe Arg Glu
1               5                   10                  15

Phe Phe Ile Leu His Leu Gly Leu Trp Ser Ile Leu Cys Glu Lys Ala
            20                  25                  30

Thr Lys Arg Asn Asp Glu Glu Cys Glu Val Gln Leu Asn Ile Lys Arg
        35                  40                  45

Asn Ser Lys His Ser Ala Trp Thr Gly Glu Leu Phe Lys Ile Glu Cys
    50                  55                  60

Pro Val Lys Tyr Cys Val His Arg Pro Asn Val Thr Trp Cys Lys His
65                  70                  75                  80

Asn Gly Thr Ile Trp Val Pro Leu Glu Val Gly Pro Gln Leu Tyr Thr
                85                  90                  95

Ser Trp Glu Glu Asn Arg Ser Val Pro Val Phe Val Leu His Phe Lys
            100                 105                 110

Pro Ile His Leu Ser Asp Asn Gly Ser Tyr Ser Cys Ser Thr Asn Phe
        115                 120                 125

Asn Ser Gln Val Ile Asn Ser His Ser Val Thr Ile His Val Arg Glu
    130                 135                 140

Arg Thr Gln Asn Ser Ser Glu His Pro Leu Ile Thr Val Ser Asp Ile
145                 150                 155                 160

Pro Asp Ala Thr Asn Ala Ser Gly Pro Ser Thr Met Glu Glu Arg Pro
                165                 170                 175

Gly Arg Thr Trp Leu Leu Tyr Thr Leu Leu Pro Leu Gly Ala Leu Leu
            180                 185                 190

Leu Leu Leu Ala Cys Val Cys Leu Leu Cys Phe Leu Lys Arg Ile Gln
        195                 200                 205

Gly Lys Glu Lys Lys Pro Ser Asp Leu Ala Gly Arg Asp Thr Asn Leu
    210                 215                 220

Val Asp Ile Pro Ala Ser Ser Arg Thr Asn His Gln Ala Leu Pro Ser
225                 230                 235                 240

Gly Thr Gly Ile Tyr Asp Asn Asp Pro Trp Ser Ser Met Gln Asp Glu
                245                 250                 255

Ser Glu Leu Thr Ile Ser Leu Gln Ser Glu Arg Asn Asn Gln Gly Ile
            260                 265                 270

Val Tyr Ala Ser Leu Asn His Cys Val Ile Gly Arg Asn Pro Arg Gln
        275                 280                 285

Glu Asn Asn Met Gln Glu Ala Pro Thr Glu Tyr Ala Ser Ile Cys Val
    290                 295                 300

Arg Ser
305
```

<210> SEQ ID NO 6
<211> LENGTH: 289
<212> TYPE: PRT
<213> ORGANISM: Homo sapiens

<400> SEQUENCE: 6

```
Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Lys Asn Ile Ser
            85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
130                 135                 140

Lys Asp Glu Met Ala Ser Arg Pro Trp Leu Leu Tyr Ser Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Leu Asn Ser Arg Leu Ala
            260                 265                 270

Arg Asn Val Lys Glu Ala Pro Thr Glu Tyr Ala Ser Ile Cys Val Arg
        275                 280                 285

Ser
```

<210> SEQ ID NO 7
<211> LENGTH: 870
<212> TYPE: DNA
<213> ORGANISM: Homo sapiens

<400> SEQUENCE: 7

```
atgaagacat tgcctgccat gcttggaact gggaaattat tttgggtctt cttcttaatc    60
ccatatctgg acatctggaa catccatggg aaagaatcat gtgatgtaca gctttatata   120
aagagacaat ctgaacactc catcttagca ggagatccct tgaactaga atgccctgtg    180
aaatactgtg ctaacaggcc tcatgtgact tggtgcaagc tcaatggaac aacatgtgta   240
aaacttgaag atagacaaac aagttggaag gaagagaaga acatttcatt tttcattcta   300
cattttgaac caatgcttcc taatgacaat gggtcatacc gctgttctgc aaattttcag   360
tctaatctca ttgaaagcca ctcaacaact ctttatgtga cagatgtaaa aggtgcctca   420
```

```
gaacgaccct ccaaggacga agtggcaagc agaccctggc tcctgtatag tttacttcct    480 ttgggggat tgcctctact catcactacc tggttctgcc tgttctgctg cctgagaagg     540
caccaaggaa agcaaaatga actctctgac acagcaggaa gggaaattaa tctggttgat    600
gctcacctta agagcgagca aacagaagca agcaccaggc aaaattccca agtactgcta    660
tcagaagctg gaattatga taatgaccct gacctttgtt tcaggatgca ggaagggtct     720
gaagtttgtt ctaatccatg cctggaagaa acaaaccag gcattgttta tgcttccctg     780
aaccattctg tcattggact gaactcaaga ctggcaagaa atgtaaaaga agcaccaaca    840
gaatatgcat ccatatgtgt gaggagttaa                                    870
```

<210> SEQ ID NO 8
<211> LENGTH: 289
<212> TYPE: PRT
<213> ORGANISM: Homo sapiens

<400> SEQUENCE: 8

```
Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
                20                  25                  30

Ser Cys Asp Val Gln Leu Tyr Ile Lys Arg Gln Ser Glu His Ser Ile
            35                  40                  45

Leu Ala Gly Asp Pro Phe Glu Leu Glu Cys Pro Val Lys Tyr Cys Ala
        50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Lys Asn Ile Ser
                85                  90                  95

Phe Phe Ile Leu His Phe Glu Pro Met Leu Pro Asn Asp Asn Gly Ser
                100                 105                 110

Tyr Arg Cys Ser Ala Asn Phe Gln Ser Asn Leu Ile Glu Ser His Ser
            115                 120                 125

Thr Thr Leu Tyr Val Thr Asp Val Lys Gly Ala Ser Glu Arg Pro Ser
        130                 135                 140

Lys Asp Glu Val Ala Ser Arg Pro Trp Leu Leu Tyr Ser Leu Leu Pro
145                 150                 155                 160

Leu Gly Gly Leu Pro Leu Leu Ile Thr Thr Trp Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Ala Gly
    210                 215                 220

Ile Tyr Asp Asn Asp Pro Asp Leu Cys Phe Arg Met Gln Glu Gly Ser
225                 230                 235                 240

Glu Val Cys Ser Asn Pro Cys Leu Glu Glu Asn Lys Pro Gly Ile Val
                245                 250                 255

Tyr Ala Ser Leu Asn His Ser Val Ile Gly Leu Asn Ser Arg Leu Ala
            260                 265                 270

Arg Asn Val Lys Glu Ala Pro Thr Glu Tyr Ala Ser Ile Cys Val Arg
        275                 280                 285
```

-continued

Ser

<210> SEQ ID NO 9
<211> LENGTH: 921
<212> TYPE: DNA
<213> ORGANISM: Mus musculus

<400> SEQUENCE: 9

```
atgaagacag tgcctgccat gcttgggact cctcggttat ttagggaatt cttcatcctc     60
catctgggcc tctggagcat cctttgtgag aaagctacta agaggaatga tgaagagtgt    120
gaagtgcaac ttaatattaa aggaattcc aaacactctg cctggacagg agagttattt    180
aaaattgaat gtcctgtgaa atactgtgtt catagaccta atgtgacttg gtgtaagcac    240
aatggaacaa tctgggtacc ccttgaagtt ggtcctcagc tatacactag ttgggaagaa    300
aatcgatcag ttccggtttt tgttctccat tttaaaccaa tacatctcag tgataacggg    360
tcgtatagct gttctacaaa cttcaattct caagttatta atagccattc agtaaccatc    420
catgtgagag aaaggactca aaactcttca gaacacccac taataacagt atctgacatc    480
ccagatgcca ccaatgcctc aggaccatcc accatggaag agaggccagg caggacttgg    540
ctgctttaca ccttgcttcc tttggggca ttgcttctgc tccttgcctg tgtctgcctg    600
ctctgctttc tgaaaaggat ccaagggaaa gaaagaagc cttctgactt ggcaggaagg    660
gacactaacc tggttgatat tccagccagt tccaggacaa atcaccaagc actgccatca    720
ggaactggaa tttatgataa tgatccctgg tctagcatgc aggatgaatc tgaattgaca    780
attagcttgc aatcagagag aaacaaccag ggcattgttt atgcttcttt gaaccattgt    840
gttattggaa ggaatccaag acaggaaaac aacatgcagg aggcacccac agaatatgca    900
tccatttgtg tgagaagtta a                                              921
```

<210> SEQ ID NO 10
<211> LENGTH: 306
<212> TYPE: PRT
<213> ORGANISM: Mus musculus

<400> SEQUENCE: 10

Met Lys Thr Val Pro Ala Met Leu Gly Thr Pro Arg Leu Phe Arg Glu
1               5                   10                  15

Phe Phe Ile Leu His Leu Gly Leu Trp Ser Ile Leu Cys Glu Lys Ala
            20                  25                  30

Thr Lys Arg Asn Asp Glu Glu Cys Glu Val Gln Leu Asn Ile Lys Arg
        35                  40                  45

Asn Ser Lys His Ser Ala Trp Thr Gly Glu Leu Phe Lys Ile Glu Cys
    50                  55                  60

Pro Val Lys Tyr Cys Val His Arg Pro Asn Val Thr Trp Cys Lys His
65                  70                  75                  80

Asn Gly Thr Ile Trp Val Pro Leu Glu Val Gly Pro Gln Leu Tyr Thr
                85                  90                  95

Ser Trp Glu Glu Asn Arg Ser Val Pro Val Phe Val Leu His Phe Lys
            100                 105                 110

Pro Ile His Leu Ser Asp Asn Gly Ser Tyr Ser Cys Ser Thr Asn Phe
        115                 120                 125

Asn Ser Gln Val Ile Asn Ser His Ser Val Thr Ile His Val Arg Glu
    130                 135                 140

Arg Thr Gln Asn Ser Ser Glu His Pro Leu Ile Thr Val Ser Asp Ile
145                 150                 155                 160

```
Pro Asp Ala Thr Asn Ala Ser Gly Pro Ser Thr Met Glu Glu Arg Pro
                165                 170                 175
Gly Arg Thr Trp Leu Leu Tyr Thr Leu Leu Pro Leu Gly Ala Leu Leu
        180                 185                 190
Leu Leu Leu Ala Cys Val Cys Leu Leu Cys Phe Leu Lys Arg Ile Gln
            195                 200                 205
Gly Lys Glu Lys Lys Pro Ser Asp Leu Ala Gly Arg Asp Thr Asn Leu
        210                 215                 220
Val Asp Ile Pro Ala Ser Ser Arg Thr Asn His Gln Ala Leu Pro Ser
225                 230                 235                 240
Gly Thr Gly Ile Tyr Asp Asn Asp Pro Trp Ser Ser Met Gln Asp Glu
                245                 250                 255
Ser Glu Leu Thr Ile Ser Leu Gln Ser Glu Arg Asn Asn Gln Gly Ile
            260                 265                 270
Val Tyr Ala Ser Leu Asn His Cys Val Ile Gly Arg Asn Pro Arg Gln
        275                 280                 285
Glu Asn Asn Met Gln Glu Ala Pro Thr Glu Tyr Ala Ser Ile Cys Val
        290                 295                 300
Arg Ser
305

<210> SEQ ID NO 11
<211> LENGTH: 322
<212> TYPE: DNA
<213> ORGANISM: Mus musculus

<400> SEQUENCE: 11
gatgaagagt gtgaagtgca acttaatatt aagaggaatt ccaaacactc tgcctggaca      60
ggagagttat ttaaaattga atgtcctgtg aaatactgtg ttcatagacc taatgtgact     120
tggtgtaagc acaatggaac aatctgggta ccccttgaag ttggtcctca gctatacact     180
agttgggaag aaaatcgatc agttccggtt tttgttctcc attttaaacc aatacatctc     240
agtgataacg ggtcgtatag ctgttctaca aacttcaatt ctcaagttat taatagccat     300
tcagtaacca tccatgtgag ag                                              322

<210> SEQ ID NO 12
<211> LENGTH: 322
<212> TYPE: DNA
<213> ORGANISM: Mus musculus

<400> SEQUENCE: 12
gatgaagagt gtgaagtgca acttaatatt aagaggaatt ccaaacactc tgcctggaca      60
ggagagttat ttaaaattga atgtcctgtg aaatactgtg ttcatagacc tcatgtgact     120
tggtgtaagc acaatggaac aatctgggta ccccttgaag ttggtcctca gctatacact     180
agttgggaag aaaatcgatc agttccggtt tttgttctcc attttaaacc aatacatctc     240
agtgataacg ggtcgtatag ctgttctaca aacttcaatt ctcaagttat taatagccat     300
tcagtaacca tccatgtgag ag                                              322

<210> SEQ ID NO 13
<211> LENGTH: 322
<212> TYPE: DNA
<213> ORGANISM: Mus musculus

<400> SEQUENCE: 13
```

```
gatgaagagt gtccagtgca acttactatt acgaggaatt ccaaacagtc tgccaggaca    60
ggagagttat ttaaaattca atgtcctgtg aaatactgtg ttcatagacc taatgtgact   120
tggtgtaagc acaatggaac aatctgtgta ccccttgagg ttagccctca gctatacact   180
agttgggaag aaaatcaatc agttccggtt tttgttctcc actttaaacc aatacatctc   240
agtgataatg ggtcgtatag ctgttctaca aacttcaatt ctcaagttat taatagccat   300
tcagtaacca tccatgtgac ag                                            322

<210> SEQ ID NO 14
<211> LENGTH: 322
<212> TYPE: DNA
<213> ORGANISM: Mus musculus

<400> SEQUENCE: 14
gatgaagagt gtgaagtgca acttaatatt aagaggaatt ccaaacactc tgcctggaca    60
ggagagttat ttaaaattga atgtcctgtg aaatactgtg ttcatagacc taatgtgact   120
tggtgtaagc acaatggaac aatctgggta ccccttgaag ttggtcctca gctatacact   180
agttgggaag aaaatcgatc agttccggtt tttgttctcc attttaaacc aatacatctc   240
agtgataacg ggtcgtatag ctgttctaca aacttcaatt ctcaagttat taatagccat   300
tcagtaacca tccatgtgag ag                                            322

<210> SEQ ID NO 15
<211> LENGTH: 322
<212> TYPE: DNA
<213> ORGANISM: Mus musculus

<400> SEQUENCE: 15
gatgaagagt gtgaagtgca acttaatatt aagaggaatt ccaaacactc tgcctggaca    60
ggagagttat ttaaaattga atgtcctgtg aaatactgtg ttcatagacc tcatgtgact   120
tggtgtaagc acaatggaac aatctgggta ccccttgaag ttggtcctca gctatacact   180
agttgggaag aaaatcgatc agttccggtt tttgttctcc attttaaacc aatacatctc   240
agtgataacg ggtcgtatag ctgttctaca aacttcaatt ctcaagttat taatagccat   300
tcagtaacca tccatgtgag ag                                            322

<210> SEQ ID NO 16
<211> LENGTH: 322
<212> TYPE: DNA
<213> ORGANISM: Mus musculus

<400> SEQUENCE: 16
gatgaagagt gtgaagtgca acttaatatt aagaggaatt ccaaacactc tgcctggaca    60
ggagagttat ttaaaattga atgtcctgtg aaatactgtg ttcatagacc taatgtgact   120
tggtgtaagc acaatggaac aatctgggta ccccttgaag ttggtcctca gctatacact   180
agttgggaag aaaatcgatc agttccggtt tttgttctcc attttaaacc aatacatctc   240
agtgataacg ggtcgtatag ctgttctaca aacttcaatt ctcaagttat taatagccat   300
tcagtaacca tccatgtgag ag                                            322

<210> SEQ ID NO 17
<211> LENGTH: 322
<212> TYPE: DNA
<213> ORGANISM: Mus musculus

<400> SEQUENCE: 17
```

```
gatgaagagt gtgaagtgca acttaatatt aagaggaatt ccaaacactc tgcctggaca      60
ggagagttat ttaaaattga atgtcctgtg aaatactgtg ttcatagacc taatgtgact     120
tggtgtaagc acaatggaac aatctgggta ccccttgaag ttggtcctca gctatacact     180
agttgggaag aaaatcgatc agttccggtt tttgttctcc attttaaacc aatacatctc     240
agtgataacg ggtcgtatag ctgttctaca aacttcaatt ctcaagttat taatagccat     300
tcagtaacca tccatgtgag ag                                              322
```

<210> SEQ ID NO 18
<211> LENGTH: 322
<212> TYPE: DNA
<213> ORGANISM: Mus musculus

<400> SEQUENCE: 18

```
gatgaagagt gtgaagtgca acttaatatt aagaggaatt ccaaacactc tgcctggaca      60
ggagagttat ttaaaattga atgtcctgtg aaatactgtg ttcatagacc tcatgtgact     120
tggtgtaagc acaatggaac aatctgggta ccccttgaag ttggtcctca gctatacact     180
agttgggaag aaaatcgatc agttccggtt tttgttctcc attttaaacc aatacatctc     240
agtgataacg ggtcgtatag ctgttctaca aacttcaatt ctcaagttat taatagccat     300
tcagtaacca tccatgtgag ag                                              322
```

<210> SEQ ID NO 19
<211> LENGTH: 322
<212> TYPE: DNA
<213> ORGANISM: Mus musculus

<400> SEQUENCE: 19

```
gatgaagagt gtgaagtgca acttaatatt aagaggaatt ccaaacactc tgcctggaca      60
ggagagttat ttaaaattga atgtcctgtg aaatactgtg ttcatagacc tcatgtgact     120
tggtgtaagc acaatggaac aatctgggta ccccttgaag ttggtcctca gctatacact     180
agttgggaag aaaatcgatc agttccggtt tttgttctcc attttaaacc aatacatctc     240
agtgataacg ggtcgtatag ctgttctaca aacttcaatt ctcaagttat taatagccat     300
tcagtaacca tccatgtgag ag                                              322
```

<210> SEQ ID NO 20
<211> LENGTH: 322
<212> TYPE: DNA
<213> ORGANISM: Mus musculus

<400> SEQUENCE: 20

```
gatgaagagt gtgaagtgca acttaatatt aagaggaatt ccaaacactc tgcctggaca      60
ggagagttat ttaaaattga atgtcctgtg aaatactgtg ttcatagacc taatgtgact     120
tggtgtaagc acaatggaac aatctgggta ccccttgaag ttggtcctca gctatacact     180
agttgggaag aaaatcgatc agttccggtt tttgttctcc attttaaacc aatacatctc     240
agtgataacg ggtcgtatag ctgttctaca aacttcaatt ctcaagttat taatagccat     300
tcagtaacca tccatgtgag ag                                              322
```

<210> SEQ ID NO 21
<211> LENGTH: 322
<212> TYPE: DNA
<213> ORGANISM: Mus musculus

```
<400> SEQUENCE: 21
gatgaagagt gtgaagtgca acttaatatt aagaggaatt ccaaacactc tgcctggaca      60
ggagagttat ttaaaattga atgtcctgtg aaatactgtg ttcatagacc taatgtgact     120
tggtgtaagc acaatggaac aatctgggta ccccttgaag ttggtcctca gctatacact     180
agttgggaag aaaatcgatc agttccggtt tttgttctcc attttaaacc aatacatctc     240
agtgataacg ggtcgtatag ctgttctaca aacttcaatt ctcaagttat taatagccat     300
tcagtaacca tccatgtgag ag                                             322

<210> SEQ ID NO 22
<211> LENGTH: 322
<212> TYPE: DNA
<213> ORGANISM: Mus musculus

<400> SEQUENCE: 22
gatgaagagt gtgaagtgca acttaatatt aagaggaatt ccaaacactc tgcctggaca      60
ggagagttat ttaaaattga atgtcctgtg aaatactgtg ttcatagacc taatgtgact     120
tggtgtaagc acaatggaac aatctgggta ccccttgaag ttggtcctca gctatacact     180
agttgggaag aaaatcgatc agttccggtt tttgttctcc attttaaacc aatacatctc     240
agtgataacg ggtcgtatag ctgttctaca aacttcaatt ctcaagttat taatagccat     300
tcagtaacca tccatgtgag ag                                             322

<210> SEQ ID NO 23
<211> LENGTH: 322
<212> TYPE: DNA
<213> ORGANISM: Mus musculus

<400> SEQUENCE: 23
gatgaagagt gtgaagtgca acttaatatt aagaggaatt ccaaacactc tgcctggaca      60
ggagagttat ttaaaattga atgtcctgtg aaatactgtg ttcatagacc taatgtgact     120
tggtgtaagc acaatggaac aatctgggta ccccttgaag ttggtcctca gctatacact     180
agttgggaag aaaatcgatc agttccggtt tttgttctcc attttaaacc aatacatctc     240
agtgataacg ggtcgtatag ctgttctaca aacttcaatt ctcaagttat taatagccat     300
tcagtaacca tccatgtgag ag                                             322

<210> SEQ ID NO 24
<211> LENGTH: 322
<212> TYPE: DNA
<213> ORGANISM: Mus musculus

<400> SEQUENCE: 24
gatgaagagt gtgaagtgca acttaatatt aagaggaatt ccaaacactc tgcctggaca      60
ggagagttat ttaaaattga atgtcctgtg gaatactgtg ttcatagacc tcatgtgact     120
tggtgtaagc acaatggaac aatctgggta ccccttgaag ttggtcctca gctatacact     180
agttgggaag aaaatcgatc agttccggtt tttgttctcc attttaaacc aatacatctc     240
agtgataacg ggtcgtatag ctgttctaca aacttcaatt ctcaagttat taatagccat     300
tcagtaacca tccatgtgag ag                                             322

<210> SEQ ID NO 25
<211> LENGTH: 322
<212> TYPE: DNA
<213> ORGANISM: Mus musculus
```

```
<400> SEQUENCE: 25
gatgaagagt gtccagtgca acttactatt acgaggaatt ccaaacagtc tgccaggaca      60
ggagagttat ttaaaattca atgtcctgtg aaatactgtg ttcatagacc taatgtgact     120
tggtgtaagc acaatggaac aatctgtgta ccccttgagg ttagccctca gctatacact     180
agttgggaag aaaatcgatc agttccggtt tttgttctcc attttaaacc aatacatctc     240
agtgataatg ggtcgtatag ctgttctaca aacttcaatt ctcaagttat taatagccat     300
tcagtaacca tccatgtgac ag                                              322

<210> SEQ ID NO 26
<211> LENGTH: 322
<212> TYPE: DNA
<213> ORGANISM: Mus musculus

<400> SEQUENCE: 26
gatgaagagt gtgaagtgca acttaatatt aagaggaatt ccaaacactc tgcctggaca      60
ggagagttat ttaaaattga atgtcctgtg gaatactgtg ttcatagacc tcatgtgact     120
tggtgtaagc acaatggaac aatctgggta ccccttgaag ttggtcctca gctatacact     180
agttgggaag aaaatcgatc agttccggtt tttgttctcc attttaaacc aatacatctc     240
agtgataacg ggtcgtatag ctgttctaca aacttcaatt ctcaagttat taatagccat     300
tcagtaacca tccatgtgag ag                                              322

<210> SEQ ID NO 27
<211> LENGTH: 322
<212> TYPE: DNA
<213> ORGANISM: Mus musculus

<400> SEQUENCE: 27
gatgaagagt gtgaagtgca acttaatatt aagaggaatt ccaaacactc tgcctggaca      60
ggagagttat ttaaaattga atgtcctgtg aaatactgtg ttcatagacc taatgtgact     120
tggtgtaagc acaatggaac aatctgggta ccccttgaag ttggtcctca gctatacact     180
agttgggaag aaaatcgatc agttccggtt tttgttctcc attttaaacc aatacatctc     240
agtgataacg ggtcgtatag ctgttctaca aacttcaatt ctcaagttat taatagccat     300
tcagtaacca tccatgtgag ag                                              322

<210> SEQ ID NO 28
<211> LENGTH: 26
<212> TYPE: DNA
<213> ORGANISM: Homo sapiens

<400> SEQUENCE: 28
agctctgaag atctctaggg aggaag                                           26

<210> SEQ ID NO 29
<211> LENGTH: 32
<212> TYPE: DNA
<213> ORGANISM: Homo sapiens

<400> SEQUENCE: 29
catgctcgag gaaggtccag acagaggtat tg                                    32

<210> SEQ ID NO 30
<211> LENGTH: 29
<212> TYPE: DNA
```

<213> ORGANISM: Homo sapiens

<400> SEQUENCE: 30
gttcagatcc aaggatgctc cagaggccc                                29

<210> SEQ ID NO 31
<211> LENGTH: 32
<212> TYPE: DNA
<213> ORGANISM: Homo sapiens

<400> SEQUENCE: 31
gagcatcctt ggatctgaac aaaagctgat ta                            32

<210> SEQ ID NO 32
<211> LENGTH: 29
<212> TYPE: DNA
<213> ORGANISM: Homo sapiens

<400> SEQUENCE: 32
ctttctcaca gagctcgtac aggtcctct                                29

<210> SEQ ID NO 33
<211> LENGTH: 31
<212> TYPE: DNA
<213> ORGANISM: Homo sapiens

<400> SEQUENCE: 33
gtacgagctc tgtgagaaag ctactaagag g                             31

<210> SEQ ID NO 34
<211> LENGTH: 30
<212> TYPE: DNA
<213> ORGANISM: Homo sapiens

<400> SEQUENCE: 34
tgatattcca taaacctgcc actgagccag                               30

<210> SEQ ID NO 35
<211> LENGTH: 33
<212> TYPE: DNA
<213> ORGANISM: Homo sapiens

<400> SEQUENCE: 35
tggcaggttt atggaatatc aaccaggtta gtg                           33

<210> SEQ ID NO 36
<211> LENGTH: 31
<212> TYPE: DNA
<213> ORGANISM: Homo sapiens

<400> SEQUENCE: 36
gcttttgttc acttctcaca caaatggatg c                             31

<210> SEQ ID NO 37
<211> LENGTH: 30
<212> TYPE: DNA
<213> ORGANISM: Homo sapiens

<400> SEQUENCE: 37
tgaggagtga acaaaagctg attagcgaag                               30

<210> SEQ ID NO 38
<211> LENGTH: 27

```
<212> TYPE: DNA
<213> ORGANISM: Homo sapiens

<400> SEQUENCE: 38
ccgctcgagc tcctacaggt cctcttc                                              27

<210> SEQ ID NO 39
<211> LENGTH: 30
<212> TYPE: DNA
<213> ORGANISM: Homo sapiens

<400> SEQUENCE: 39
gaagatctgc aggaaatgaa gacattgcct                                           30

<210> SEQ ID NO 40
<211> LENGTH: 35
<212> TYPE: DNA
<213> ORGANISM: Homo sapiens

<400> SEQUENCE: 40
tcagcttttg ttccccatgg atgttccaga tgtcc                                     35

<210> SEQ ID NO 41
<211> LENGTH: 34
<212> TYPE: DNA
<213> ORGANISM: Homo sapiens

<400> SEQUENCE: 41
catccatggg gaacaaaagc tgattagcga agag                                      34

<210> SEQ ID NO 42
<211> LENGTH: 35
<212> TYPE: DNA
<213> ORGANISM: Homo sapiens

<400> SEQUENCE: 42
cacatgattc tttcaggtcc tcttcgctaa tcagc                                     35

<210> SEQ ID NO 43
<211> LENGTH: 35
<212> TYPE: DNA
<213> ORGANISM: Homo sapiens

<400> SEQUENCE: 43
gaggacctga agaatcatg tgatgtacag cttta                                      35

<210> SEQ ID NO 44
<211> LENGTH: 32
<212> TYPE: DNA
<213> ORGANISM: Homo sapiens

<400> SEQUENCE: 44
ccgctcgagt tggagtcaga aacagactta ac                                        32

<210> SEQ ID NO 45
<211> LENGTH: 30
<212> TYPE: DNA
<213> ORGANISM: Homo sapiens

<400> SEQUENCE: 45
tgaggagtga acaaaagctg attagcgaag                                           30

<210> SEQ ID NO 46
```

```
<211> LENGTH: 30
<212> TYPE: DNA
<213> ORGANISM: Homo sapiens

<400> SEQUENCE: 46
tgaggagtga acaaaagctg attagcgaag                                    30

<210> SEQ ID NO 47
<211> LENGTH: 35
<212> TYPE: DNA
<213> ORGANISM: Homo sapiens

<400> SEQUENCE: 47
gaaactggaa tttatgataa tgaccctgac ctttg                              35

<210> SEQ ID NO 48
<211> LENGTH: 35
<212> TYPE: DNA
<213> ORGANISM: Homo sapiens

<400> SEQUENCE: 48
gggtcattat caaaaattcc agtttctgat agcag                              35

<210> SEQ ID NO 49
<211> LENGTH: 35
<212> TYPE: DNA
<213> ORGANISM: Homo sapiens

<400> SEQUENCE: 49
accaggcatt gtttatgctt ccctgaacca ttctg                              35

<210> SEQ ID NO 50
<211> LENGTH: 28
<212> TYPE: DNA
<213> ORGANISM: Homo sapiens

<400> SEQUENCE: 50
agggaagcaa aaacaatgcc tggtttgt                                      28

<210> SEQ ID NO 51
<211> LENGTH: 33
<212> TYPE: DNA
<213> ORGANISM: Homo sapiens

<400> SEQUENCE: 51
gcaccaacag aatatgcatc catatgtgtg agg                                33

<210> SEQ ID NO 52
<211> LENGTH: 33
<212> TYPE: DNA
<213> ORGANISM: Homo sapiens

<400> SEQUENCE: 52
atatggatgc aaattctgtt ggtgcttctt tta                                33

<210> SEQ ID NO 53
<211> LENGTH: 20
<212> TYPE: DNA
<213> ORGANISM: Homo sapiens

<400> SEQUENCE: 53
tttggcctaa gatgctgcta                                               20
```

```
<210> SEQ ID NO 54
<211> LENGTH: 20
<212> TYPE: DNA
<213> ORGANISM: Homo sapiens

<400> SEQUENCE: 54
cacagattgg gtacgacatg                                           20

<210> SEQ ID NO 55
<211> LENGTH: 24
<212> TYPE: DNA
<213> ORGANISM: Homo sapiens

<400> SEQUENCE: 55
ttttccatca ctgatatgtg cagg                                      24

<210> SEQ ID NO 56
<211> LENGTH: 22
<212> TYPE: DNA
<213> ORGANISM: Homo sapiens

<400> SEQUENCE: 56
ggtccctgtt ggagtcagaa ac                                        22
```